(12) United States Patent
Ciulli et al.

(10) Patent No.: US 12,187,719 B2
(45) Date of Patent: Jan. 7, 2025

(54) PROTEOLYSIS TARGETING CHIMERA (PROTACS) AS DEGRADERS OF SMARCA2 AND /OR SMARCA4

(71) Applicant: Boehringer Ingelheim International GmbH, Ingelheim am Rhein (DE)

(72) Inventors: Alessio Ciulli, Dundee (GB); Christian Dank, Deutschkreutz (AT); Emelyne Diers, Dundee (GB); William Farnaby, Fife (GB); Michael Roy, Southbank (AU); Steffen Steurer, Vienna (AT); Nicole Trainor, Dundee (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 98 days.

(21) Appl. No.: 17/285,491

(22) PCT Filed: Oct. 14, 2019

(86) PCT No.: PCT/EP2019/077830
§ 371 (c)(1),
(2) Date: Jan. 12, 2024

(87) PCT Pub. No.: WO2020/078933
PCT Pub. Date: Apr. 23, 2020

(65) Prior Publication Data
US 2021/0380579 A1     Dec. 9, 2021

(30) Foreign Application Priority Data

Oct. 16, 2018   (EP) ..................................... 18200596

(51) Int. Cl.
| C07D 417/14 | (2006.01) |
| A61K 45/06 | (2006.01) |
| C07D 417/12 | (2006.01) |
| A61P 35/00 | (2006.01) |
| C07K 5/062 | (2006.01) |

(52) U.S. Cl.
CPC ............ C07D 417/14 (2013.01); A61K 45/06 (2013.01); C07D 417/12 (2013.01)

(58) Field of Classification Search
CPC .... C07D 417/14; C07D 417/12; A61K 45/06; A61P 35/00; C07K 5/06034
See application file for complete search history.

(56) References Cited

U.S. PATENT DOCUMENTS

2017/0008904 A1   1/2017   Crew et al.

FOREIGN PATENT DOCUMENTS

| WO | 2016105518 A1 | 6/2016 |
| WO | 2016138114 A1 | 9/2016 |
| WO | 2016146985 A1 | 9/2016 |
| WO | 2016197032 A1 | 12/2016 |
| WO | 2017007612 A1 | 1/2017 |
| WO | 2017011371 A1 | 1/2017 |
| WO | 2017030814 A1 | 2/2017 |

OTHER PUBLICATIONS

Guerrero-Martínez, J.A., Reyes, J.C. High expression of SMARCA4 or SMARCA2 is frequently associated with an opposite prognosis in cancer. Sci Rep 8, 2043 (2018). https://doi.org/10.1038/s41598-018-20217-3 (Year: 2018).*
NIH National Library of Medicine, p53 Tumor Suppressor (Year: 2024).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022) (Year: 2022).*
Cecil Textbook of Medicine, 1997, 20th Ed, Oncology (Year: 1997) (Year: 1997).*
Merriam-Webster, definition of Prevent, 2024, https://www.merriam-webster.com/dictionary/prevent (Year: 2024) (Year: 2024).*
Bondeson, Daniel P. et al. "Lessons in PROTAC Design from Selective Degradation with a Promiscuous Warhead" (2018) Cell Chemical Biology, 25, 78-87.
Cai-Hong Jia et al. "Research Progess of SWI/SNF Complex-related Genes in Tumors" (2018) Inner Mongolia Medical Unversity, 3 pgs (English abstract).
Duan, Ying-chao et al. "Advances in the treatment of cancer by PROTACs" (2017) Acta Pharmaceutica Sinica, vol. 52, No. 12, 1801-1810 (English Abstract).

(Continued)

*Primary Examiner* — Bruck Kifle
*Assistant Examiner* — Kevin S Martin
(74) *Attorney, Agent, or Firm* — Mary Breen Smith

(57) ABSTRACT

The present invention encompasses compounds of formula (1)

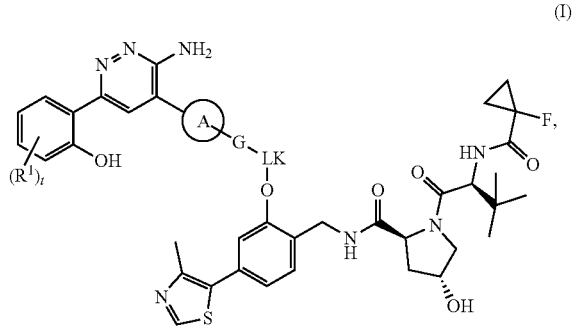

wherein the groups R¹, A, G, LK and t have the meanings given in the claims and specification, their use as degraders of SMARCA2 and/or SMARCA4, pharmaceutical compositions which contain compounds of this kind and their use as medicaments/medical uses, especially as agents for treatment and/or prevention of oncological diseases.

21 Claims, No Drawings

Specification includes a Sequence Listing.

(56) References Cited

OTHER PUBLICATIONS

Hoffman, Gregory R. et al. "Functional epigenetics approach identifies BRM/SMARCA2 as a critical synthetic lethal target in BRG1-deficient cancers" (2014) PNAS, vol. 111, No. 8, 3128-3133.
International Report on Patentablity for PCT/EP2019/077830 mailed Apr. 29, 2021.
Oike, Takahiro et al. "A Synthetic Lethality-Based Strategy to Treat Cancers Harboring a Genetic Deficiency in the Chromatin Remodeling Factor BRG1" (2013) Cancer Research, 73 (17) 5508-5518.
Maniaci, Nature Communications, HO<O-PROTACS: bivalent small molecule dimerizers of the VHL E3 ubiquitin ligase to induce self drgardation, 2017.
Collins, Biochem Journal, Chemical Approached to targeted protein, 2017.
Zengerle, College of Life Sciences, Selective Small Molecule induced Degradation of the BET Bromodomain Protein, 2015.
Bondeson, Nat. Chem. Biol, Catalytic in vivo protein, 2015.
Soares, Journal of Med. Chem, Group based Optimization of potent and cell based inhibitors, 2017.
Internatiol Search Report for PCT/EP2019/077830 mailed Jan. 16, 2020.
Gadd, Nat chem. Biol, Structural Basis od PROTAC cooperative recognition for selective protein degradation, vol. 13, 2017.
Gechijian, Nat, Chem. Biol, Functinal TRIM24 degrader via conjugation of ineffectual bromodomain and VHL ligands, vol. 14, 2018.
Gerstenberger, J, Med. Chem, Idenitifcation of a Medical Probe, vol. 59, 2016.
Hodges, Cold Spring Harbor Perspectives in Medicine, The Many Roles of BAF, 2016.
Hoffman, PNAS, Functional epigentics approach identifies BRM as a critical synthetic, 2014.
Hughes, Essays in Biochem, Molecular Recognition of ternary compleaxes, 2017.
Kadoch, AA for Advacement of Science, Mammalian SWI/SNF chromatin remodeling complexes and cancer, 2015.
Kadoch, Nat. Inst. of Health, Proteomic and Bioinformatic Analysis of SWI/SNF Complexes vol. 45, 2013.
Lu, ACTA Pharmacologica Sinica, Idientifcation of Small Molecule Inhibitors, 2018.
Nowak, Nat. Chem, Biol, Plasticity in binding confers selectivity in ligand induced protein degradation, 2018.
Oike, Cancer Research, A Synthetic Lethalith based strategy to treat cancers harboring a genetic deficiency, 2013.
Shain, PLOS one, The spectrum of SWI/SNF Mutations, vol. 8, 2013.
Shi, Genes and Development, ROle of SWI/SNFin acute leukemia maintenance, vol. 27, 2013.
St. Pierre, Current Opin, Genetic Devel., Mammalian SWI/SNF Complexes in Cancer, vol. 42, 2017.
Sutherell, J. of Med. Chem., Identification and Development of 2,3 Dihydropyrrolo{1,2-a)quinazolin-5(1H)-one Inhibitors, vol. 59, 2016.
Toure, Med. Chem, Small-Molecule PROTACS, vol. 55, 2016.
Winter, Science, Phthalimide conjugamtion as a strategy for in vivo target protein, 2015.
Wilson, Mol. Cell Bioll, Residual complexes containing SMARCA2 oncogenic drive, vol. 34, 2014.
Vangamudi, Cancer Research, The SMARCA2/ATpase DOmain surpasses the Bromodomain as a drug target in SWI/ SNF mutant cancers: vol. 45, 2015.

* cited by examiner

SEQUENCE LISTING

<160> NUMBER OF SEQ ID NOS: 2

<210> SEQ ID NO 1
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: ElonginB followed by a short spacer and AviTag Sequence at the C-terminus

<400> SEQUENCE: 1

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
            20                  25                  30

Gly Ile Leu Lys Arg Pro Pro Asp Glu Gln Arg Leu Tyr Lys Asp Asp
        35                  40                  45

Gln Leu Leu Asp Asp Gly Lys Thr Leu Gly Glu Cys Gly Phe Thr Ser
    50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95

Pro Glu Leu Pro Asp Val Met Lys Gly Ser Pro Ala Gly Gly Gly Leu
            100                 105                 110

Asn Asp Ile Phe Glu Ala Gln Lys Ile Glu Trp His Glu
        115                 120                 125

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 2

His His His His His His
1               5

PROTEOLYSIS TARGETING CHIMERA (PROTACS) AS DEGRADERS OF SMARCA2 AND /OR SMARCA4

SEQUENCE DISCLOSURE

This application includes, as part of its disclosure, a Sequence Listing text file format pursuant to 37 C.F.R. § 1.831(a) which is submitted in ASCII file format via the USPTO patent electronic filing system in a file named "12-0434-US-1_SLFINAL.txt", created on Jun. 14, 2021, and having a size of 2 kilobytes, which is hereby incorporated by reference herein in its entirety.

FIELD OF THE INVENTION

The present invention relates to new proteolysis targeting chimera (PROTACS) and derivatives of formula (I)

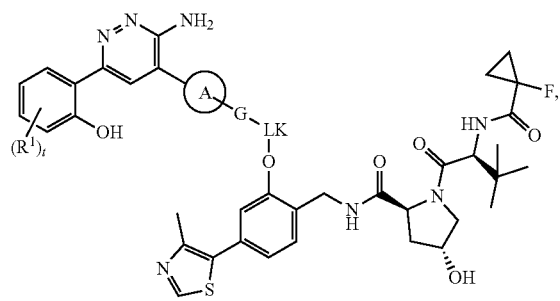

(I)

wherein the groups $R^1$, A, G, LK and t have the meanings given in the claims and specification, their use as degraders of SMARCA, pharmaceutical compositions which contain compounds of this kind and their use as medicaments/medical uses, especially as agents for treatment and/or prevention of oncological diseases.

BACKGROUND OF THE INVENTION

Classical small molecule drugs bind to their target proteins to modulate their activities, in most cases inhibiting them. In contrast, proteolysis targeting chimeras (PROTACs) bind to their target proteins to cause their degradation. PROTACs are tripartite molecules consisting of a part binding to the protein that is to be degraded, a second part that binds to an E3 ubiquitin ligase, and a linker. Whenever a trimeric complex consisting of the drug target, the PROTAC, and the ligase is formed, the close proximity of the ligase to the target results in target protein ubiquitylation. The multi-ubiquitin chain on the target protein is then recognized by the proteasome and the target protein is degraded (Collins et al., 2017; Hughes and Ciulli, 2017; Toure and Crews, 2016).

In contrast to classical small molecule drugs, PROTAC driven degradation functions in a sub-stoichiometric nature thus requiring lower systemic exposures to achieve efficacy (Bondeson et al., 2015; Winter et al., 2015). PROTACs have been shown to display higher degrees of selectivity for protein degradation than the target ligand itself due to complementarity differences in the protein-protein-interaction interfaces of the formed ternary complexes (Bondeson et al., 2018; Gadd et al., 2017; Nowak et al., 2018; Zengerle et al., 2015). In addition, PROTACs promise to expand the druggable proteome as degradation is not limited to the protein domain functionally responsible for the disease. In the case of challenging multidomain proteins, traditionally viewed as undruggable targets, the most ligandable domain can be targeted for degradation independent of its functionality or vulnerability to small molecule blockade (Gechijian et al., 2018).

The ATP-dependent activities of the BAF (SWI/SNF) chromatin remodeling complexes affect the positioning of nucleosomes on DNA and thereby many cellular processes related to chromatin structure, including transcription, DNA repair and decatenation of chromosomes during mitosis (Kadoch and Crabtree, 2015; St Pierre and Kadoch, 2017). Several subunits of the BAF complex are recurrently mutated in human cancers, adding up to roughly 20% of human tumors in which at least one BAF complex subunit is mutated. The complex contains two mutually exclusive ATPases, SMARCA2 and SMARCA4.

SMARCA4 is amongst the recurrently mutated subunits in several tumor indications including lung, liver and colon. Mutations are not clustered in a particular part of the protein and therefore presumed to be mostly loss of function events (Hodges et al., 2016; Kadoch et al., 2013; Shain and Pollack, 2013; St Pierre and Kadoch, 2017). While SMARCA4 acts as a tumor suppressor in solid tumors, the role of SMARCA4 in acute myeloid leukemia (AML) is markedly different, such that it is required to maintain the oncogenic transcription program and drive proliferation (Shi et al., 2013). Selective suppression of SMARCA2 activity has been proposed as a therapeutic concept for SMARCA4 mutated cancers (Hoffman et al., 2014b; Oike et al., 2013a; Wilson et al., 2014).

Small molecule ligands targeting the bromodomains of SMARCA2 and SMARCA4 (SMARCA2/SMARCA4$^{BD}$) have been reported (Gerstenberger et al., 2016; Hoffman et al., 2014b; Sutherell et al., 2016, Lu et al., 2018; WO 2016/138114). Although cells lacking SMARCA4 activity are vulnerable to the loss of SMARCA2 (Hoffman et al., 2014a; Oike et al., 2013b), SMARCA2/4$^{BD}$ inhibitors have failed to phenocopy these anti-proliferative effects (Vangamudi et al., 2015). In agreement with this, re-expression of SMARCA2 variants in cells, where the endogenous protein had been suppressed, showed that an intact bromodomain is not required to maintain proliferation (Vangamudi et al., 2015). SMARCA2/4$^{BD}$ inhibitors are thus precluded from use for the treatment of SMARCA4 mutant cancers but could provide attractive ligands for PROTAC conjugation. We therefore reasoned that a PROTAC targeting the non-functional bromodomain of SMARCA2/4 should offer an opportunity to exploit the vulnerability of SMARCA2 in SMARCA4 mutated cancer cells for therapeutic purposes. The principle of conjugation of a suitable SMARCA ligand with an E3 ligase binder has been described in general (WO 2016/105518; WO 2017/007612; WO 2017/011371). However, in none of the publications a concrete example and corresponding degradation of SMARCA proteins has been demonstrated. Small molecule ligands for VHL have been recently described (Soares et al., 2018).

REFERENCES

Bondeson, D. P. et al. (2015). Catalytic in vivo protein knockdown by small-molecule PROTACs. Nature Chemical Biology 11, 611.

Bondeson, D. P. et al. (2018). Lessons in PROTAC Design from Selective Degradation with a Promiscuous Warhead. Cell Chemical Biology 25, 78-87.e75.

Collins, I. et al. (2017). Chemical approaches to targeted protein degradation through modulation of the ubiquitin-proteasome pathway. Biochem J 474, 1127-1147.

Gadd, M. S. et al. (2017). Structural basis of PROTAC cooperative recognition for selective protein degradation. Nature Chemical Biology 13, 514-521.

Gechijian, L. N. et al. (2018). Functional TRIM24 degrader via conjugation of ineffectual bromodomain and VHL ligands. Nature Chemical Biology 14, 405-412.

Gerstenberger, B. S. et al. (2016). Identification of a Chemical Probe for Family VIII Bromodomains through Optimization of a Fragment Hit. Journal of Medicinal Chemistry 59, 4800-4811.

Hodges, C. et al. (2016). The Many Roles of BAF (mSWI/SNF) and PBAF Complexes in Cancer. Cold Spring Harb Perspect Med 6.

Hoffman, G. R. et al. (2014a). Functional epigenetics approach identifies BRM/SMARCA2 as a critical synthetic lethal target in BRG1-deficient cancers. Proc. Natl. Acad. Sci. U. S. A 111, 3128-3133.

Hoffman, G. R. et al. (2014b). Functional epigenetics approach identifies BRM/SMARCA2 as a critical synthetic lethal target in BRG1-deficient cancers. Proceedings of the National Academy of Sciences 111, 3128-3133.

Hughes, S. J. and Ciulli, A. (2017). Molecular recognition of ternary complexes: a new dimension in the structure-guided design of chemical degraders. Essays Biochem 61, 505-516.

Kadoch, C. and Crabtree, G. R. (2015). Mammalian SWI/SNF chromatin remodeling complexes and cancer: Mechanistic insights gained from human genomics. Science Advances 1, e1500447-e1500447.

Kadoch, C. et al. (2013). Proteomic and bioinformatic analysis of mammalian SWI/SNF complexes identifies extensive roles in human malignancy. Nature Genetics 45, 592-601.

Lu, T. et al. (2018). Identification of small molecule inhibitors targeting the SMARCA2 bromodomain from a high-throughput screening assay. Acta Pharmacologoca Sinica 39, 1-9.

Nowak, R. P. et al. (2018). Plasticity in binding confers selectivity in ligand-induced protein degradation. Nature Chemical Biology.

Oike, T. et al. (2013a). A synthetic lethality-based strategy to treat cancers harboring a genetic deficiency in the chromatin remodeling factor BRG1. Cancer Res 73, 5508-5518.

Oike, T. et al. (2013b). A synthetic lethality-based strategy to treat cancers harboring a genetic deficiency in the chromatin remodeling factor BRG1. Cancer Res.

Shain, A. H. and Pollack, J. R. (2013). The spectrum of SWI/SNF mutations, ubiquitous in human cancers. PLoS One 8, e55119.

Shi, J. et al. (2013). Role of SWI/SNF in acute leukemia maintenance and enhancer-mediated Myc regulation. Genes Dev 27, 2648-2662.

Soares, P. et al. (2018) Group-Based Optimization of Potent and Cell-Active Inhibitors of the von Hippel-Lindau (VHL) E3 Ubiquitin Ligase: Structure-Activity Relationship Leading to the Chemical Probe (2S,4R)-1-((S)-2-1 (1-Cyanocyclopropanecarboxamido)-3,3-dimethylbutanoyl)-4-hydroxy-N-(4-(4-methylthiazol-5-yl)benzyl) pyrrolidine-2-carboxamide (VH198). J. Med. Chem. 61, 599-618.

St Pierre, R. and Kadoch, C. (2017). Mammalian SWI/SNF complexes in cancer: emerging therapeutic opportunities. Curr Opin Genet Dev 42, 56-67.

Sutherell, C. L. et al. (2016). Identification and Development of 2,3-Dihydropyrrolo[1,2-a]quinazolin-5(1 H)-one Inhibitors Targeting Bromodomains within the Switch/Sucrose Nonfermenting Complex. Journal of Medicinal Chemistry 59, 5095-5101.

Toure, M. and Crews, C. M. (2016). Small-Molecule PROTACS: New Approaches to Protein Degradation. Angew Chem Int Ed Engl 55, 1966-1973.

Vangamudi, B. et al. (2015). The SMARCA2/4 ATPase Domain Surpasses the Bromodomain as a Drug Target in SWI/SNF-Mutant Cancers: Insights from cDNA Rescue and PFI-3 Inhibitor Studies. Cancer Research 75, 3865-3878.

Wilson, B. G. et al. (2014). Residual complexes containing SMARCA2 (BRM) underlie the oncogenic drive of SMARCA4 (BRG1) mutation. Mol Cell Biol 34, 1136-1144.

Winter, G. E. et al. (2015). Phthalimide conjugation as a strategy for in vivo target protein degradation. Science 348, 1376-1381.

Zengerle, M. et al. (2015). Selective Small Molecule Induced Degradation of the BET Bromodomain Protein BRD4. ACS Chemical Biology 10, 1770-1777.

DETAILED DESCRIPTION OF THE INVENTION

Compounds

It has now been found that, surprisingly, compounds of formula (I) wherein the groups $R^1$, A, G, LK and t have the meanings given hereinafter act as degraders of SMARCA2 and/or SMARCA4 which are involved in in the control of cell proliferation. Thus, the compounds according to the invention may be used for example for the treatment of diseases characterised by excessive or abnormal cell proliferation.

The present invention therefore relates to a compound of formula (I)

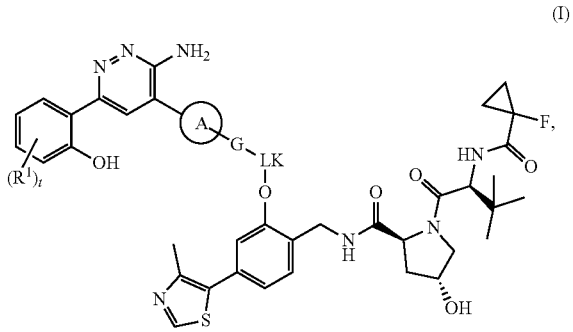

wherein

[A0]

each $R^1$ is independently selected from the group consisting of halogen, —CN, —$CF_3$, —$OCF_3$, $C_{1-3}$alkyl and $C_{1-3}$alkoxy;

t is 0, 1 or 2;

[B0]
ring A is selected from the group consisting of $C_{4-7}$cycloalkylene, $C_{4-7}$cycloalkenylene and 4-7 membered nitrogen-containing heterocyclylene, wherein said $C_{4-7}$cycloalkylene, $C_{4-7}$cycloalkenylene and 4-7 membered nitrogen-containing heterocyclylene is optionally substituted with one or more, identical or different substituent(s) selected from the group consisting of halogen, $C_{1-4}$alkyl and oxo;

[C0]
G is selected from the group consisting of a bond, —NH—, —N($C_{1-4}$alkyl)- and —O—;

[D0]
LK is —U—V—W—, wherein U binds to G;
U is selected from the group consisting of a bond, carbonyl, $C_{1-12}$alkylene, $C_{6-10}$arylene, 5-10 membered heteroarylene, —$(CH_2)_nO$— and —$O(CH_2)_n$—;
V is selected from the group consisting of a bond, carbonyl, $C_{1-12}$alkylene, $C_{6-10}$arylene, 5-10 membered heteroarylene, —$(CH_2)_nO$— and —$O(CH_2)_n$—;
W is selected from the group consisting of a bond, carbonyl, $C_{1-12}$alkylene, $C_{6-10}$arylene, 5-10 membered heteroarylene, —$(CH_2)_nO$— and —$O(CH_2)_n$—;
wherein each of said $C_{6-10}$arylene and of said 5-10 membered heteroarylene in U, V and W is optionally independently substituted with one to three, identical or different substituent(s) selected from the group consisting of halogen, $C_{1-4}$alkyl, $C_{1-4}$alkoxy and —CN;
wherein at least one of U, V and W is different from the other two;
wherein U and W are not —O— if V is —O—;
each n is independently selected from 0 to 8;
or a salt thereof.

In one aspect [A1] the invention relates to a compound of formula (I) or a salt thereof, wherein
$R^1$ is halogen;
t has the value 1 or 2.

In another aspect [A2] the invention relates to a compound of formula (I) or a salt thereof, wherein
$R^1$ is fluorine;
t has the value 1 or 2.

In another aspect [A3] the invention relates to a compound of formula (I) or a salt thereof, wherein
t is 0.

In another aspect [B1] the invention relates to a compound of formula (I) or a salt thereof, wherein
ring A is selected from the group consisting of

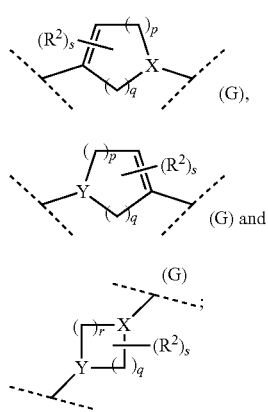

each p is independently selected from 0, 1 and 2;
each q is independently selected from 1 and 2;
r is 1, 2 or 3;
each s is independently selected from 0, 1 or 2;
each $R^2$ is independently selected from the group consisting of halogen, $C_{1-4}$alkyl and oxo;
each X is independently >CH— or >N—; and
each Y is independently >CH— or >N—.

In another aspect [B2] the invention relates to a compound of formula (I) or a salt thereof, wherein
ring A is

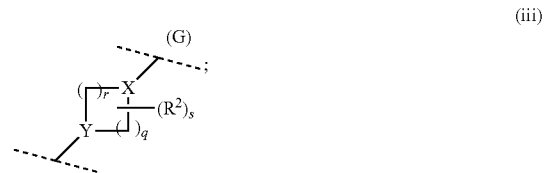

q is independently selected from 1 and 2;
r is 1, 2 or 3;
s is independently selected from 0, 1 or 2;
each $R^2$ is independently selected from the group consisting of halogen, $C_{1-4}$alkyl and oxo;
X is >CH— or >N—; and
Y is >CH— or >N—.

In further aspects [B3], [B4] and [B5] the invention relates to a compound of formula (I) or a salt thereof with structural aspects [B0], [B1] or [B2], wherein
s is 0.

In another aspect [B6] the invention relates to a compound of formula (I) or a salt thereof, wherein
ring A is selected from the group consisting of

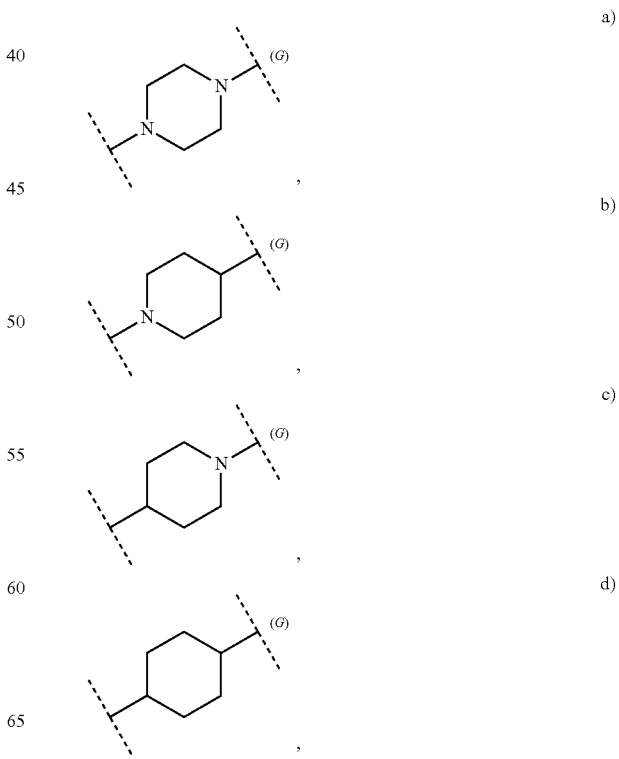

e) 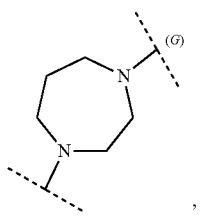,
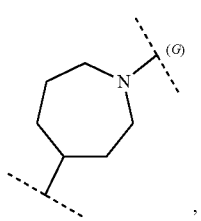,
g) 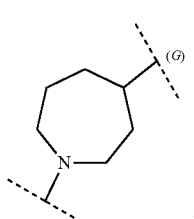,
h) 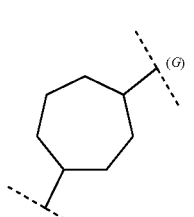,
i) 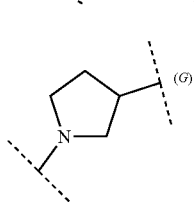,
j) 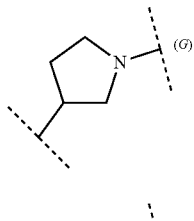,
k) 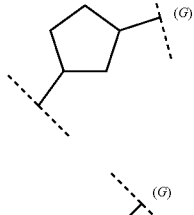,
l) 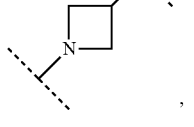,
m) 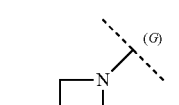
and
n) 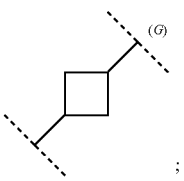;
wherein each ring a) to n) is optionally substituted by one or two substituent(s) independently selected from the group consisting of halogen, $C_{1-4}$alkyl and oxo.
In another aspect [B7] the invention relates to a compound of formula (I) or a salt thereof, wherein
ring A is selected from the group consisting of
a) 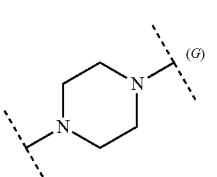,
b) 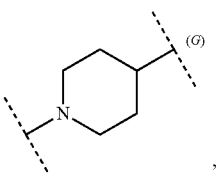,
c) 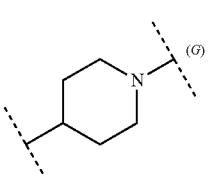,
d) 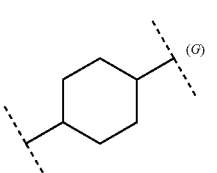,
e) 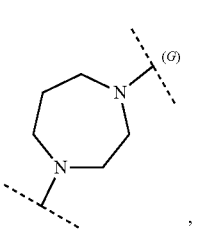, -continued

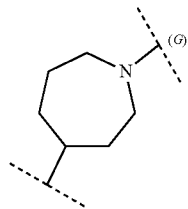

f)

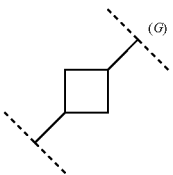

g)

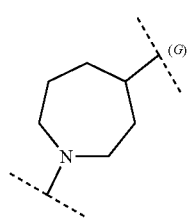

In another aspect [B8] the invention relates to a compound of formula (I) or a salt thereof, wherein
ring A is selected from the group consisting of h)

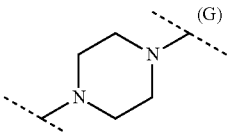
a)

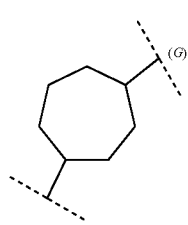

i)

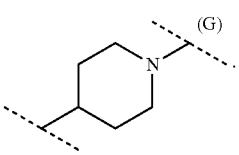
c)

In another aspect [B9] the invention relates to a compound of formula (I) or a salt thereof, wherein
ring A is j)

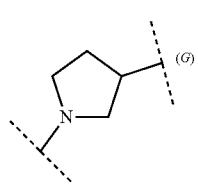

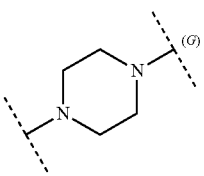
a)

k)

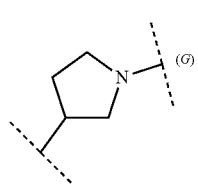

In another aspect [C1] the invention relates to a compound of formula (I) or a salt thereof, wherein G is a bond.

In another aspect [D1] the invention relates to a compound of formula (I) or a salt thereof, wherein LK is —U—V—W—, wherein U binds to G;

U is selected from the group consisting of carbonyl, $C_{1-12}$alkylene and (G) —(CH$_2$)$_n$O—;

l)

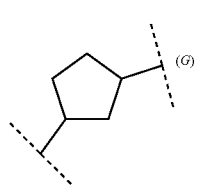

V is selected from the group consisting of a bond, $C_{1-12}$alkylene, $C_{6-10}$arylene, 5-10 membered heteroarylene and (U) —(CH$_2$)$_n$O—;

W is selected from the group consisting of a bond, $C_{1-12}$alkylene and (V) —O(CH$_2$)$_n$—;

wherein each of said $C_{6-10}$arylene in V is optionally substituted with one halogen;

m)

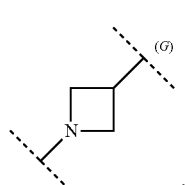

wherein at least one of U, V and W is different from the other two;

wherein U and W are not —O— if V is —O—;

each n is independently selected from 0 to 8.

In another aspect [D2] the invention relates to a compound of formula (I) or a salt thereof, wherein

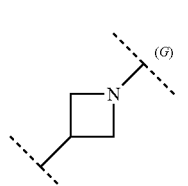

and

LK is selected from the group consisting of

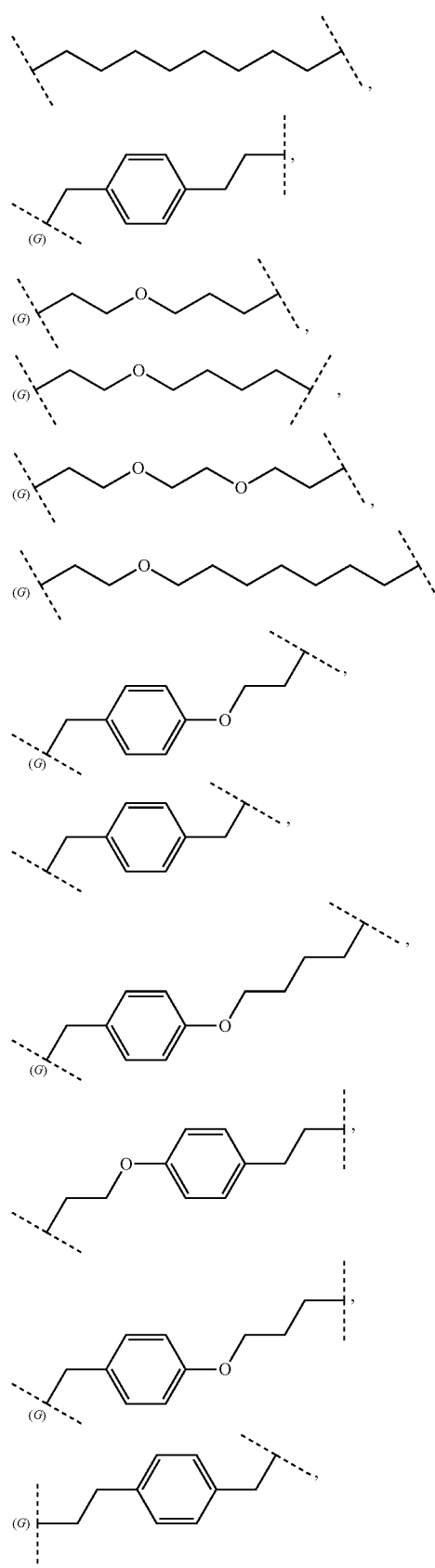

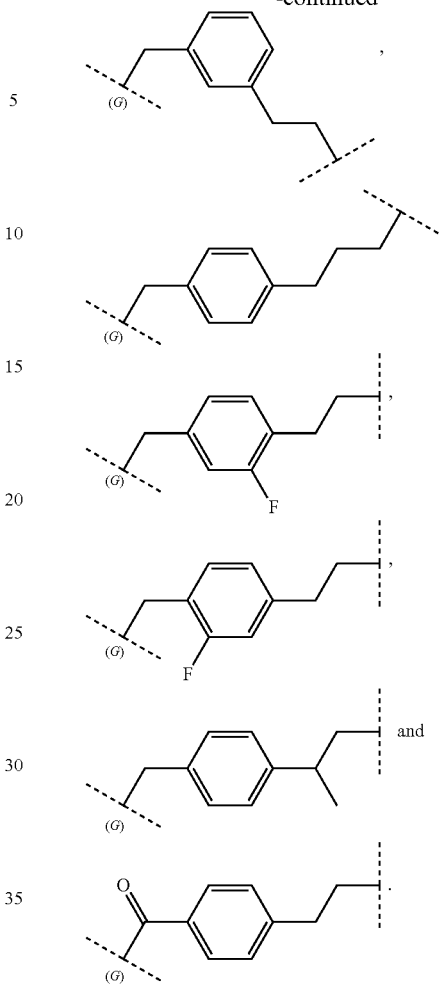

All the above-mentioned structural aspects [A1] to [A3], [B1] to [B9], [C1] and [D1] and [D2] are preferred embodiments of the corresponding aspects [A0], [B0], [C0] and [D0], respectively. The structural aspects [A0] to [A3], [B0] to [B9], [C0] and [C1] and [D0] to [D2] relating to different molecular parts of the compounds (I) according to the invention may be combined with one another as desired in combinations [A][B][C][D] to obtain preferred compounds (I). Each combination [A][B][C][D] represents and defines individual embodiments or generic subsets of compounds (I) according to the invention.

Preferred embodiments of the invention with structure (I) are example compounds 1-1 to 1-18 and any subset thereof.

All synthetic intermediates generically defined as well is specifically disclosed herein and their salts are also part of the invention.

All individual synthetic reaction steps as well as reaction sequences comprising these individual synthetic reaction steps, both generically defined or specifically disclosed herein, are also part of the invention.

The present invention further relates to hydrates, solvates, polymorphs, metabolites, derivatives, isomers and prodrugs of a compound of formula (I) (including all its embodiments).

The present invention further relates to a hydrate of a compound of formula (I) (including all its embodiments).

The present invention further relates to a solvate of a compound of formula (I) (including all its embodiments).

Compounds of formula (I) (including all its embodiments) which e.g. bear ester groups are potential prodrugs the ester being cleaved under physiological conditions and are also part of the invention.

The present invention further relates to a pharmaceutically acceptable salt of a compound of formula (I) (including all its embodiments).

The present invention further relates to a pharmaceutically acceptable salt of a compound of formula (I) (including all its embodiments) with an organic or organic acids or bases.

Medical Uses—Methods of Treatment

The present invention is directed to SMARCA2 and/or SMARCA4 degrading compounds, in particular compounds of formula (I) (including all its embodiments), which can be useful in the treatment and/or prevention of a disease and/or condition associated with or modulated by SMARCA2 and/or SMARCA4, especially wherein the degradation of SMARCA2 and/or SMARCA4 is of therapeutic benefit, including but not limited to the treatment and/or prevention of cancer.

In another aspect the invention relates to a compound of formula (I)—or a pharmaceutically acceptable salt thereof—for use as a medicament.

In another aspect the invention relates to a compound of formula (I)—or a pharmaceutically acceptable salt thereof—for use in a method of treatment of the human or animal body.

In another aspect the invention relates to a SMARCA2 and/or SMARCA4 degrading compound, in particular a compound of formula (I)—or a pharmaceutically acceptable salt thereof—for use in the treatment and/or prevention of a disease and/or condition wherein the degradation of SMARCA2 and/or SMARCA4 is of therapeutic benefit, including but not limited to the treatment and/or prevention of cancer.

In another aspect the invention relates to a compound of formula (I)—or a pharmaceutically acceptable salt thereof—for use in the treatment and/or prevention of cancer.

In another aspect the invention relates to a compound of formula (I)—or a pharmaceutically acceptable salt thereof—for use in a method of treatment and/or prevention of cancer in the human or animal body.

In another aspect the invention relates to a compound of formula (I)—or a pharmaceutically acceptable salt thereof—for use in a method of treatment and/or prevention of cancer in the human or animal body.

In another aspect the invention relates to the use of a compound of formula (I)—or a pharmaceutically acceptable salt thereof—for preparing a pharmaceutical composition for the treatment and/or prevention of cancer.

In another aspect the invention relates to the use of a compound of formula (I)—or a pharmaceutically acceptable salt thereof—as hereinbefore defined for the treatment.

In another aspect the invention relates to a method for the treatment and/or prevention of a disease and/or condition wherein degradation of SMARCA2 and/or SMARCA4 is of therapeutic benefit comprising administering a therapeutically effective amount of a SMARCA2 and/or SMARCA4 degrading compound, in particular a compound of formula (I)—or a pharmaceutically acceptable salt thereof—to a human being.

In another aspect the invention relates to a method for the treatment and/or prevention of cancer comprising administering a therapeutically effective amount of a compound of formula (I)—or a pharmaceutically acceptable salt thereof—to a human being.

In another aspect the invention relates to a method for the treatment as hereinbefore and hereinafter defined.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas, gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NL-PHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas.

In another aspect the disease/condition/cancer to be treated/prevented with the SMARCA2 and/or SMARCA4 degrading compound is a disease/condition/cancer defined as exhibiting one or more of the following molecular features:

Impaired or loss of function of BAF complex subunits, including but not limited to SMARCB1, ARID1A, ARID1B, ARID2, PBRM1, SMARCA2 and SMARCA4 due either to inactivating mutations in these genes or loss of their expression through alternative mechanisms other than inactivating mutations;

Impaired or loss of SMARCA2 or SMARCA4 function due either to inactivating mutations in the SMARCA2 or SMARCA4 genes or loss of SMARCA2 or SMARCA4 expression through alternative mechanisms other than inactivating mutations; Inactivating mutations affecting SMARCA2 or SMARCA4 function include nonsense or insertion/deletion (e.g. frameshift) mutations that result in loss of protein or activity; and/or missense mutations that inactivate the function of the protein; and/or changes in gene expression levels; and/or changes in protein levels; and/or changes in protein function.

In another aspect the cancer to be treated/prevented with the SMARCA2 and/or SMARCA4 degrading compound is a cancer found to harbor mutations in either SMARCA2 or SMARCA4, and/or to show loss of either SMARCA2 or SMARCA4 expression, and/or to show loss or impairment of either SMARCA2 or SMARCA4 protein function, and/or to show changes in either SMARCA2 or SMARCA4 gene expression or either SMARCA2 or SMARCA4 protein levels, while at the same time, in each case, retaining a functional copy of either SMARCA2 or SMARCA4 protein and/or exhibiting proper expression of either SMARCA2 or SMARCA4.

Any disease/condition/cancer, medical use, use, method of treatment and/or prevention as disclosed or defined herein (including molecular/genetic features) may be treated/performed with any compound of formula (I) as disclosed or defined herein (including all individual embodiments or generic subsets of compounds (I)).

Combination Therapy

In another aspect the invention relates to a compound of formula (I)—or a pharmaceutically acceptable salt thereof—for use as hereinbefore defined wherein said compound is administered before, after or together with at least one other pharmacologically active substance.

In another aspect the invention relates to a compound of formula (I)—or a pharmaceutically acceptable salt thereof—for use as hereinbefore defined, wherein said compound is administered in combination with at least one other pharmacologically active substance.

In another aspect the invention relates to a pharmacologically active substance prepared for being administered before, after or together with a compound of formula (I)—or a pharmaceutically acceptable salt thereof—for use as hereinbefore defined for the use of the compound of formula (I).

In another aspect the invention relates to the use of a compound of formula (I)—or a pharmaceutically acceptable salt thereof—as hereinbefore defined wherein said compound is administered before, after or together with at least one other pharmacologically active substance.

In another aspect the invention relates to a method for the treatment and/or prevention as hereinbefore defined wherein the compound of formula (I)—or a pharmaceutically acceptable salt thereof—is administered before, after or together with at least one other pharmacologically active substance.

In another aspect the invention relates to a method for the treatment and/or prevention as hereinbefore defined wherein the compound of formula (I)—or a pharmaceutically acceptable salt thereof—is administered in combination with a therapeutically effective amount of at least one other pharmacologically active substance.

In another aspect the pharmacologically active substance to be used together/in combination with the compound of formula (I) (including all individual embodiments or generic subsets of compounds (I)), or in the medical uses, uses, methods of treatment and/or prevention as herein (above and below) defined can be selected from any one or more of the following (preferably there is only one additional pharmacologically active substance used in all these embodiments):

Hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-) growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect.

Pharmaceutical Compositions—Kits

In another aspect the invention relates to a pharmaceutical composition comprising at least one (preferably one) compound of formula (I)—or a pharmaceutically acceptable salt thereof—and one or more pharmaceutically acceptable excipient(s).

In another aspect the invention relates to a pharmaceutical preparation comprising a compound of formula (I)—or a pharmaceutically acceptable salt thereof—and at least one (preferably one) other pharmacologically active substance.

In another aspect the invention relates to a kit comprising
a first pharmaceutical composition or dosage form comprising a compound of formula (I) and, optionally, one or more pharmaceutically acceptable carriers, excipients and/or vehicles, and
at least a second pharmaceutical composition or dosage form comprising another pharmacologically active substance and, optionally, one or more pharmaceutically acceptable carriers, excipients and/or vehicles.

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) of the invention with known excipients, for example inert diluents, carriers, disintegrants, adjuvants, surfactants, binders and/or lubricants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods:
For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 500 to 1500 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like HO, H$_2$N, (O)S, (O)$_2$S, NC (cyano), HOOC, F$_3$C or the like, the skilled artisan can see the radical attachment point(s) to the molecule from the free valences of the group itself.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$-CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl (neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$—, —CH$_2$CH$_3$ and —CH$_2$CH$_2$— or >CHCH$_3$ etc.

The term "$C_{1-4}$alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$-CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_3$))—, —(CH(CH(CH$_3$))$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or H$_2$N—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3- enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkyl, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl,1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms in common. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0] decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:
cyclohexyl and

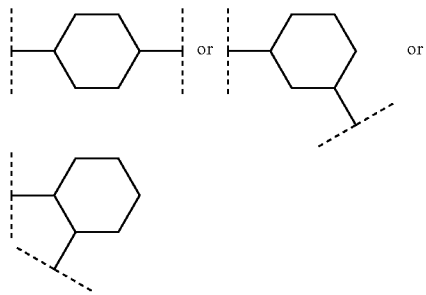

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:
cyclopentenyl and

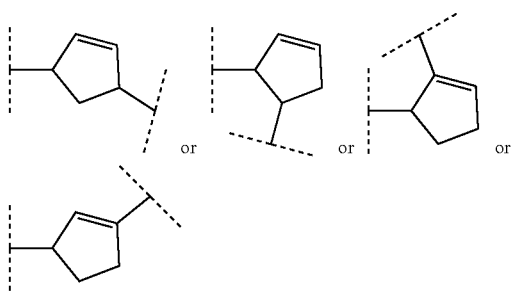

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:
phenyl and

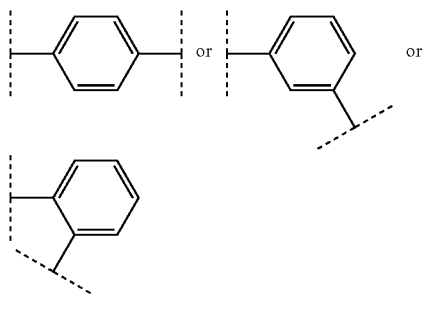

(o, m, p-phenylene),
naphthyl and

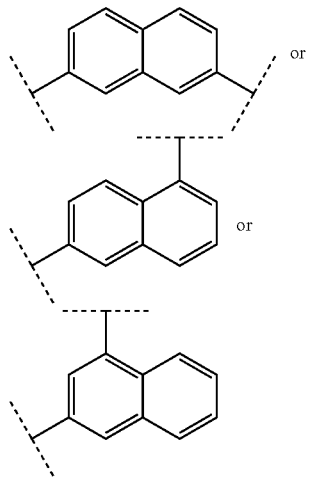

etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —$CH_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4,5]decyl etc.

Further examples are the structures illustrated below, which may be attached via each hydrogen-carrying atom (exchanged for hydrogen):

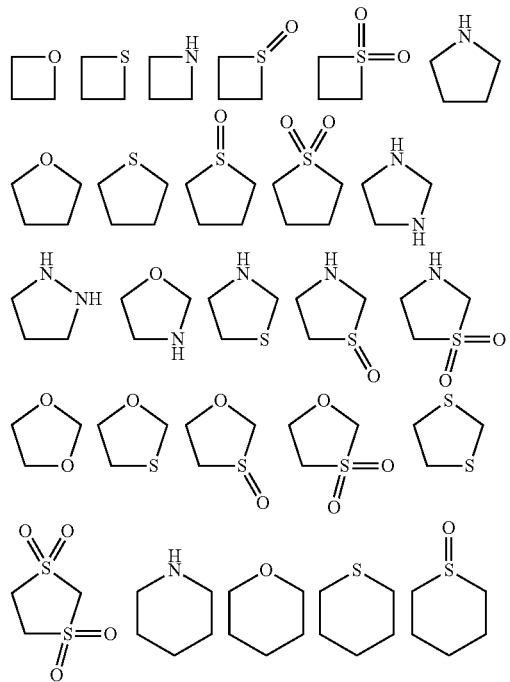

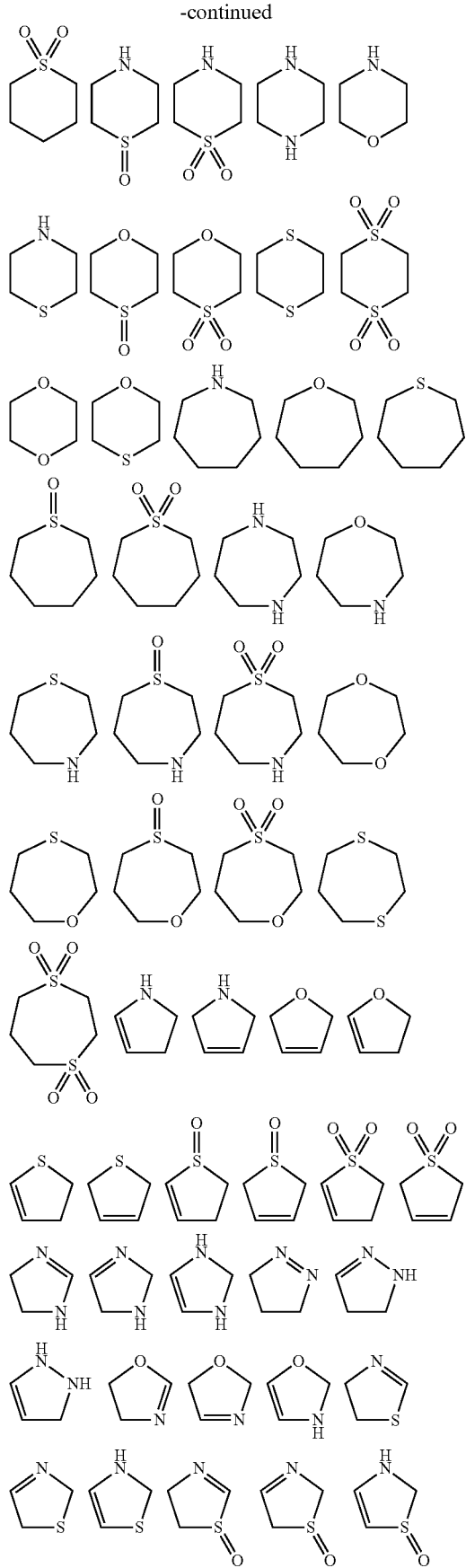
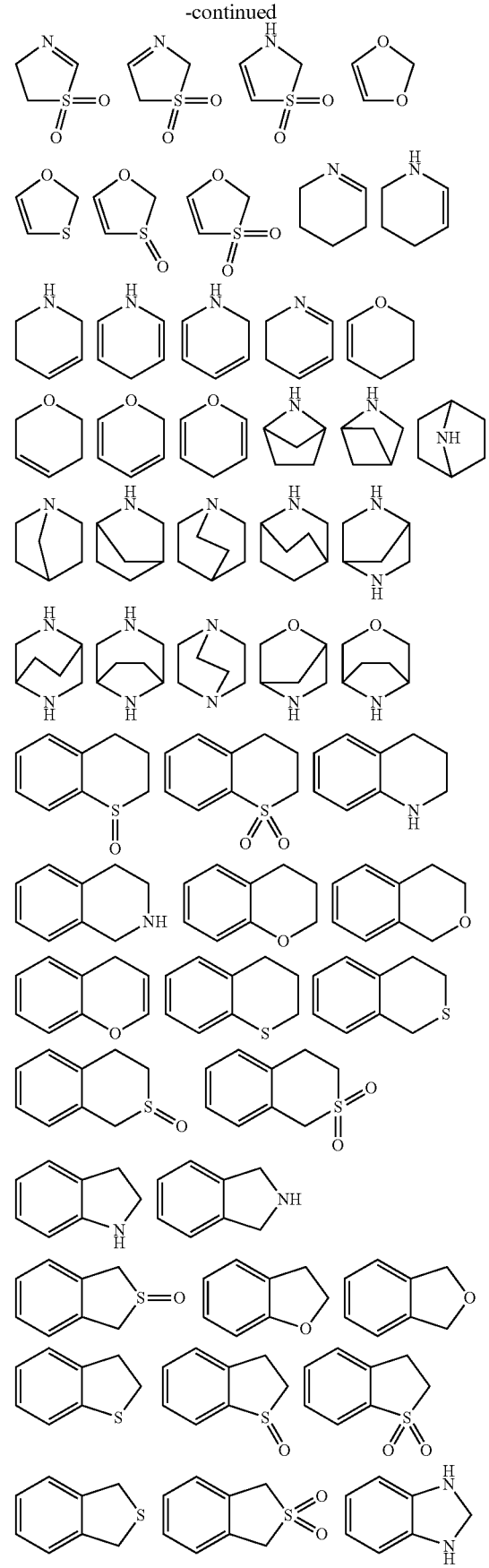

-continued

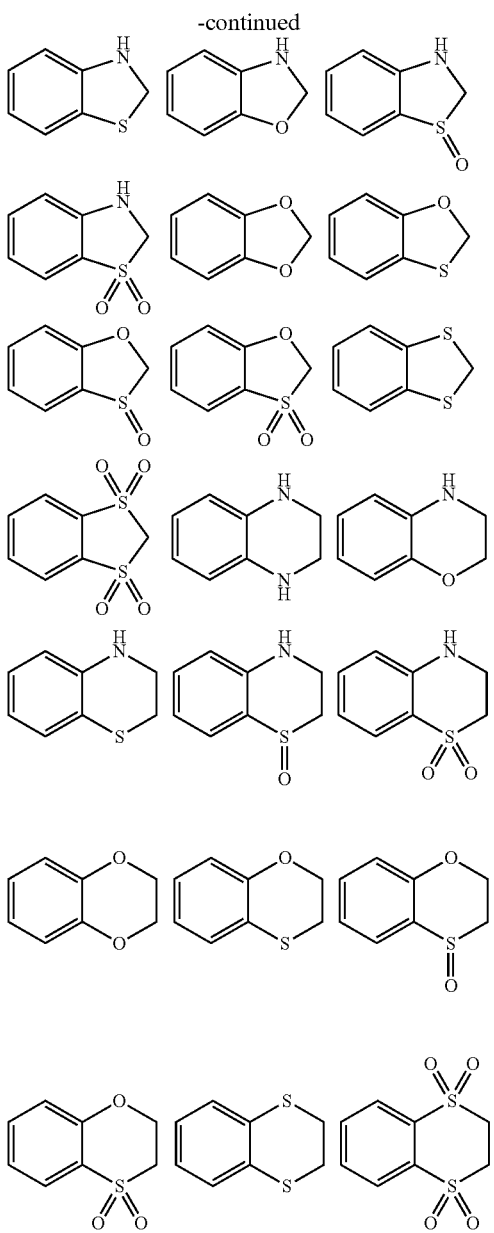

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

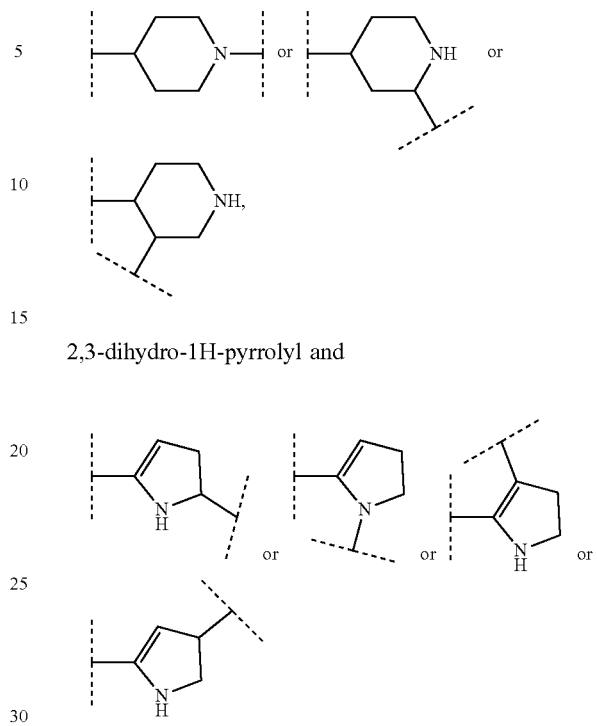

2,3-dihydro-1H-pyrrolyl and etc.

The above definition of heterocyclylene also applies if heterocyclylene is part of another (combined) group as for example in HO-heterocyclyleneamino or H$_2$N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

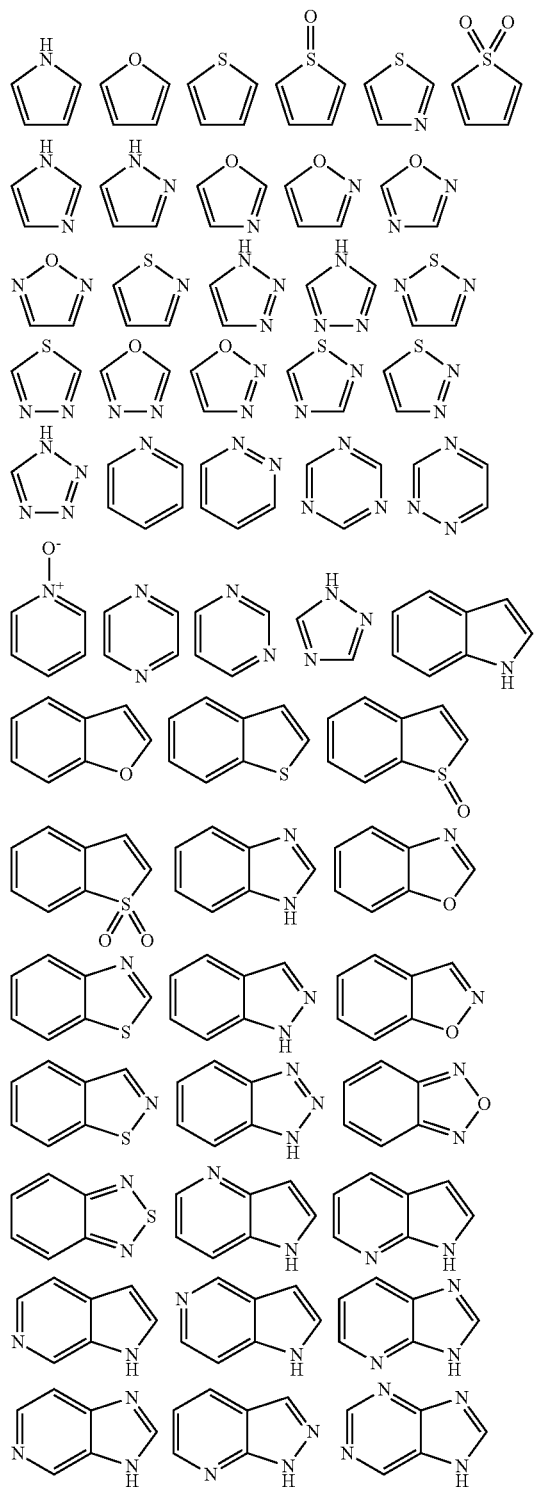

-continued

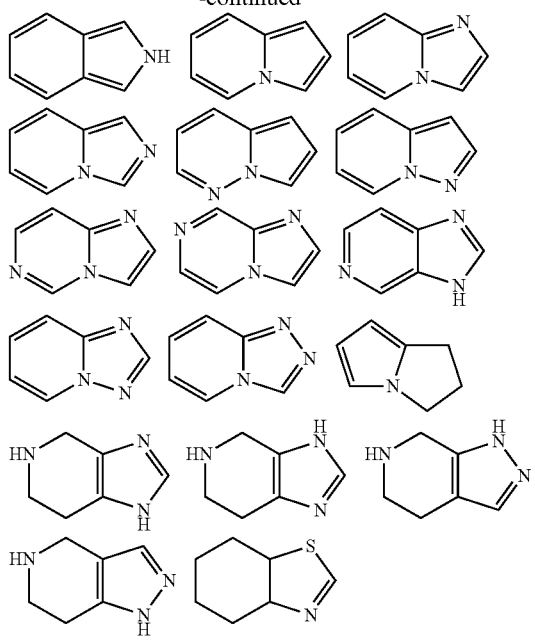

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:
pyrrolyl and

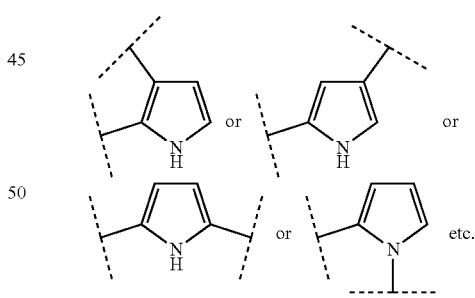

etc.

The above definition of heteroarylene also applies if heteroarylene is part of another (combined) group as for example in HO-heteroaryleneamino or H$_2$N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituents =O and =NR may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O group or =NR group only, one or two =O groups possible or, e.g., one =O group and one =NR group, each group replacing a free electron pair) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

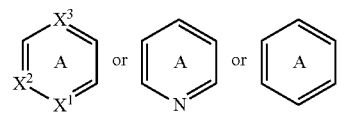

the letter A has the function of a ring designation in order to make it easier, for example, to indicate the attachment of the ring in question to other rings.

For bivalent groups the corresponding binding partners are indicated in brackets where necessary for clarification purposes, as in the following representations:

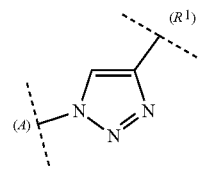

or (R$^2$)—C(O)NH— or (R$^2$)—NHC(O)—;

Groups or substituents are frequently selected from among a number of alternative groups/substituents with a corresponding group designation (e.g. R$^a$, R$^b$ etc). If such a group is used repeatedly to define a compound according to the invention in different parts of the molecule then the various uses are to be regarded as totally independent of one another.

By a "therapeutically effective amount" for the purposes of this invention is meant a quantity of substance that is capable of obviating symptoms of illness or of preventing or alleviating these symptoms, or which prolong the survival of a treated patient.

A SMARCA2 and/or SMARCA4 degrading compound in the context of this invention is a compound, which binds to SMARCA2 and/or SMARCA4 and simultaneously to a ubiquitin ligase protein, thereby inducing ubiquitylation of SMARCA2 and/or SMARCA4 and subsequent degradation of SMARCA2 and/or SMARCA4 by the proteasome. More specifically the SMARCA2 and/or SMARCA4 degrading compound preferably binds to the bromodomain of SMARCA2 and/or SMARCA4. Suitable test systems to measure the binding of compounds according to the invention to SMARCA2 and/or SMARCA4 and their degradation are disclosed herein.

List of Abbreviations

| | |
|---|---|
| Ac | acetyl |
| ACN | acetonitrile |
| aq. | aquatic, aqueous |
| Bn | benzyl |
| Boc | tert-butyloxycarbonyl |
| Bu | butyl |
| c | concentration |
| Cbz | carboxybenzyl |
| $CH_2Cl_2$ | dichloro methane |
| d | day(s) |
| dba | dibenzylideneacetone |
| DBA | dibenzylidene acetone |
| DBU | 1,8-Diazabicyclo(5.4.0)undec-7-ene |
| DCE | dichloro ethane |
| DCM | dichloro methane |
| DEA | diethyl amine |
| DEAD | diethyl azodicarboxylate |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDTA | ethylenediaminetetraacetic acid |
| EGTA | ethyleneglycoltetraacetic acid |
| eq | equivalent(s) |
| equiv. | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| IBX | 2-iodoxy benzoic acid |
| i | iso |
| conc. | concentrated |
| LC | liquid chromatography |
| LiHMDS | lithium bis(trimethylsilyl)amide |
| Me | methyl |
| MeCN | acetonitrile |
| MeOH | methanol |
| min | minutes |
| MPLC | medium pressure liquid chromatography |
| MS | mass spectrometry |
| MTBE | methyl tert-butyl ether |
| NBS | N-bromo-succinimide |
| NIS | N-iodo-succinimide |

-continued

| | |
|---|---|
| NMM | N-methylmorpholine |
| NMP | N-methylpyrrolidone |
| NP | normal phase |
| n.a. | not available |
| Ph | phenyl |
| Pr | propyl |
| pTsOH | p-toluenesulfonic acid |
| Py | pyridine |
| rac | racemic |
| red. | reduction |
| Rf ($R_f$) | retention factor |
| RP | reversed phase |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethyl amine |
| temp. | temperature |
| tert | tertiary |
| Tf | triflate |
| TFA | trifluoroacetic acid |
| THF | tetrahydrofuran |
| TLC | thin layer chromatography |
| TMS | trimethylsilyl |
| $t_{Ret.}$ | retention time (HPLC) |
| TRIS | tris(hydroxymethyl)-aminomethane |
| UPLC | ultra performance liquid chromatography |
| UV | ultraviolet |
| wt | weight |

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software MarvinSketch (Chemaxon).

Phase Separators

Phase separation is carried out using Biotage ISOLUTE® phase separator columns.

Chromatography

The thin layer chromatography is carried out on ready-made silica gel 60 TLC plates on glass (with fluorescence indicator F-254) made by Merck.

The preparative high pressure chromatography (RP-HPLC) of the example compounds according to the invention is carried out on Agilent or Gilson systems with columns made by Waters (names: Sunfire™ Prep C18, OBD™ 10 μm, 50×150 mm or Sunfire™ Prep 018 OBD™ 5 μm, 30×50 mm or Sunfire™ Prep C18, OBD 10 μm, 30×100 mm or XBridge™ Prep C18, OBD™ 10 μm, 50×150 mm or XBridge™ Prep C18, OBD™ 5 μm, 30×150 mm or XBridge™ Prep C18, OBD™ 5 μm, 30×50 mm) and YMC (names: Actus-Triart Prep C18, 5 μm, 30×50 mm).

Different gradients of MeCN/$H_2O$ are used to elute the compounds, while for Agilent systems 5% acidic modifier (20 mL HCOOH to 1 L $H_2O$/acetonitrile (1/1)) is added to the water (acidic conditions). For Gilson systems 0.1% HCOOH is added to the water.

For the chromatography under basic conditions for Agilent systems MeCN/H$_2$O gradients are used as well, while the water is made alkaline by addition of 5% basic modifier (50 g NH$_4$HCO$_3$+50 mL NH$_3$ (25% in H$_2$O) to 1 L with H$_2$O). For Gilson systems the water is made alkaline as follows: 5 mL NH$_4$HCO$_3$ solution (158 g in 1 L H$_2$O) and 2 mL NH$_3$ (28% in H$_2$O) are replenished to 1 L with H$_2$O.

If other gradients or eluents were used it's described directly in the respective example.

HPLC-mass spectroscopy/UV-spectrometry of intermediates and examples 1-1 to 1-18 The retention times/MS-ESI$^+$ for characterizing the intermediates and final compounds are produced using different HPLC-MS machines (high performance liquid chromatography with mass detector). Compounds that elute with the injection peak are given the retention time $t_{Ret.}$=0.00 min. The exact methods are as follows:

Method A
  HPLC-MS: Waters UPLC-Xevo TQS Triple quad
  Column: Aquity BEH C18 2.1×50 mm, 1.7 µm
  Eluent: A: 0.07% formic acid in MeCN; B: 0.07% formic acid in water
  Spectrum: range: 230-400 nm
  Peak width: <0.01 min
  Injection: 5 µL standard injection
  Column temperature: 35° C.
  Flow: 0.60 mL/min
  Gradient: 0.00-0.30 min: 97% B
    0.30-2.70 min: 97%→2% B
    2.70-3.50 min: 2% B
    3.50-3.51 min: 2%→97% B Method B
  HPLC_MS: Waters Aquity-UPLC-SQ Detector-2
  Column: AQUITY UPLC BEH C18 2.1×50 mm, 1.7 µm
  Eluent: A: 0.05% formic acid in MeCN; B: 0.05% formic acid in water
  Spectrum: range: 230-400 nm
  Peak width: <0.01 min
  Injection: 5 µL standard injection
  Column temperature: 35° C.
  Flow: 0.60 mL/min
  Gradient: 0.00-0.30 min: 97% B
    0.30-2.20 min: 97%→2% B
    2.20-3.30 min: 2%→4.5% B
    3.30-4.50 min: 4.5% B
    4.50-4.51 min: 4.5%→97% B Method C
  HPLC: Agilent 1200 HPLC with diode array detector
  MS: Agilent 6130 ESI Mass Spectrometer
  MSD signal settings: ESI positive, 100-1000 m/z
  Column: Waters XBridge C18 column, 2.1×50 mm, 3.5 µm particle size
  Eluent: A: 0.1% formic acid in H$_2$O; B: 0.1% formic acid in CH$_3$CN
  Detection signal: 254 nm, reference off
  Spectrum range: 190-400 nm
  Peak width: <0.01 min
  Injection: 4.0 µL standard injection
  Column temperature: 35° C.
  Flow: 0.7 mL/min
  Gradient: 5-95% B, 3 minutes method Method D
  HPLC: Agilent 1100 Series
  MS: Bruker Microtof
  MSD signal settings: ESI positive 100-1200 m/z
  Column: Waters XBridge C18 column, 2.1×50 mm, 3.5 µm particle size
  Eluent: A: 0.1% ammonia in H$_2$O; B: 0.1% ammonia in CH$_3$CN
  Detection signal: 254 nm, reference off
  Spectrum range: 190-400 nm
  Peak width: <0.01 min
  Injection: 3.0 µL standard injection
  Column temperature: 35° C.
  Flow: 0.6 mL/min
  Gradient: 5-95% B, 8 minutes method Method E
  HPLC: Agilent 1290 system
  MS: 1200 Series LC/MSD (API-ES+/−3000 V, Quadrupol, G6140)
  MSD signal settings: Scan pos/neg 120-900 m/z
  Column: Waters, Xbridge C18, 2.5 µm, 2.1×20 mm column
  Eluent: A: 20 mM NH$_4$HCO$_3$/NH$_3$ pH 9; B: acetonitrile MS grade
  Detection signal: 315 nm (bandwidth 170 nm, reference off)
  Spectrum: range: 230-400 nm
  Peak width: <0.01 min
  Injection: 5 µL standard injection
  Column temperature: 60° C.
  Flow: 1.00 mL/min
  Gradient: 0.00-1.50 min: 10%→95% B
    1.50-2.00 min: 95% B
    2.00-2.10 min: 95%→10% B Method F
  HPLC: Agilent 1100/1200 system
  MS: 1200 Series LC/MSD (MM-ES*APICI+/−3000 V, Quadrupol, G6130)
  MSD signal settings: Scan pos/neg 150-1350 m/z
  Column: Waters, XBridge C18, 2.5 µm, 2.1×30 mm
  Eluent: A: 5 mM NH$_4$HCO$_3$/18 mM NH$_3$ (pH=9.2); B: MeCN HPLC grade
  Detection signal: 254 nm (bandwidth 8, reference off)
  Spectrum: range: 190-400 nm
  Peak width: 0.0025 min (0.05 s)
  Injection: 0.5 µL standard injection
  Column temperature: 45° C.
  Flow: 1.40 mL/min
  Gradient: 0.00-1.00 min: 15%→95% B
    1.00-1.30 min: 95% B
    Stop time: 1.3 min The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

A. General Preparation Methods for Compounds (I) According to the Invention

A.1 General Preparation Strategies for Tripartite Compounds TB-LK-LB

All compounds (I) according to the invention are tripartite compounds TB-LK-LB consisting of a target binder (TB), a linker (LK) and a ligase binder (LB). The building block introducing the target binder should possess a suitable functional group that can be covalently linked. The building block introducing the linker usually bears orthogonal or orthogonally protected functional groups at both ends, and the building block introducing the ligase binder also usually bears a suitable functional group that can be covalently linked. Generally, there are three different ways of preparation:

Option 1: In a first step one of the building blocks introducing TB or LK is chemically activated and covalently linked to the other to give building block TB-LK. In a second step one of the building blocks TB-LK or LB is chemically activated and covalently linked to the other to give TB-LK-LB.

Option 2: In a first step one of the building blocks introducing LB or LK is chemically activated and covalently linked to the other to give building block LK-LB. In a second step one of the building blocks TB or LK-LB is chemically activated and covalently linked to the other to give TB-LK-LB.

Option 3: Building block TB is first covalently connected to a building block LK' which only introduces one part of the final linker LK to give TB-LK' and LB is covalently connected to a building block LK' which introduces the second part of the final linker LK to give LK"-LB.

In a second step the covalent connection between TB-LK' and LK"-LB connecting LK' and LK" is formed to give TB-LK-LB.

A.2 General Approach for the Synthesis of Compounds (I) According to Option 2

Compounds (I) according to the invention can be prepared as described schematically under section A.1 option 2 starting from a suitable E3 ligase binder building block (LB), a linker building block (LK) and a suitable SMARCA bromodomain binder building block (TB).

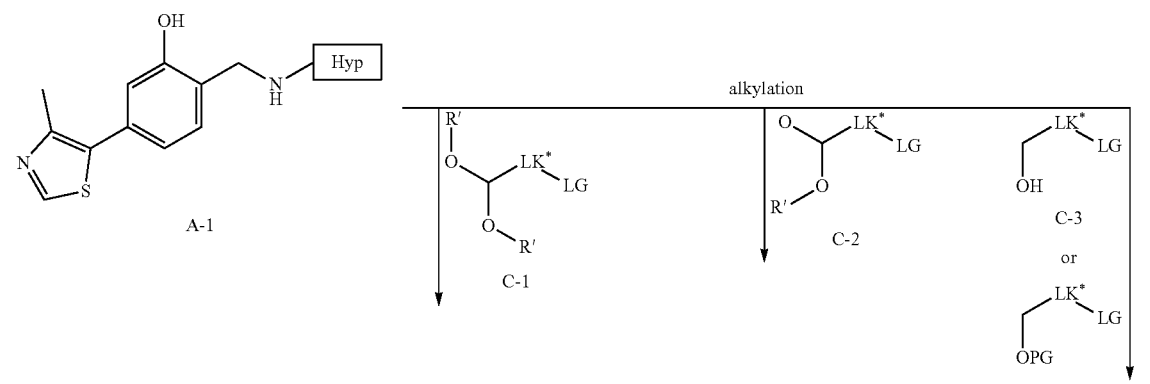

Scheme 1: General synthesis routes to compounds (I) starting from ligase binder building block A-1 (option 2)

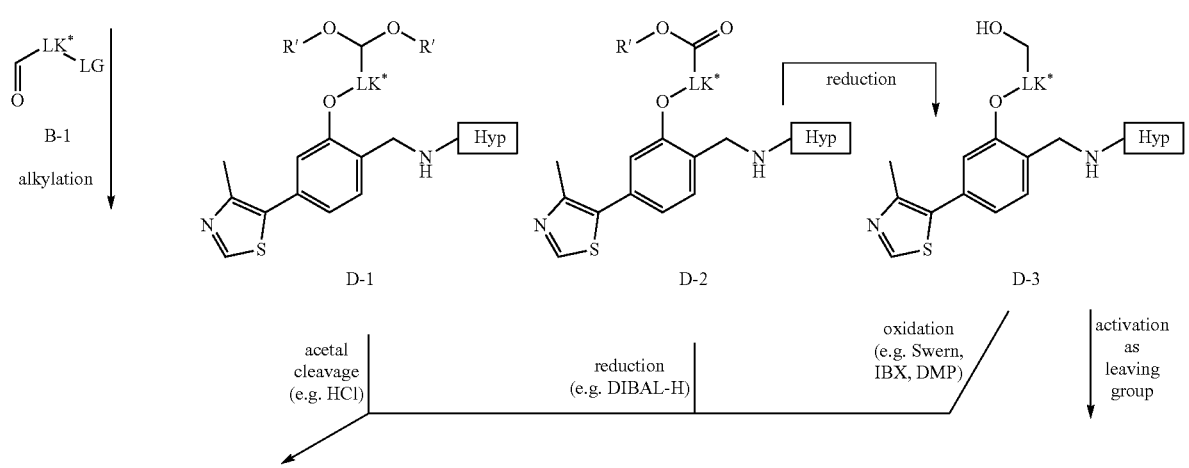

-continued

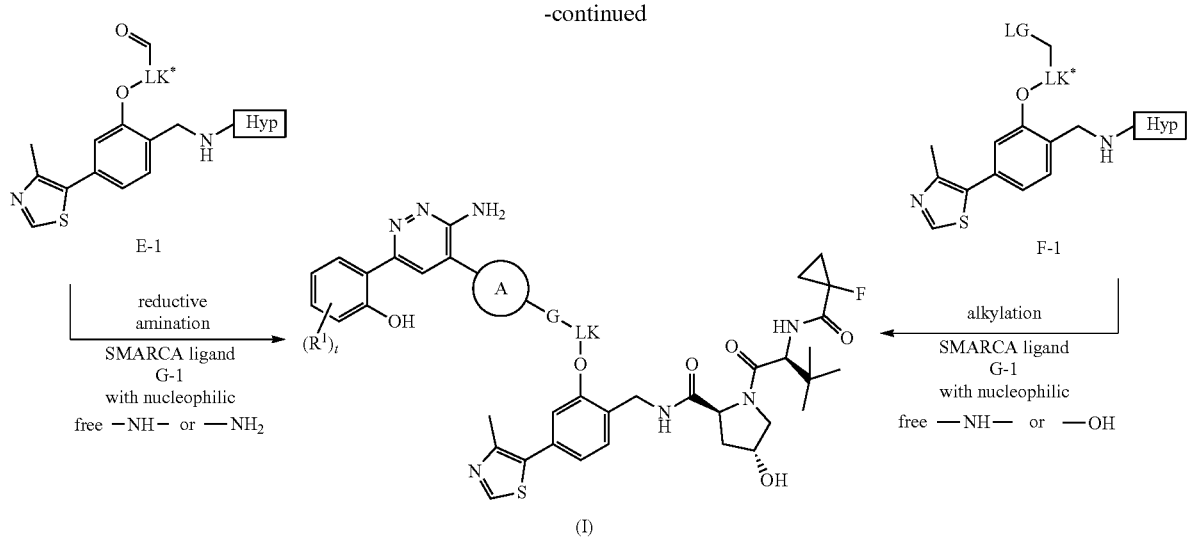

LG = e.g. Cl, Br, I, —OMs, —OTs, —OTf
R' = Me, Et or cyclic acetal
R" = Me, Et, tBu
LK = (here:) —CH$_2$—LK*—

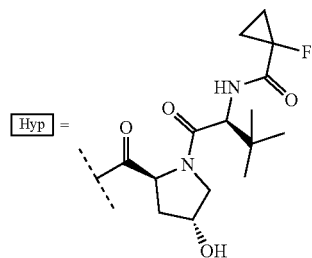

As outlined in scheme 1 compounds (I) according to the invention can be prepared from suitable building blocks A-1 (VHL ligase binding motifs→"LB") and G-1 (SMARCA binding motifs→"TB") which can be prepared according to published procedures or can be synthesized as described below.

Phenols A-1 can be alkylated with bifunctional compounds B-1 which carry a leaving group (e.g. halogen, activated alcohol) on one end and an aldehyde functionality on the other end using a suitable base and obtaining intermediates E-1 (→"LK-LB"). Alternatively, such intermediates E-1 can be synthesized by alkylating phenols A-1 with bifunctional compounds C-1, C-2 or C-3 which also carry a leaving group (e.g. halogen, activated alcohol) on one end but an acetal (→C-1), ester (→C-2) or alcohol (optionally suitably protected) functionality (→C-3) on the other end using a suitable base. Intermediates D-1, D-2 and D-3 thus obtainable can then be transformed to intermediates E-1 by acetal cleavage, reduction or oxidation under various conditions, directly and also indirectly by first reducing intermediates D-2 to intermediates D-3 (with standard reagents such as LAH, NaBH$_4$, DiBALH amongst others) which are then oxidized.

Alternative desirable building blocks ("LK-LB") towards final compounds (I) are also intermediates F-1 which can be synthesized from intermediates D-3 by activating the hydroxy functionality to a leaving group, e.g. by using a halogenation protocol or a base and a suitable activation reagent. Suitably activated alcohols may be mesylates, tosylates or triflates, which can be prepared by standardized and well known methods using a base and the corresponding chlorides or anhydrides.

With intermediates E-1 or F-1 in hands there only remains the need to link SMARCA ligands G-1. This can either be achieved by reductive amination of E-1 with a —NH— or —NH$_2$ functionality of G-1 or by alkylation of F-1 with a —NH—, —NH$_2$ or —OH functionality of G-1 both yielding final compounds (I) according to the invention.

In case protected building blocks/intermediates are used, e.g. building blocks A-1, the protecting group can be removed at any step in the sequence by standard methods (not explicitly depicted in scheme 1).

Scheme 2: Synthetic route to LB building blocks A-1 (-OH unprotected and protected)

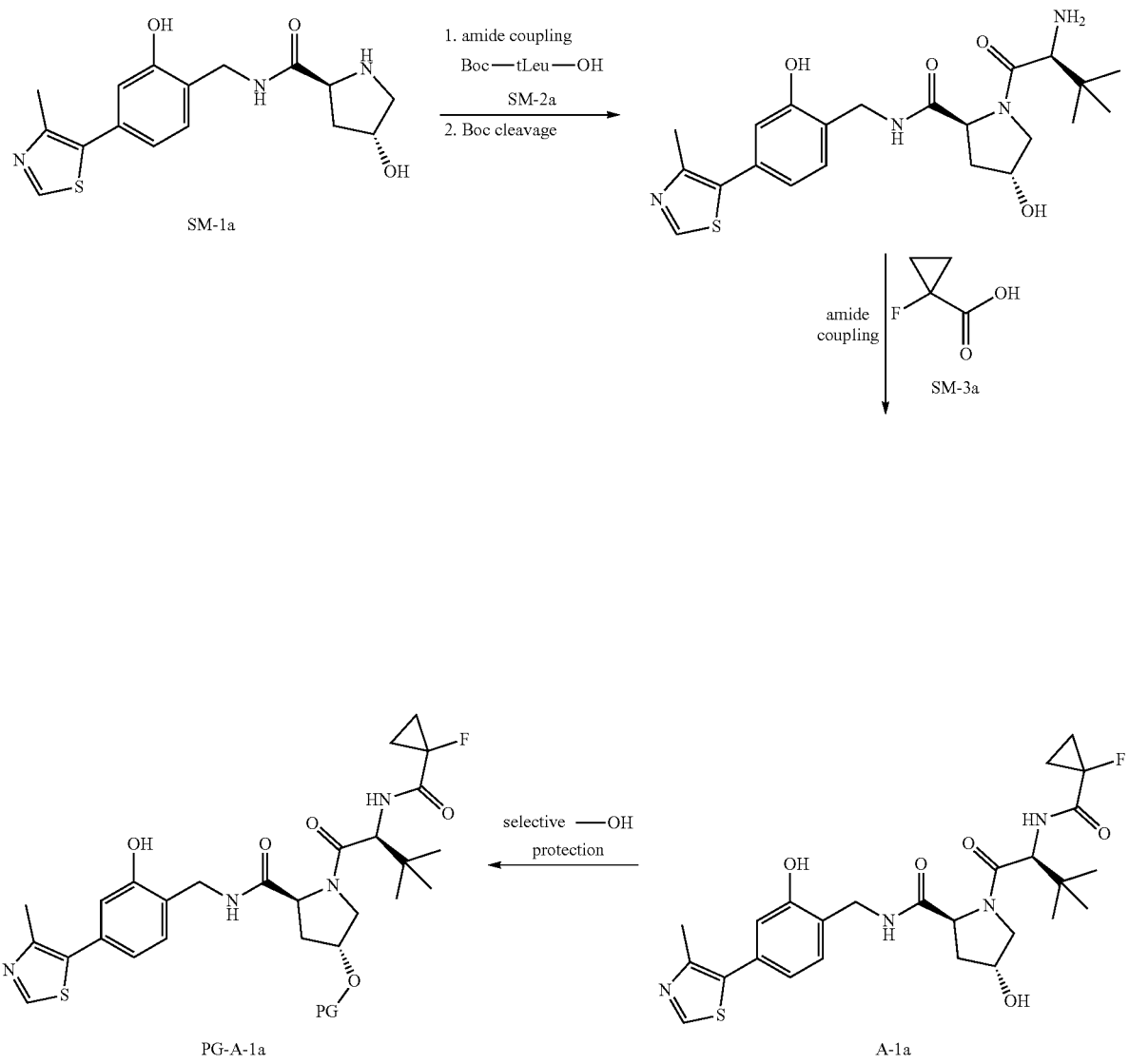

PG = Ac, TBDMS, TES, TIPS, Bn, etc.

Ligase binder building blocks A-1 (→"LB") used to prepare compounds (I) according to the invention can be synthesized as outlined in scheme 2 by consecutive amide coupling reactions starting from the 4-hydroxyproline derivative SM-1a which is described in the literature (D. Buckley et al., ACS Chemical Biology (2015), 10(8), 1831-1837). If necessary protecting groups such as acetyl or trialkyl-silyl can be selectively attached at the —OH function of the 4-hydroxyproline moiety of A-1 (→PG-A-1). Alternatively, the protecting group can also be introduced earlier during the synthesis of SM-1a by using a double protected 4-hydroxyproline derivative (i.e. —NH— and —OH protected) in the amide coupling with the benzylic biaryl amine.

The synthesis of SMARCA ligand building blocks G-1 is described in detail in the literature (e.g. in WO 2016/138114). The synthesis of bifunctional compounds B-1, C-1, C-2 and C-3 is described with the individual examples hereinbelow.

B. Synthetic Procedures
B.1 Synthesis of Building Blocks A-1
B.1.1 Experimental Procedures for the Synthesis of A-1a

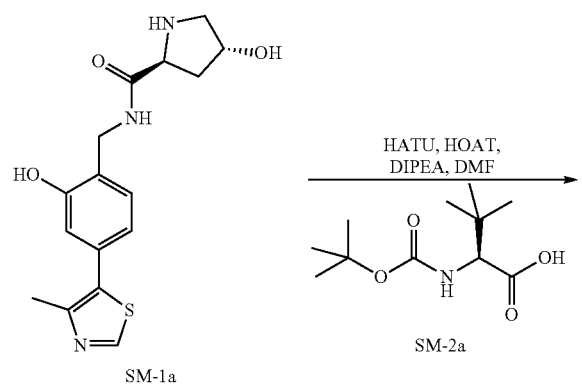

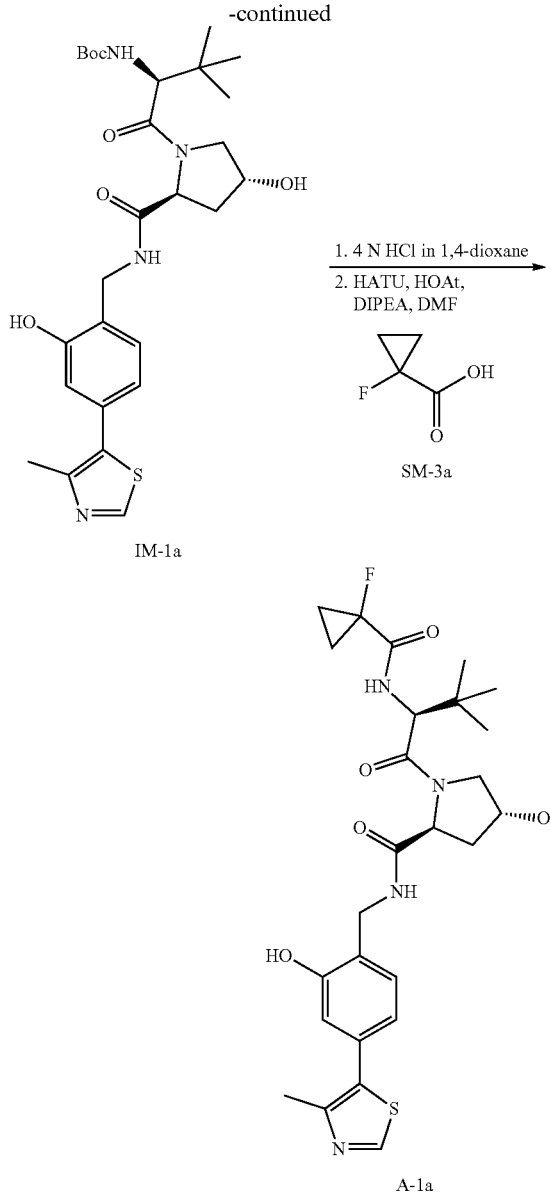

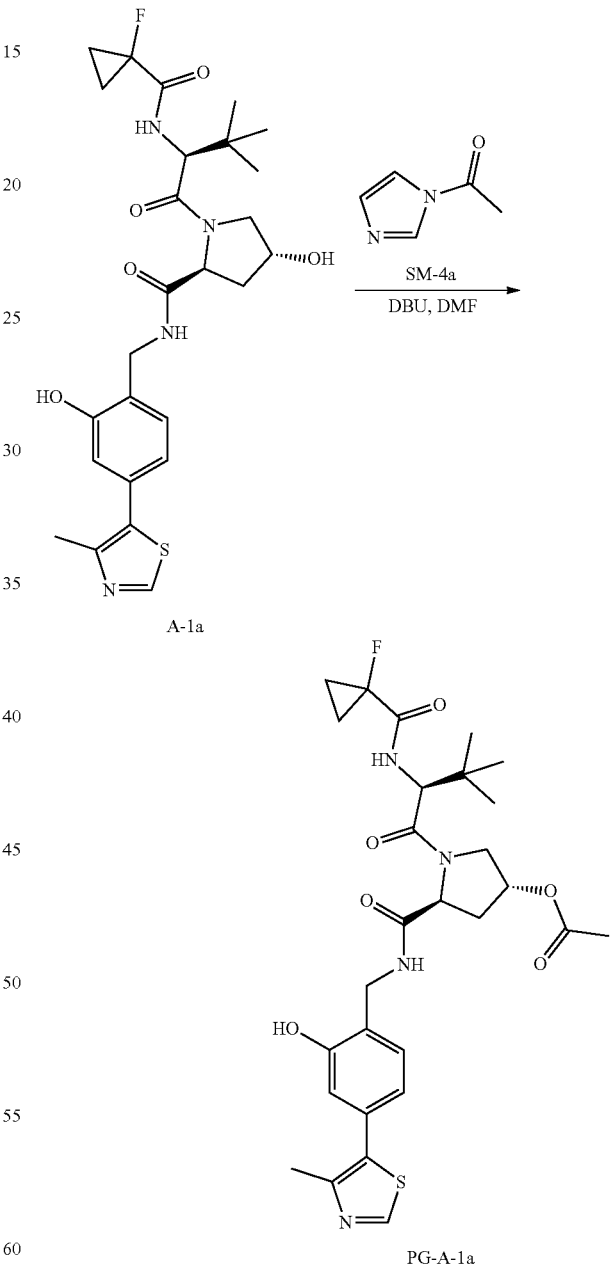

DIPEA (6.11 g; 47 mmol) and the mixture is stirred at rt for 30 min. Deprotected IM-1a (9.00 g; 20.2 mmol) dissolved in DMF is added and stirring is continued for 4 h at rt. The mixture is poured onto ice water, extracted with EtOAc (2×250 mL) and the layers are separated. The organic layer is washed with water (2×150 mL), dried over $Na_2SO_4$, concentrated in vacuo and the residue is purified by flash chromatography on $SiO_2$. The product containing fractions are evaporated to give pure A-1a (HPLC-MS: $t_{Ret.}$=1.88 min; MS $(M+H)^+$=534; method B).

B.1.2 Experimental Procedure for the Synthesis of PG-A-1a

To SM-2a (13.8 g; 59.6 mmol) in DMF (120 mL) is added HATU (22.8 g; 60.0 mmol), HOAt (8.16 g; 60.0 mmol) and DIPEA (18.2 g; 180 mmol). The reaction mixture is stirred for 30 min at rt, SM-1a (20.0 g; 60.0 mmol) (dissolved in DMF) is added and stirring is continued for 4 h. The mixture is poured onto ice water, extracted with EtOAc (2×500 mL) and the layers are separated. The organic layer is dried over $Na_2SO_4$, concentrated in vacuo and the residue is purified by flash chromatography on $SiO_2$. The product containing fractions are evaporated to give pure IM-1a (HPLC-MS: $t_{Ret.}$=1.77 min; MS $(M+H)^+$=547; method A).

To IM-1a thus obtained (10.0 g; 18.3 mmol) in DCM (90 mL) is added HCl (20 mL; 4 M in 1,4-dioxane) at rt and the mixture is stirred at rt for 4 h. The reaction mixture is concentrated in vacuo. The residue is washed with $Et_2O$ and dried to give the deprotected IM-1a (HPLC-MS: $t_{Ret.}$=1.51 min; MS $(M+H)^+$=448; method B), which is used without further purification.

To SM-3a (1.89 g; 18.2 mmol) in DMF (40 mL) is added HATU (7.66 g; 20.2 mmol), HOAt (2.74 g; 20.1 mmol) and To A-1a (544 mg; 1.02 mmol) and DBU (200 mg; 1.31 mmol) in DMF (5.0 mL) is added SM-4a (125 mg; 1.14 mmol) and the mixture is stirred at rt for 18 h. The reaction mixture is then partitioned between EtOAc and water and the layers are separated. The organic layer is dried over MgSO$_4$, filtered, concentrated in vacuo and the residue is purified by flash chromatography on SiO$_2$ (eluent: 0-10% MeOH in DCM). The product containing fractions are evaporated to give PG-A-1a (HPLC-MS: t$_{Ret.}$=1.51 min; MS (M+H)$^+$=575; method C).

B.2 Synthesis of Compounds (1)

B.2.1 Experimental Procedures for the Synthesis of Compound 1-1

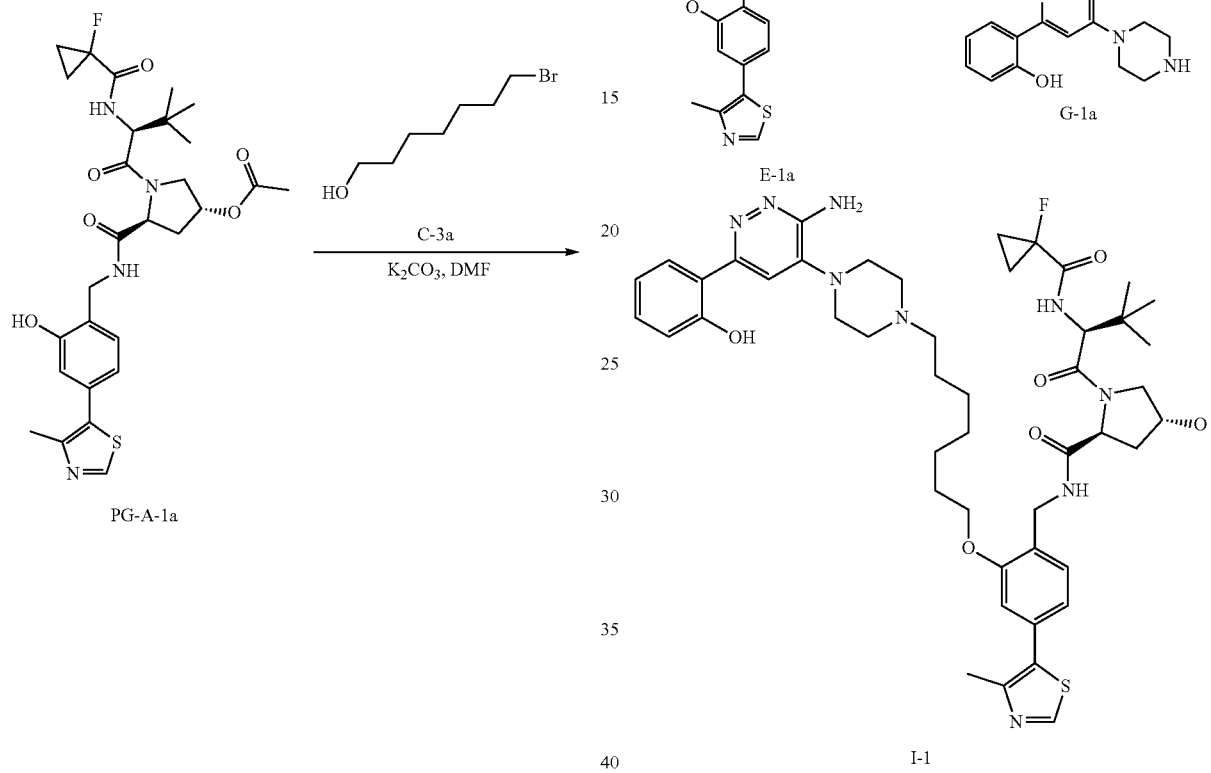

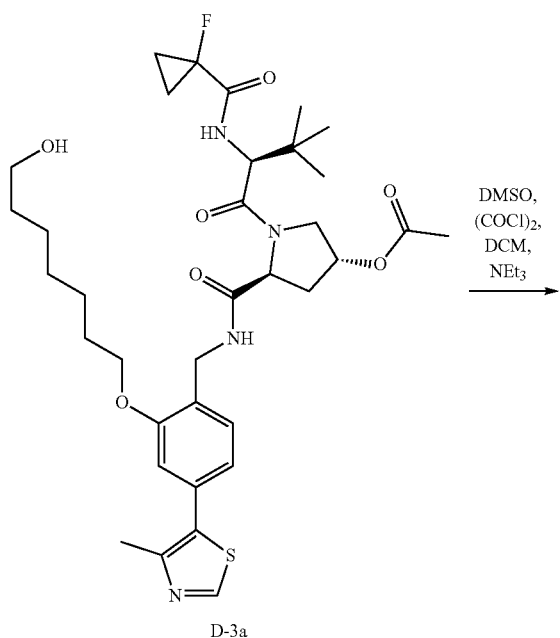

A mixture of PG-A-1a (80.0 mg; 139 µmol) and K$_2$CO$_3$ (22.0 mg; 159 µmol) in DMF (2.0 mL) is stirred at 90° C. for 45 min. C-3a (30.5 mg; 146 µmol) is added and stirring is continued at 90° C. for 5 h. After cooling to rt water (5.0 mL) and DCM (100 mL) are added and the mixture is passed through a phase separator. The filtrate is concentrated in vacuo and the residue is purified by flash chromatography on SiO$_2$ using 0-10% MeOH in DCM as eluent. The product containing fractions are evaporated to give D-3a (HPLC-MS: t$_{Ret.}$=1.73 min; MS (M+H)$^+$=703; method C).

To oxalyl chloride (15 µL, 170 µmol) in DCM (1.0 mL) at −78° C. is added DMSO (15 µL; 227 µmol) and the mixture is stirred at −78° C. for 15 min. D-3a (79.7 mg; 113 µmol) in DCM (1.0 mL) is added dropwise and the mixture is stirred at the same temperature for 1 h. NEt$_3$ (76 µL; 522 µmol) is added and the reaction mixture is allowed to warm up to rt and stirred for 1 h. Concentration in vacuo gives crude E-1a, which is directly added to a solution of G-1a (37.0 mg; 107 µmol) and NEt$_3$ (0.5 mL; 3.46 mmol) in DCE (3.0 mL) and DMSO (0.6 mL). NaBH(OAc)$_3$ (116 mg; 544 µmol) is added followed by MgSO$_4$ and the mixture is stirred for 18 h at rt. The reaction mixture is filtered and concentrated in vacuo. The residue is purified by preparative RP HPLC using 0-60% MeCN in 0.1% aq. HCO$_2$H as eluent. The product containing fractions are freeze dried to give the acetyl-protected I-1, which is dissolved in EtOH (3.0 mL) and NaOH (3.0 mL; 2 M in H₂O) is added and the mixture is stirred at 50° C. for 1 h. After cooling to rt the mixture is neutralized to pH 6 with 1 M hydrochloric acid, concentrated in vacuo and the residue is purified by preparative RP HPLC using 0-60% MeCN in 0.1% aq. HCO₂H as eluent. The product containing fractions are freeze dried to give 1-1 (HPLC-MS: $t_{Ret.}$=1.33 min; MS (M+H)⁺=914; method C).

B.2.2 Experimental Procedures for the Synthesis of Compound 1-2

Step 1: Synthesis of Bifunctional Compound C-1a

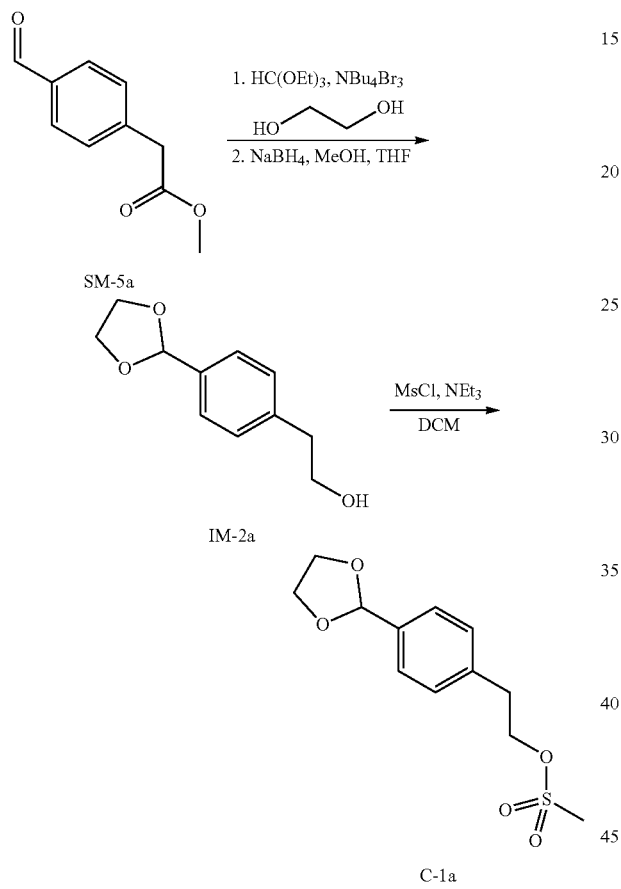

The product containing fractions are evaporated to give IM-2a which is used without further purification.

To IM-2a (170 mg; 875 µmol) and NEt₃ (600 µL; 4.15 mmol) in DCM (5.0 mL) is added methanesulfonyl chloride (121 mg; 1.06 mmol) at 0° C. and the mixture is stirred for 30 min. Saturated NaHCO₃ solution (3.0 mL) is added, the mixture is filtered through a phase separator, the filtrate is concentrated in vacuo and the residue is purified by flash chromatography on SiO₂ using 0-70% EtOAc in heptane. The product containing fractions are evaporated to give C-1a.

Step 2: Synthesis of Compound 1-2

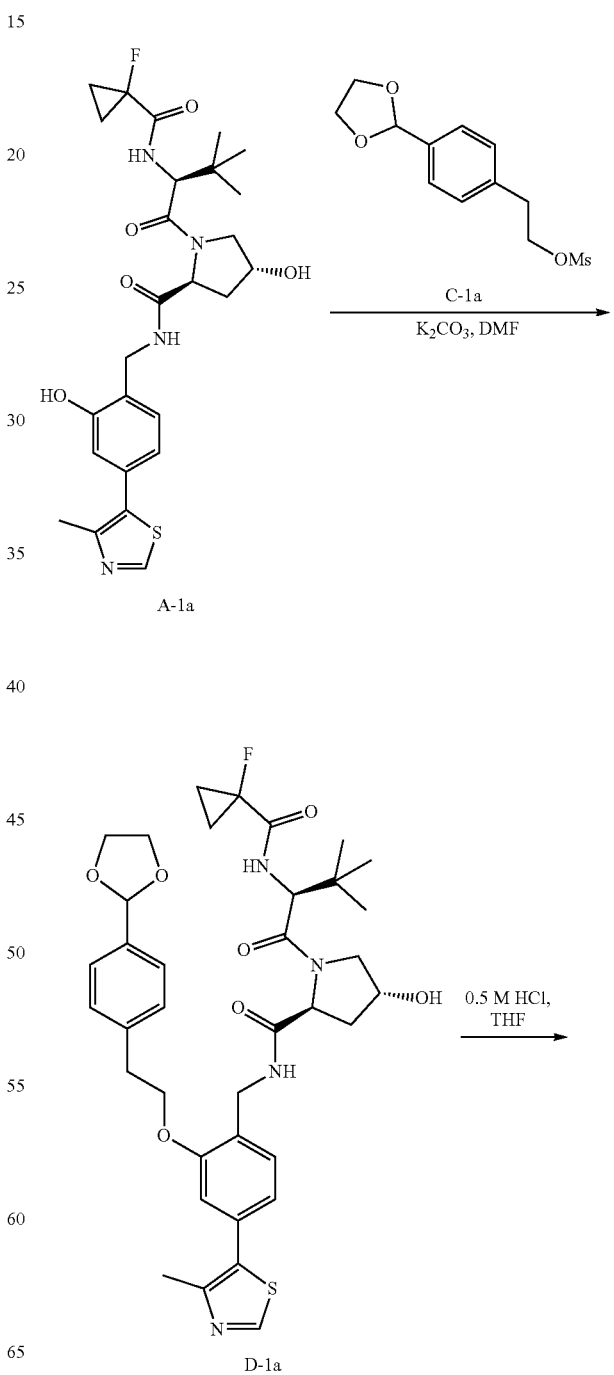

To a solution of SM-5a (500 mg; 2.81 mmol) in ethane-1,2-diol (670 µL; 11.9 mmol) and triethylorthoformate (520 µL) is added tetrabutylammonium tribromide (24.0 mg; 49.8 µmol) and the resulting mixture is stirred at rt in the dark for 1 h. The mixture is diluted with EtOAc (50 mL), washed with water (50 mL) and brine (50 mL). The organic layer is dried over MgSO₄, concentrated in vacuo and the residue is purified by flash chromatography on SiO₂ using 0-20% EtOAc in heptane as eluent. The product containing fractions are evaporated to give the acetal protected SM-5a.

To the acetal protected SM-5a in THF (2.0 mL) is added NaBH₄ (135 mg; 3.57 mmol) followed by MeOH (380 µL). The resulting mixture is stirred at rt for 18 h. The reaction mixture is quenched with 3 M aq. NaOH, neutralized to pH 6 with 1 M hydrochloric acid, diluted with DCM (100 mL) and filtered through a phase separator. The organic phase is concentrated in vacuo and the residue is purified by flash chromatography on SiO₂ using 0-70% EtOAc in heptane.

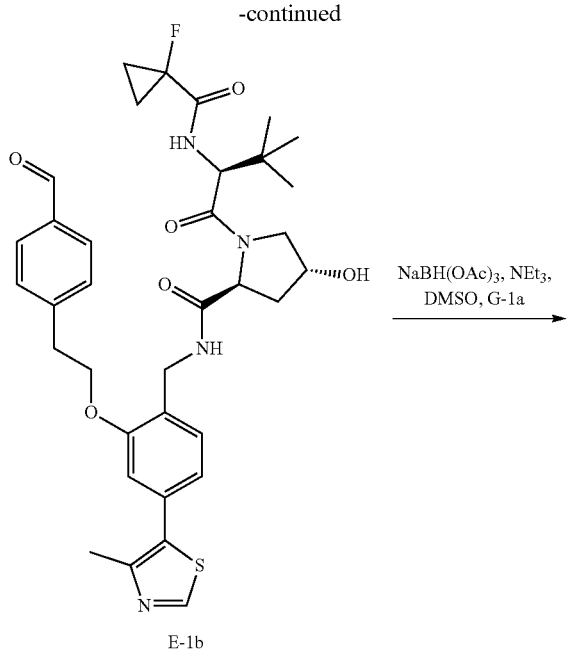

E-1b

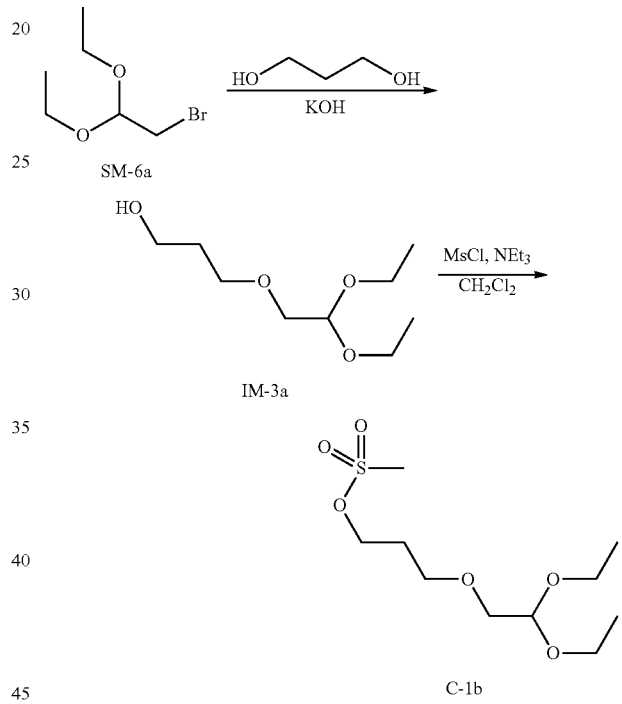

I-2

To a solution of A-1a (92.0 mg; 173 μmol) and K₂CO₃ (51.0 mg; 369 μmol) in DMF (2.0 mL) is added C-1a (84.0 mg; 308 μmol) and the resulting mixture is stirred at 70° C. for 18 h. After cooling to rt the mixture is diluted with water and DCM, filtered through a phase separator, the filtrate is concentrated in vacuo and the residue purified by flash chromatography on SiO₂ using 0-10% MeOH in DCM. The product containing fractions are evaporated to give D-1a (HPLC-MS: $t_{Ret.}$=1.61 min; MS (M+H)⁺=709; method C).

A solution of D-1a (71.7 mg; 101 μmol) in THF (500 μL) and 0.5 M aq. hydrochloric acid (500 μL) is stirred at 50° C. for 1 h. After cooling the reaction mixture is evaporated to give the crude aldehyde E-1b, which is taken up in in DCE (3.0 mL) and DMSO (600 μL). G-1a (37.0 mg; 107 μmol), NEt₃ (500 μL), MgSO₄ and NaBH(OAc)₃ (116 mg; 547 μmol) is added and the mixture is stirred at rt for 18 h. The reaction mixture is filtered, concentrated in vacuo and the residue is purified by preparative RP HPLC using 5-95% MeCN in 0.1% aq. HCOOH as eluent. The product containing fractions are freeze dried to give 1-2 (HPLC-MS: $t_{Ret.}$=1.28 min; MS (M+H)⁺=920; method C).

B.2.3 Experimental Procedures for the Synthesis of Compound 1-3

Step 1: Synthesis of Bifunctional Compound C-1b

Solid KOH (1.00 g; 17.8 mmol) is added to propane-1,3-diol (3.30 g; 43.4 mmol) and the mixture is stirred at 70° C. until completely dissolved. SM-6a (1.32 g; 6.70 mmol) is added and the mixture is stirred at 115° C. for 72 h. After cooling to rt the reaction mixture is diluted with water (5 mL) and DCM (100 mL), passed through a phase separator, concentrated in vacuo and the residue is purified by flash chromatography on SiO₂ using 0-5% MeOH in DCM as eluent. The product containing fractions are evaporated to give IM-3a.

To IM-3a (630 mg; 3.28 mmol) and NEt₃ (950 μL) in DCM (10 mL) is added methanesulfonyl chloride (1.29 g; 11.3 mmol) at 0° C. and the mixture is stirred for 30 min. Saturated aq. NaHCO₃ solution (3.0 mL) is added and the mixture is passed through a phase separator. The filtrate is concentrated in vacuo and the residue is purified by flash chromatography on SiO₂ using 0-50% EtOAc in heptane. The product containing fractions are evaporated to give C-1b ($R_f$=0.75; 5% MeOH in DCM, stain: KMnO₄).

Step 2: Synthesis of Compound 1-3

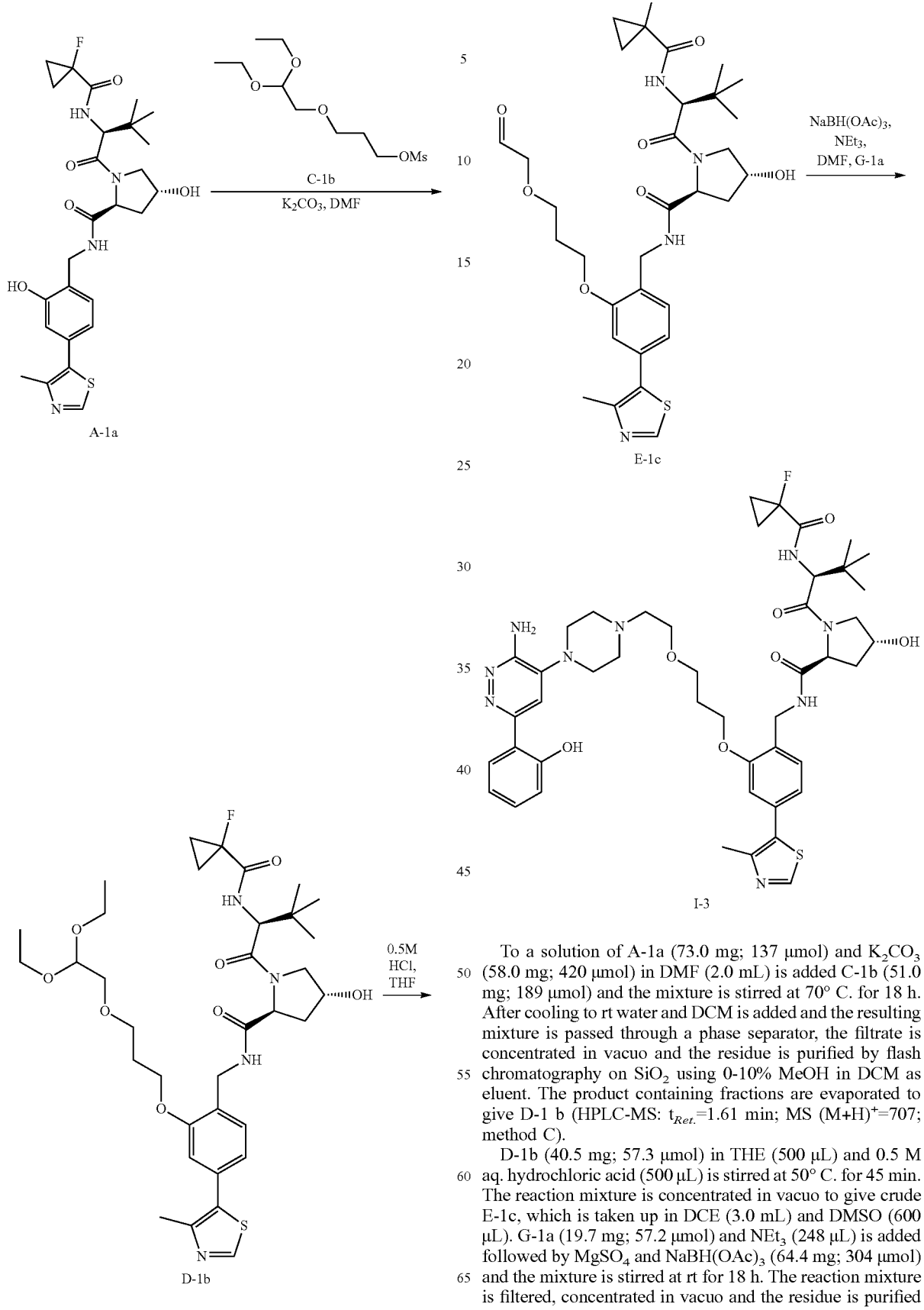

To a solution of A-1a (73.0 mg; 137 μmol) and K₂CO₃ (58.0 mg; 420 μmol) in DMF (2.0 mL) is added C-1b (51.0 mg; 189 μmol) and the mixture is stirred at 70° C. for 18 h. After cooling to rt water and DCM is added and the resulting mixture is passed through a phase separator, the filtrate is concentrated in vacuo and the residue is purified by flash chromatography on SiO₂ using 0-10% MeOH in DCM as eluent. The product containing fractions are evaporated to give D-1 b (HPLC-MS: $t_{Ret.}$=1.61 min; MS (M+H)⁺=707; method C).

D-1b (40.5 mg; 57.3 μmol) in THF (500 μL) and 0.5 M aq. hydrochloric acid (500 μL) is stirred at 50° C. for 45 min. The reaction mixture is concentrated in vacuo to give crude E-1c, which is taken up in DCE (3.0 mL) and DMSO (600 μL). G-1a (19.7 mg; 57.2 μmol) and NEt₃ (248 μL) is added followed by MgSO₄ and NaBH(OAc)₃ (64.4 mg; 304 μmol) and the mixture is stirred at rt for 18 h. The reaction mixture is filtered, concentrated in vacuo and the residue is purified by preparative RP HPLC using 5-95% MeCN in 0.1% aq.

HCOOH as eluent. The product containing fractions are freeze dried to give 1-3 (HPLC-MS: $t_{Ret.}$=1.20 min; MS (M+H)$^+$=888; method C).

B.2.4 Experimental Procedures for the Synthesis of Compound 1-4

Step 1: Synthesis of Bifunctional Compound C-1c

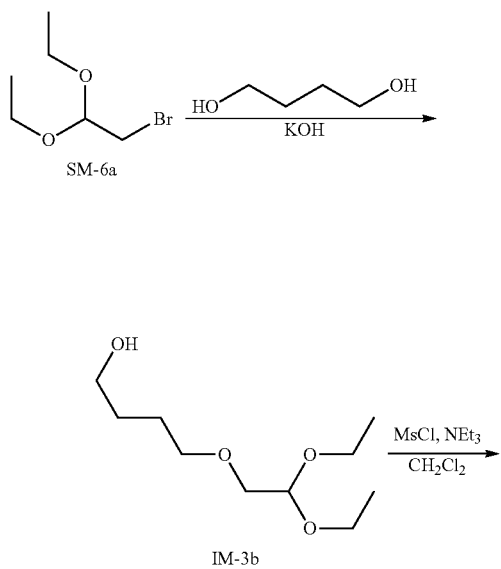

Solid KOH (1.00 g; 17.8 mmol) is added to butane-1,4-diol (4.00 g; 44.4 mmol) and the mixture is stirred at 70° C. until completely dissolved. SM-6a (1.32 g; 6.70 mmol) is added and the mixture is stirred at 115° C. for 72 h. After cooling to rt the reaction mixture is diluted with water (5 mL) and DCM (100 mL), passed through a phase separator, concentrated in vacuo and the residue is purified by flash chromatography on SiO$_2$ using 0-5% MeOH in DCM as eluent. The product containing fractions are evaporated to give IM-3b.

To IM-3b (879 mg; 4.26 mmol) and NEt$_3$ (750 μL) in DCM (20 mL) is added methanesulfonyl chloride (562 mg; 4.91 mmol) at 0° C. and the mixture is stirred for 30 min. Saturated aq. NaHCO$_3$ solution (3.0 mL) is added and the mixture is passed through a phase separator. The filtrate is concentrated in vacuo and the residue is purified by flash chromatography on SiO$_2$ using 0-70% EtOAc in heptane. The product containing fractions are evaporated to give C-1c.

Step 2: Synthesis of Compound 1-4

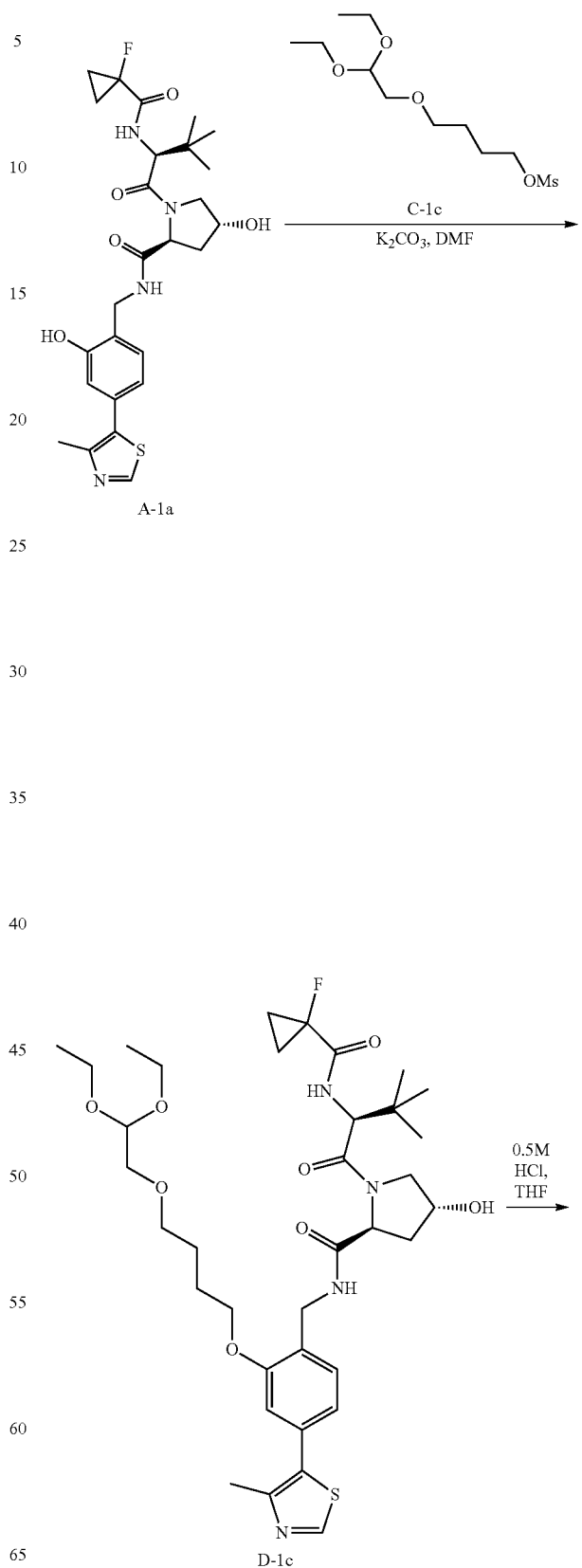

-continued

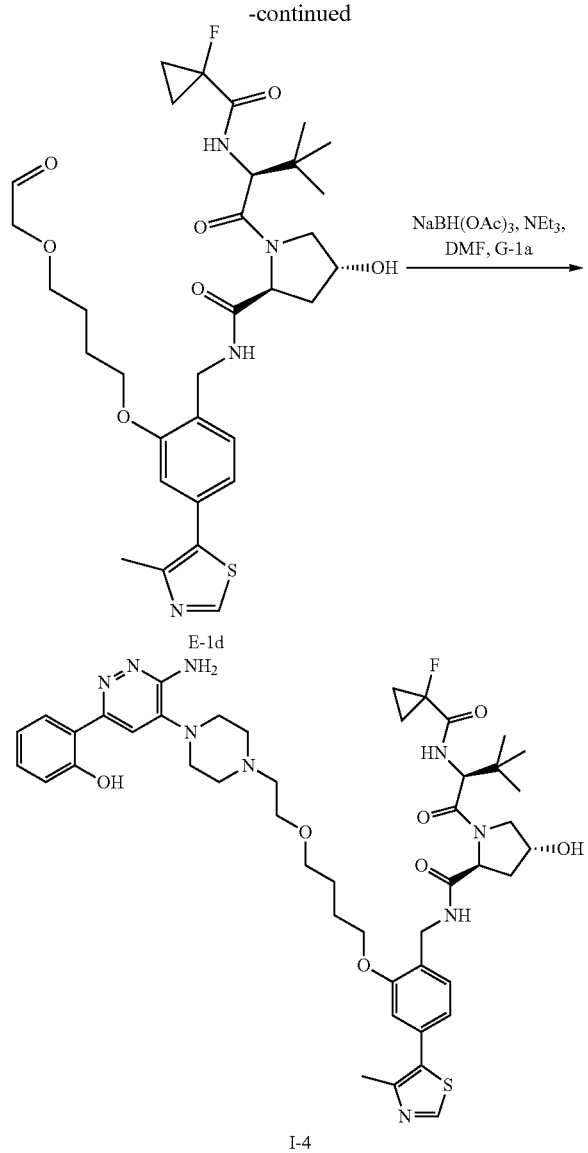

B.2.5 Experimental Procedures for the Synthesis of Compound 1-5

Step 1: Synthesis of Bifunctional Compound C-1d

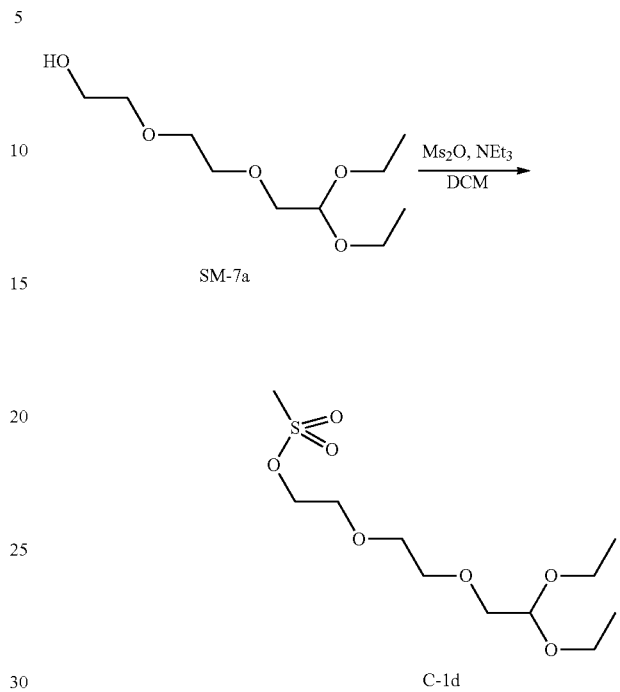

To SM-7a (850 mg; 3.82 mmol) in DCM (8.0 mL) is added methanesulfonic anhydride (666 mg; 3.82 mmol) and NEt₃ (1.11 mL) at 0° C. and the mixture is stirred for 24 h. Saturated aq. NaHCO₃ solution (3.0 mL) is added and the mixture is passed through a phase separator. The filtrate is concentrated in vacuo and the residue is purified by flash chromatography on SiO₂ using 0-100% EtOAc in heptane. The product containing fractions are evaporated to give C-1d.

Step 2: Synthesis of Compound 1-5

To a solution of A-1a (85.0 mg; 160 μmol) and K₂CO₃ (51.0 mg; 369 μmol) in DMF (2.0 mL) is added C-1c (55.0 mg; 193 μmol) and the mixture is stirred at 70° C. for 18 h. After cooling to rt water and DCM is added and the resulting mixtures is passed through a phase separator, the filtrate is concentrated in vacuo and the residue is purified by flash chromatography on SiO₂ using 0-10% MeOH in DCM as eluent. The product containing fractions are evaporated to give D-1c (HPLC-MS: $t_{Ret.}$=1.67 min; MS (M+H)⁺=721; method C).

D-1c (74.8 mg; 104 μmol) in THF (500 μL) and 0.5 M aq. hydrochloric acid (500 μL) is stirred at 50° C. for 45 min. The reaction mixture is concentrated in vacuo to give crude E-1d, which is taken up in DMF (3.0 mL). G-1a (35.7 mg; 104 μmol) and NEt₃ (450 μL) is added followed by MgSO₄ and NaBH(OAc)₃ (117 mg; 550 μmol) and the mixture is stirred at rt for 18 h. The reaction mixture is filtered, concentrated in vacuo and the residue is purified by preparative RP HPLC using 5-95% MeCN in 0.1% aq. HCOOH as eluent. The product containing fractions are freeze dried to give 1-4 (HPLC-MS: $t_{Ret.}$=3.40 min; MS (M+H)⁺=902; method D).

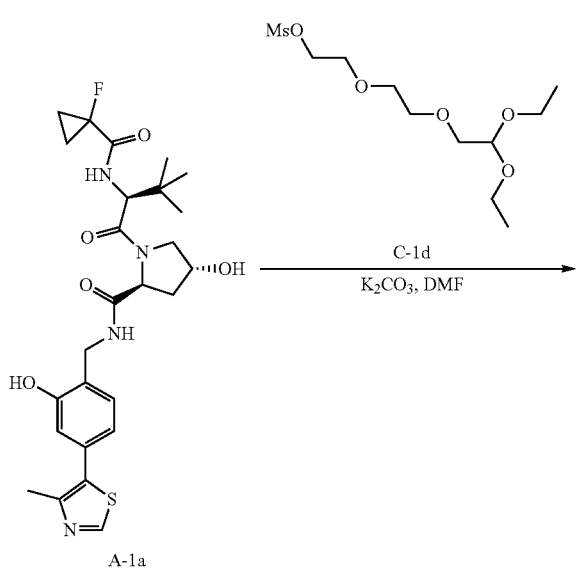

-continued

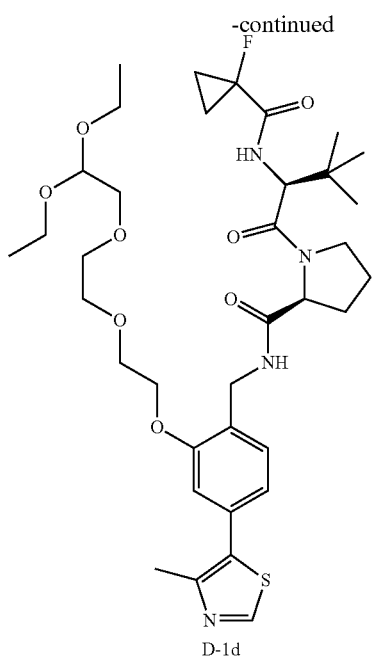

D-1d 0.5M HCl, THF →

-continued

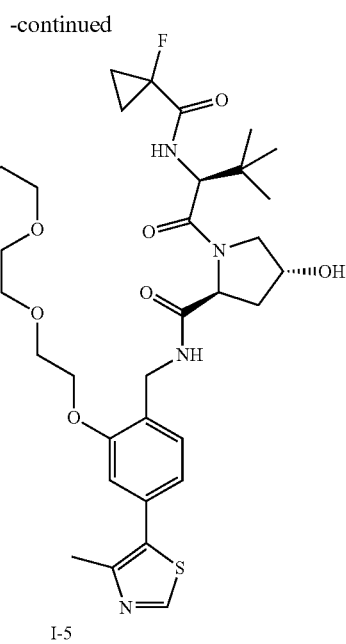

I-5

To a solution of A-1a (152 mg; 285 μmol) and K₂CO₃ (95.0 mg; 687 μmol) in DMF (3.0 mL) is added C-1d (87.5 mg; 291 μmol) and the mixture is stirred at 75° C. for 18 h. After cooling to rt water (1.0 mL) and DCM (50 mL) is added and the resulting mixture is passed through a phase separator, the filtrate is concentrated in vacuo and the residue is purified by flash chromatography on SiO₂ using 0-10% MeOH in DCM as eluent. The product containing fractions are evaporated to give D-1d (HPLC-MS: $t_{Ret.}$=1.55 min; MS $(M+H)^+$=737).

D-1d (85.0 mg; 115 μmol) in THF (500 μL) and 0.5 M aq. hydrochloric acid (500 μL) is stirred at 50° C. for 45 min. The reaction mixture is concentrated in vacuo to give crude E-1e, which is taken up in DMF (3.0 mL). G-1a (38.0 mg; 110 μmol) and NEt₃ (500 μL) is added followed by MgSO₄ and NaBH(OAc)₃ (126 mg; 595 μmol) and the mixture is stirred at rt for 18 h. The reaction mixture is filtered, concentrated in vacuo and the residue is purified by preparative RP HPLC using 5-95% MeCN in 0.1% aq. HCOOH as eluent. The product containing fractions are freeze dried to give 1-5 (HPLC-MS: $t_{Ret.}$=1.17 min; MS $(M+H)^+$=918; method C).

B.2.6 Experimental Procedures for the Synthesis of Compound 1-6

Step 1: Synthesis of Bifunctional Compound C-2a

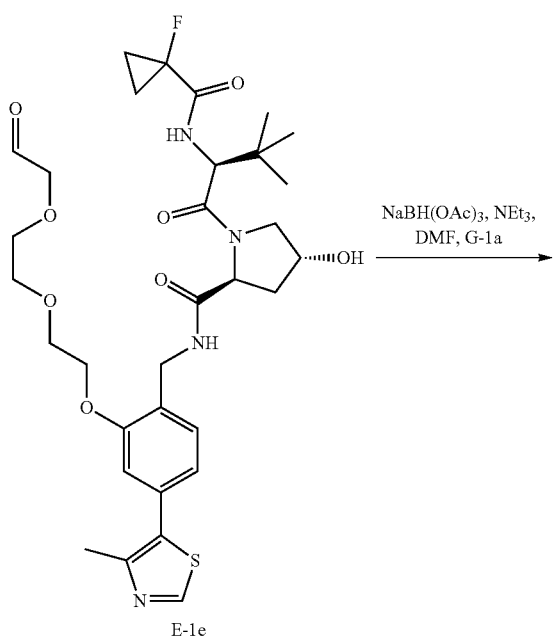

E-1e

NaBH(OAc)₃, NEt₃, DMF, G-1a →

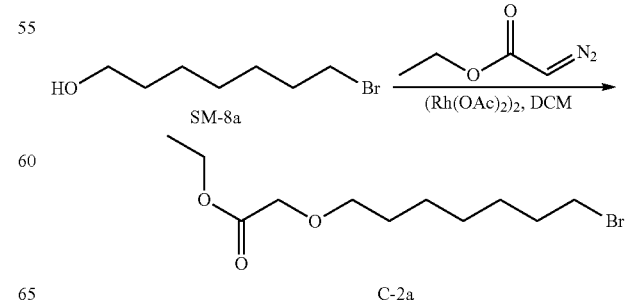

C-2a

To SM-8a (750 mg; 3.84 mmol) in DCM (13 mL) is added (Rh(OAc)$_2$)$_2$ (29.0 mg; 66 μmol) at 0° C. and the mixture is stirred for 5 min. Ethyl diazoacetate (568 mg; 4.98 mmol) in DCM (12 mL) is added dropwise and the reaction mixture is allowed to warm to rt, stirred for 18 h, filtered and evaporated. The residue is purified by flash chromatography on SiO$_2$ using 0-100% EtOAc in heptane as eluent. The product containing fractions are evaporated to give C-2a.

Step 2: Synthesis of Intermediate PG-D-3b

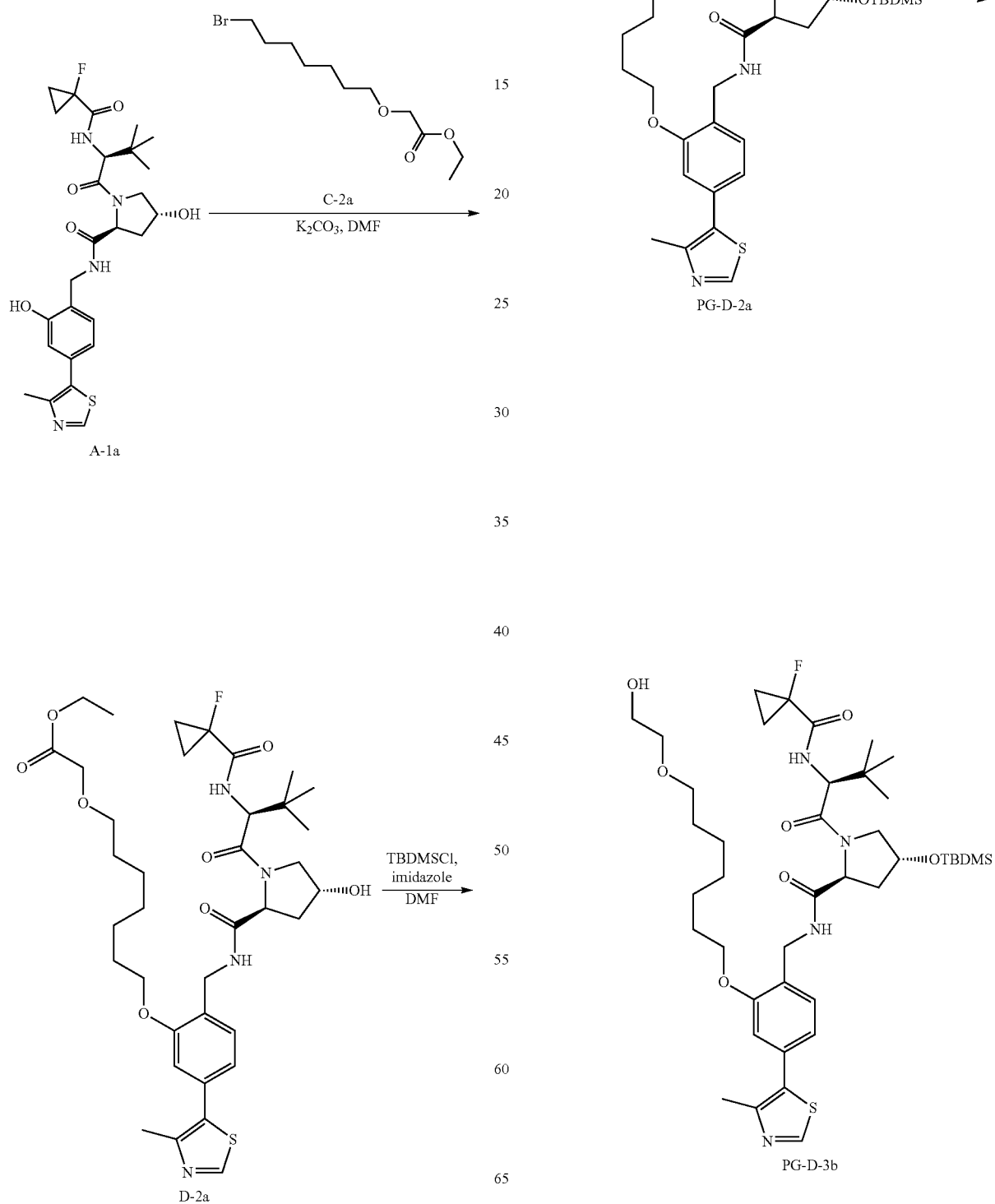

To A-1a (500 mg; 939 µmol) in DMF (7.0 mL) is added C-2a (290 mg; 1.03 mmol) and K₂CO₃ (389 mg; 2.82 mmol) and the mixture is stirred at 70° C. for 16 h. After cooling to rt the reaction mixture is concentrated in vacuo, water and DCM is added and the layers are separated. The organic layer is dried over MgSO₄, filtered, evaporated and the residue is purified by flash chromatography on SiO₂ using 0-10% MeOH in DCM as eluent. The product containing fractions are evaporated to give D-2a (HPLC-MS: $t_{Ret.}$=1.76 min; MS (M+H)⁺=733; method C).

To D-2a (470 mg; 641 µmol) in DMF (6.0 mL) is added imidazole (109 mg; 1.60 mmol) and the mixture is stirred under N₂ for 30 min. TBDMSCI (145 mg; 962 µmol) is added and stirring is continued at rt for 16 h. The reaction mixture is partitioned between saturated NaCl solution and EtOAc. The combined organic layers are dried over MgSO₄, filtered, evaporated and the residue is purified by flash chromatography on SiO₂ using 0-70% EtOAc in heptane as eluent. The product containing fractions are evaporated to give PG-D-2a (HPLC-MS: $t_{Ret.}$=2.30 min; MS (M+H)⁺= 847; method C).

To PG-D-2a (388 mg; 458 µmol) in THF (5.0 mL) is added LAH solution (733 µL; 1 M in THF) at 0° C. over 5 min. The resulting mixture is stirred at 0° C. for 20 min and slowly quenched with solid Na₂SO₄, allowed to warm to rt and stirred for 20 min. The mixture is filtered through celite, washed through with EtOAc (20 mL) and DCM (5 mL) and concentrated in vacuo. The residual crude PG-D-3b (HPLC-MS: $t_{Ret.}$=2.08 min; MS (M+H)⁺=805) is directly used without further purification.

Step 3: Synthesis of Compound 1-6

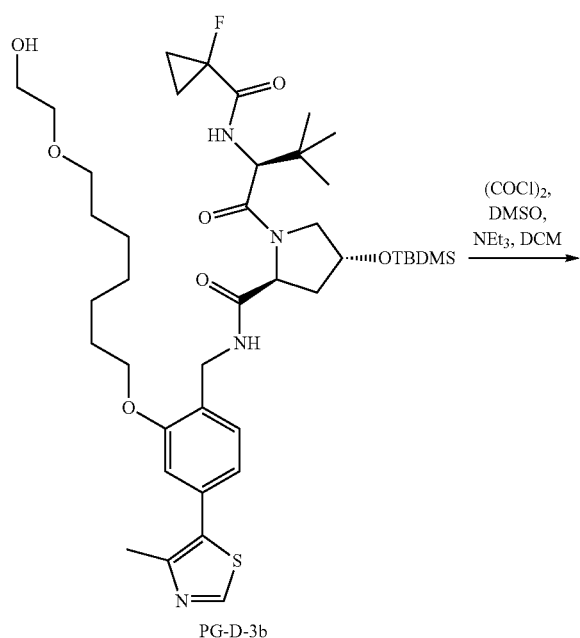

PG-D-3b

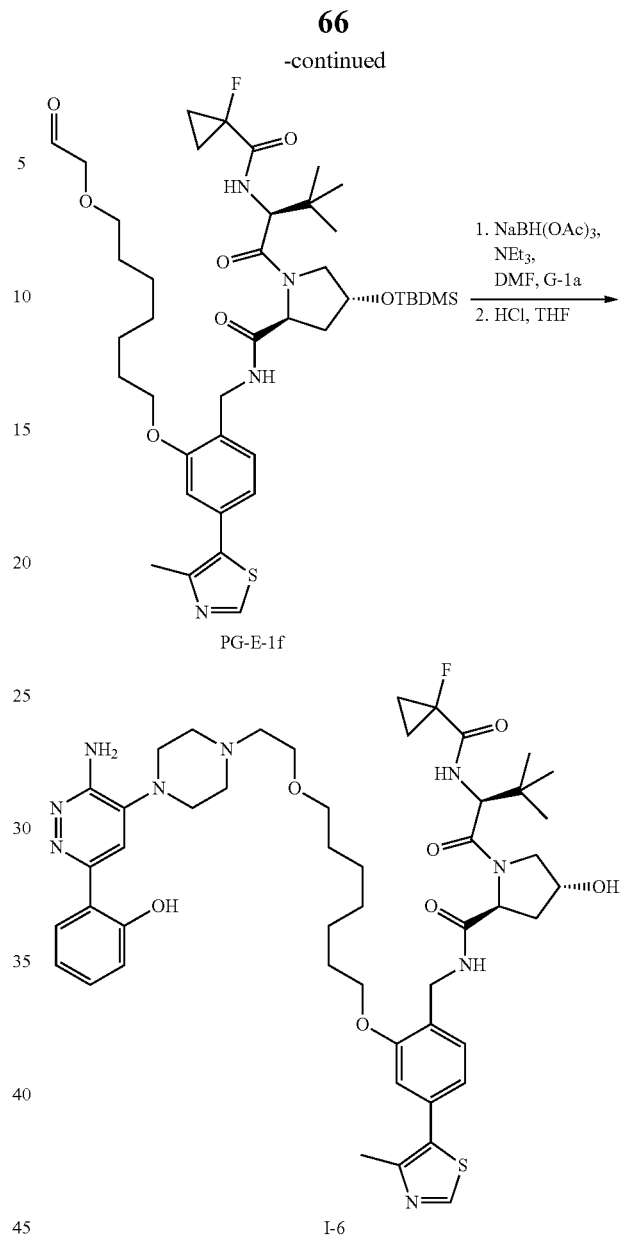

To oxalyl chloride (18.5 µL, 219 µmol) in DCM (3.0 mL) at −78° C. is added DMSO (22.8 µL; 320 µmol) and the mixture is stirred at −78° C. for 10 min. PG-D-3b (120 mg; 149 µmol) in DCM (3.0 mL) is added dropwise and the mixture is stirred at the same temperature for 1 h. NEt₃ (86.2 µL; 596 µmol) is added and the reaction mixture is allowed to warm up to rt and stirred for 1 h. Concentration in vacuo gives crude PG-E-1f, which is taken up in DMF (2.0 mL) under N₂. A solution of G-1a (45.9 mg; 149 mmol), MgSO₄ and NEt₃ (21.6 µL, 149 µmol) in DMF (1.0 mL) is added and the resulting mixture is stirred at rt for 20 min. NaBH(OAc)₃ (126 mg; 596 µmol) is added and stirring is continued for 18 h. DCM is added and the mixture is filtered, concentrated in vacuo, taken up in 1 M hydrochloric acid (2.0 mL) and THF (2.0 mL) and stirred at 40° C. for 1 h to remove the protecting group. After cooling the mixture is concentrated in vacuo and purified by preparative RP HPLC using 5-95% MeCN in 0.1% aq. HCOOH as eluent. The product containing fractions are freeze dried to give 1-6 (HPLC-MS: $t_{Ret.}$=1.32 min; MS (M+H)⁺=918; method C).

B.2.7 Experimental Procedures for the Synthesis of Compound 1-7

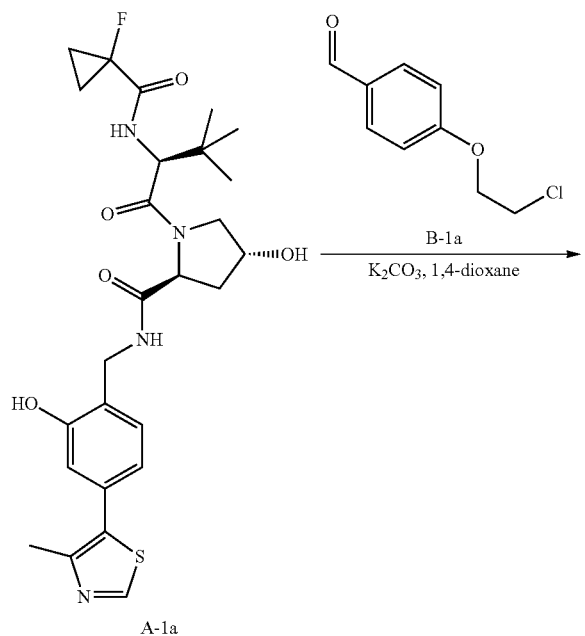

A-1a

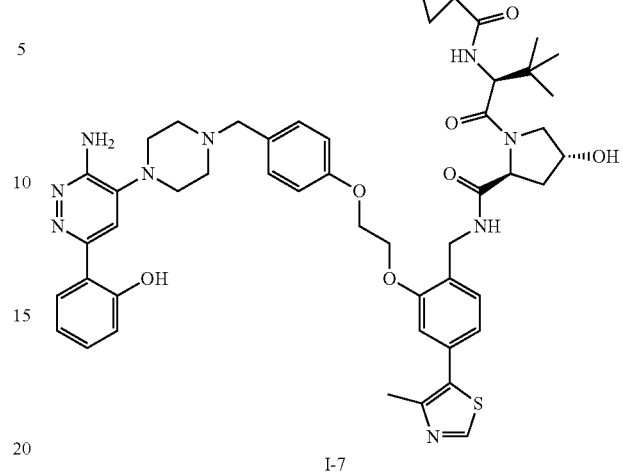

I-7

To A-1a (100 mg; 188 μmol) in 1,4-dioxane (0.5 mL) is added K$_2$CO$_3$ (42.8 mg; 310 μmol) and B-1a (32.1 mg; 174 μmol) and the resulting reaction mixture is stirred at 100° C. for 18 h. After cooling to rt, MeCN and water is added, the mixture is filtered and directly purified by RP HPLC under basic conditions using 20-90% MeCN in water as eluent. The product containing fractions are freeze dried to give E-1g (HPLC-MS: t$_{Ret.}$=1.27 min; MS (M+H)$^+$=681; method E).

To E-1g (55.0 mg; 80.8 μmol) and G-1a (21.9 mg; 80.8 μmol) in DMSO (1.0 mL) is added AcOH (139 μL; 2.42 mmol) and the reaction mixture is stirred at 60° C. for 4 h. NaBH(OAc)$_3$ (68.5 mg; 323 μmol) is added and stirring is continued at 60° C. for 20 h. After cooling to rt MeCN and water is added, the mixture is filtered and directly purified by RP HPLC under basic conditions using 10-90% MeCN in water as eluent. The product containing fractions are freeze dried to give 1-7 (HPLC-MS: t$_{Ret.}$=1.42 min; MS (M+2H)$^{2+}$=468; method E).

B.2.8 Experimental Procedures for the Synthesis of Compound I-8

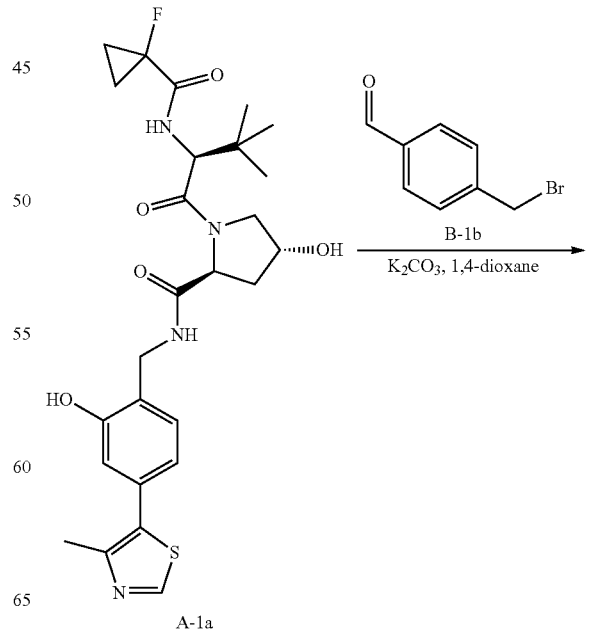

E-1g

A-1a

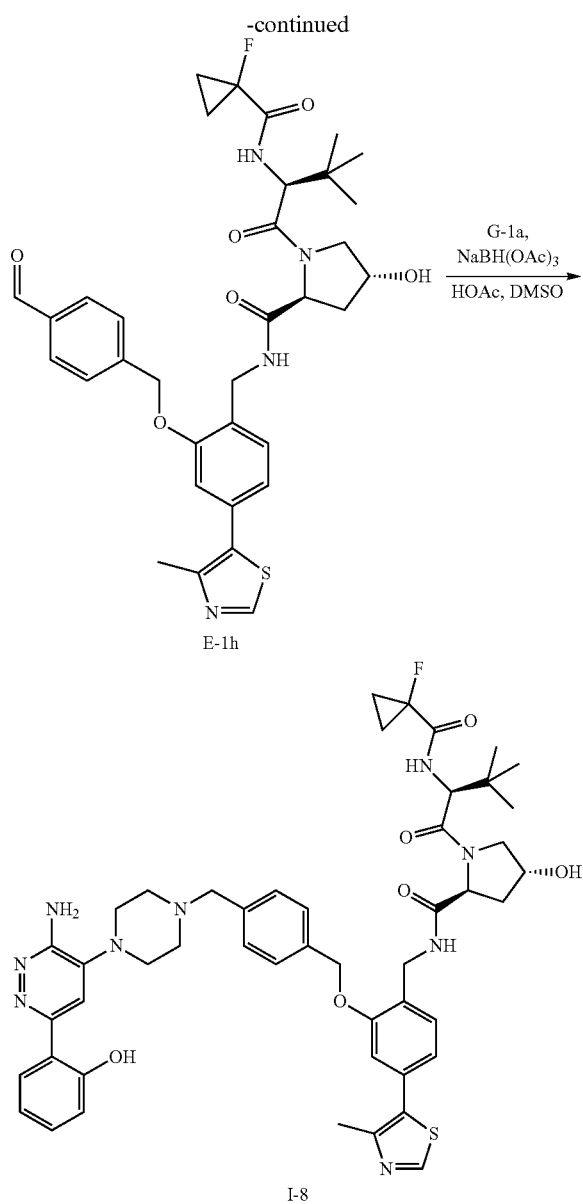

B.2.9 Experimental Procedures for the Synthesis of Compound 1-9

Step 1: Synthesis of Bifunctional Compound B-1c

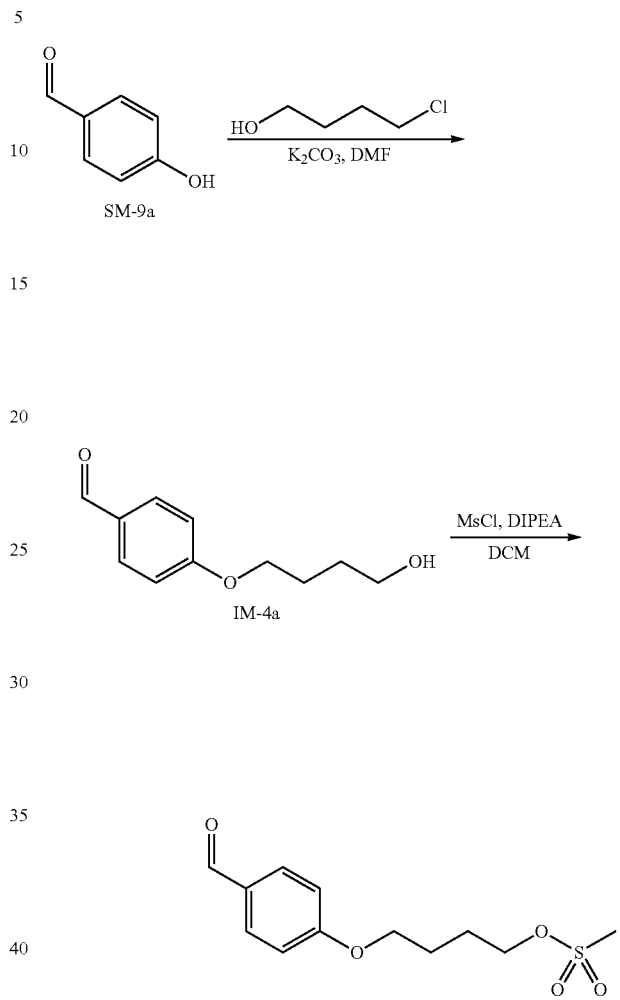

To A-1a (70.0 mg; 131 μmol) in 1,4-dioxane (0.5 mL) is added K$_2$CO$_3$ (30.0 mg; 217 μmol) and B-1b (23.7 mg; 119 μmol) and the resulting reaction mixture is stirred at 110° C. for 18 h. After cooling to rt, MeCN and water is added, the mixture is filtered and directly purified by RP HPLC under basic conditions using 20-90% MeCN in water as eluent. The product containing fractions are freeze dried to give E-1h (HPLC-MS: t$_{Ret.}$=1.27 min; MS (M+H)$^+$=651; method E).

To E-1h (33.0 mg; 50.7 μmol) and G-1a (13.8 mg; 50.7 μmol) in DMSO (0.5 mL) is added AcOH (87 μL; 1.52 mmol) and the reaction mixture is stirred at 70° C. for 30 min. NaBH(OAc)$_3$ (43.0 mg; 203 μmol) is added and stirring is continued at 70° C. for 30 min. After cooling to rt MeCN and water is added, the mixture is filtered and directly purified by RP HPLC under basic conditions using 10-90% MeCN in water as eluent. The product containing fractions are freeze dried to give I-8 (HPLC-MS: t$_{Ret.}$=1.43 min; MS (M+2H)$^{2+}$=453; method E).

To SM-9a (200 mg; 1.64 mmol) and K$_2$CO$_3$ (679 mg; 4.91 mmol) in DMF (2.0 mL) is added 4-chlorobutan-1-ol (490 μL; 4.92 mmol) dropwise and the reaction mixture is stirred for 20 h at 65° C. After cooling to rt water is added and the mixture is acidified with hydrochloric acid and extracted with EtOAc. The combined organic layer is dried over MgSO$_4$, filtered and evaporated. The residue is purified by RP HPLC under basic conditions using 2-80% MeCN in water as eluent. The product containing fractions are freeze dried to give IM-4a (HPLC-MS: t$_{Ret.}$=0.34 min; MS (M+H)$^+$=195; method F).

To IM-4a (25.0 mg; 129 μmol) in DCM (1.0 mL) at 0° C. is added DIPEA (62.4 μL; 387 mmol) followed by methanesulfonyl chloride (11.0 μL; 142 μmol) and the resulting mixture is allowed to warm to rt and stirred for 1 h. Water and DCM is added and the mixture is extracted with DCM. The combined organic layer is dried over MgSO$_4$, filtered and evaporated to give B-1c (HPLC-MS: t$_{Ret.}$=0.48 min; MS (M+H)$^+$=273; method F), which is directly used for the next step.

Step 2: Synthesis of Compound 1-9

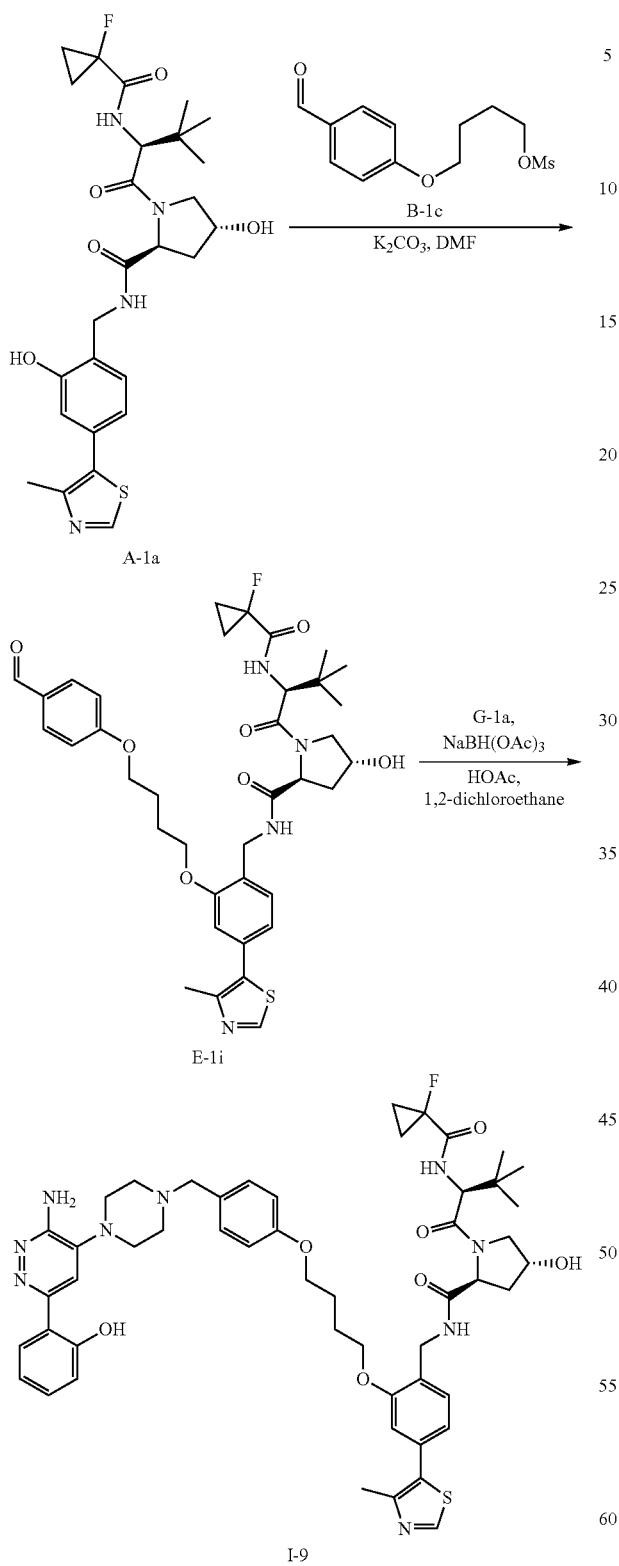

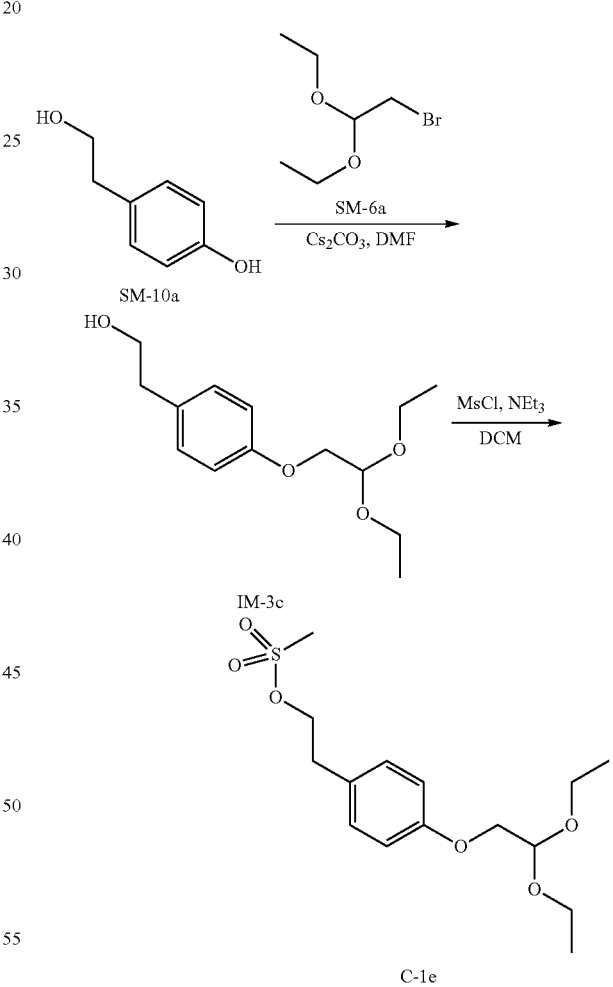

water is added, the mixture is filtered and directly purified by RP HPLC under basic conditions using 10-98% MeCN in water as eluent. The product containing fractions are freeze dried to give E-1i (HPLC-MS: $t_{Ret.}$=0.68 min; MS (M+H)$^+$= 724; method F).

To E-1i (62.7 mg; 88.5 μmol) and G-1a (20.0 mg; 73.7 μmol) in DCM (0.5 mL) is added AcOH (45 μL) and the mixture is stirred for 30 min at rt. NaBH(OAc)$_3$ (31.2 mg; 147 μmol) is added and stirring is continued for 1 h at rt. NEt$_3$ (60 μL) and DMF (0.5 mL) is added and stirring is continued for 30 min. Water is added and the mixture is concentrated in vacuo. The residue is taken up in water/MeCN, filtered and purified by RP HPLC under basic conditions using 10-90% MeCN in water as eluent. The product containing fractions are freeze dried to give 1-9 (HPLC-MS: $t_{Ret.}$=1.51 min; MS (M+2H)$^{2+}$=482; method E).

B.2.10 Experimental Procedures for the Synthesis of Compound 1-10

Step 1: Synthesis of Bifunctional Compound C-1e

A mixture of SM-10a (1.00 g; 7.23 mmol), SM-6a (1.56 g; 7.91 mmol) and Cs$_2$CO$_3$ (2.93g; 8.99 mmol) in DMF (15 mL) is stirred at 90° C. for 20 h. After cooling to rt water (50 mL) is added and the mixture is extracted with EtOAc (3×50 mL). The combined organic layer is washed with water and brine, dried over MgSO$_4$, filtered and evaporated. The residue is purified by flash chromatography on silica gel using 2-50% EtOAc in heptane as eluent. The product containing fractions are evaporated to give IM-3c.

To A-1a (60.0 mg; 113 μmol) in DMF (0.6 mL) is added K$_2$CO$_3$ (46.7 mg; 338 μmol) and a solution of B-1c (33.7 mg; 124 μmol) in DMF (0.6 mL) and the resulting mixture is stirred for 1 h at 75° C. After cooling to rt MeCN and To IM-3c (1.55 g; 6.09 mmol) in DCM (15 mL) at 0° C. is added NEt₃ (1.06 mL; 7.31 mmol) followed by methanesulfonyl chloride (512 µL; 6.70 mmol) and the resulting mixture is stirred for 3 h. Water (3.0 mL), sat. NaHCO₃ solution (3.0 mL) and DCM (100 mL) is added and the solution is passed through a phase separator. The filtrate is evaporated and the residue purified by flash chromatography on silica gel using 0-50% EtOAc in heptane as eluent. The product containing fractions are evaporated to give C-1e.

Step 2: Synthesis of Compound 1-10

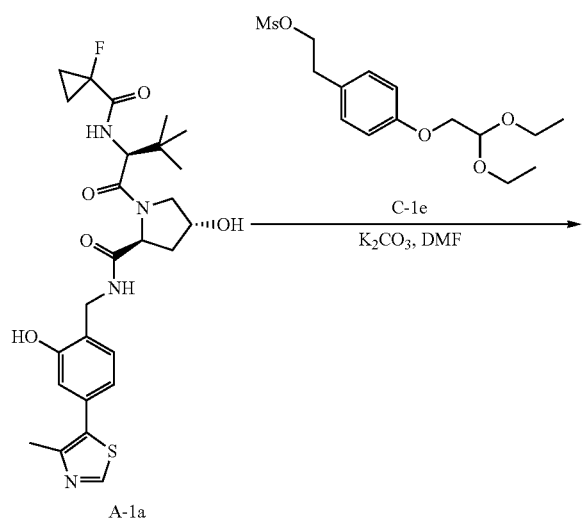

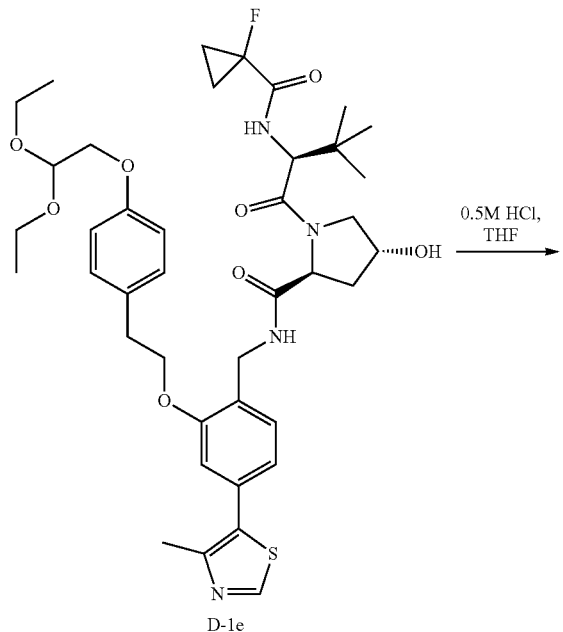

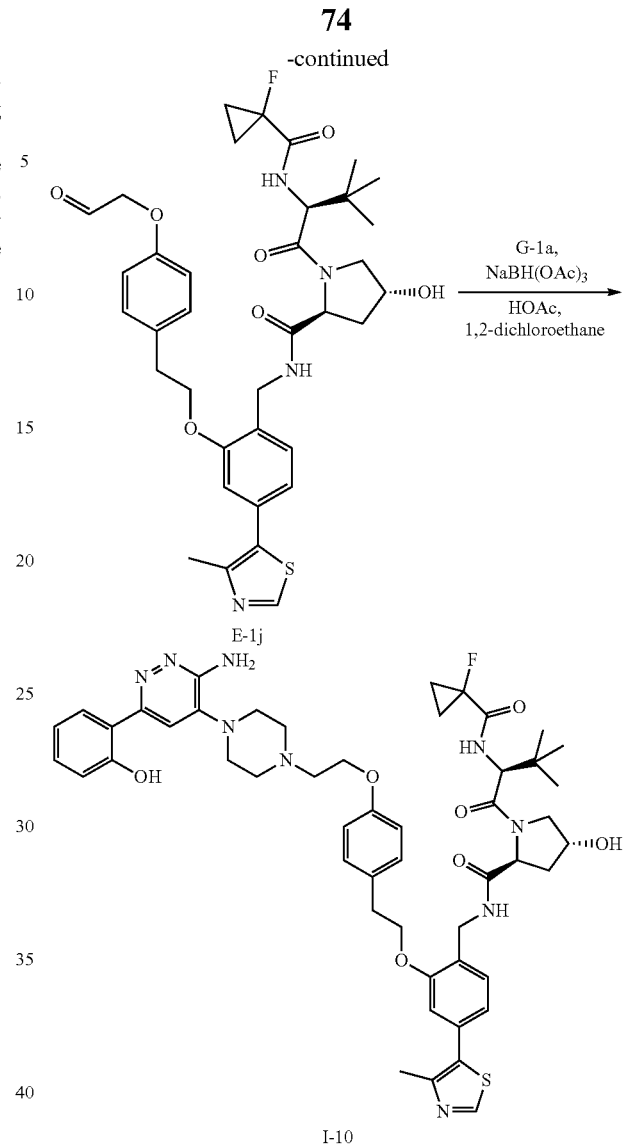

To A-1a (77.0 mg; 145 µmol) in DMF (2.0 mL) is added K₂CO₃ (69.0 mg; 499 µmol) and C-1e (67.0 mg; 202 µmol) and the resulting mixture is stirred at 70° C. for 18 h. After cooling to rt DCM (100 mL) and water (3.0 mL) is added and the solution is passed through a phase separator. The filtrate is evaporated and the residue purified by flash chromatography on silica gel using 0-5% MeOH in DCM as eluent. The product containing fractions are evaporated to give D-1e (HPLC-MS: $t_{Ret.}$=1.80 min; MS (M+H)⁺=769; method C).

To D-1e (94.7 mg; 123 µmol) in THF (1.0 mL) is added 0.5 M HCl (1.0 mL) and the mixture is stirred at 75° C. for 45 min. After cooling to rt the mixture is concentrated under reduced pressure, the residue (→E-1j) is taken up in 1,2-dichloroethane (4.0 mL) and G-1a (42.0 mg; 122 µmol) is added followed by NEt₃ (600 µL; 4.15 mmol), MgSO₄ and NaBH(OAc)₃ (150 mg; 707 µmol). The resulting mixture is stirred at rt for 17 h, filtered and evaporated. The residue is taken up and is purified by RP HPLC under acidic conditions using 0-60% MeCN in 0.1% aq. formic acid as eluent. The product containing fractions are freeze dried to give 1-10 (HPLC-MS: $t_{Ret.}$=4.60 min; MS (M+2H)²⁺=476; method D).

B.2.11 Experimental Procedures for the Synthesis of Compound 1-11

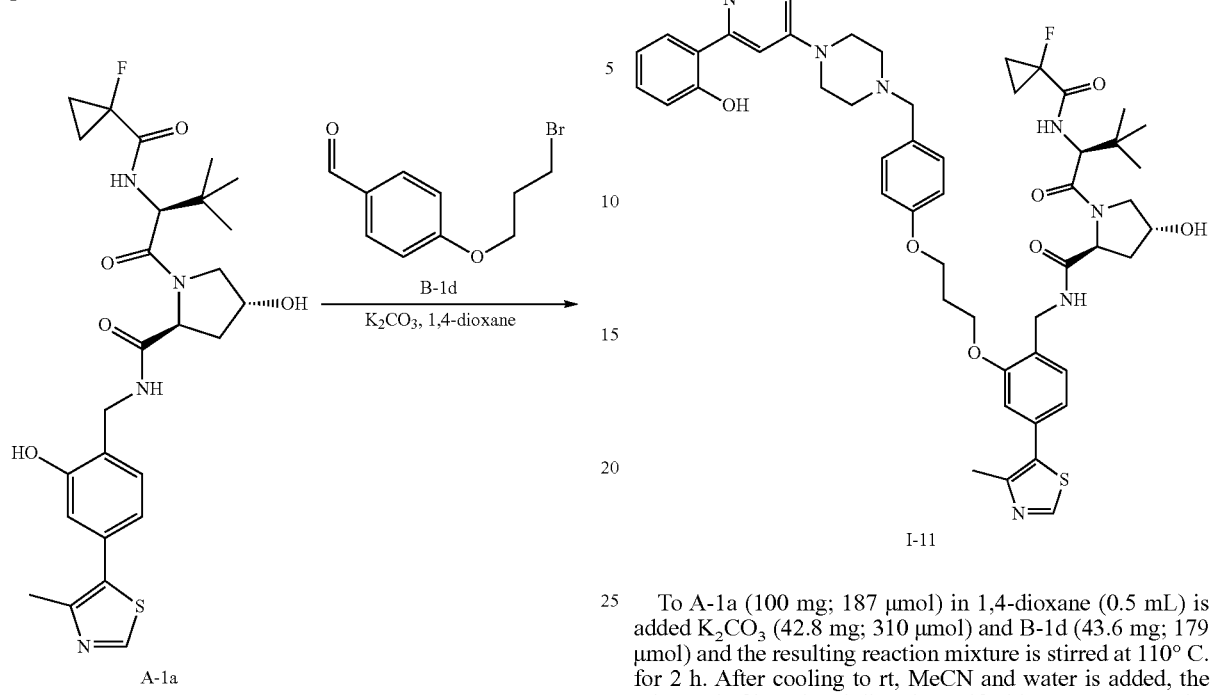
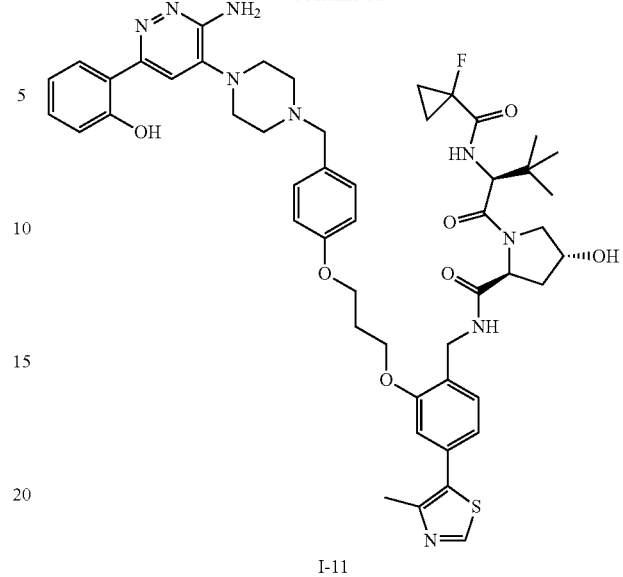

To A-1a (100 mg; 187 μmol) in 1,4-dioxane (0.5 mL) is added K$_2$CO$_3$ (42.8 mg; 310 μmol) and B-1d (43.6 mg; 179 μmol) and the resulting reaction mixture is stirred at 110° C. for 2 h. After cooling to rt, MeCN and water is added, the mixture is filtered and directly purified by RP HPLC under basic conditions using 15-90% MeCN in water as eluent. The product containing fractions are freeze dried to give E-1k (HPLC-MS: $t_{Ret.}$=1.33 min; MS (M+H)$^+$=695; method E).

To E-1k (25.0 mg; 36.0 μmol) and G-1a (10.3 mg; 38.0 μmol) in DMF (0.5 mL) is added AcOH (62 μL) and the reaction mixture is stirred at rt for 2 h. NaBH(OAc)$_3$ (62.9 mg; 297 μmol) is added and stirring is continued at rt for 2 h. After cooling to rt MeCN and water is added, the mixture is filtered and directly purified by RP HPLC under basic conditions using 15-90% MeCN in water as eluent. The product containing fractions are freeze dried to give 1-11 (HPLC-MS: $t_{Ret.}$=1.47 min; MS (M+2H)$^{2+}$=475; method E).

B 2.12 Experimental Procedures for the Synthesis of Compound 1-12

Step 1: Synthesis of Bifunctional Compound C-1f

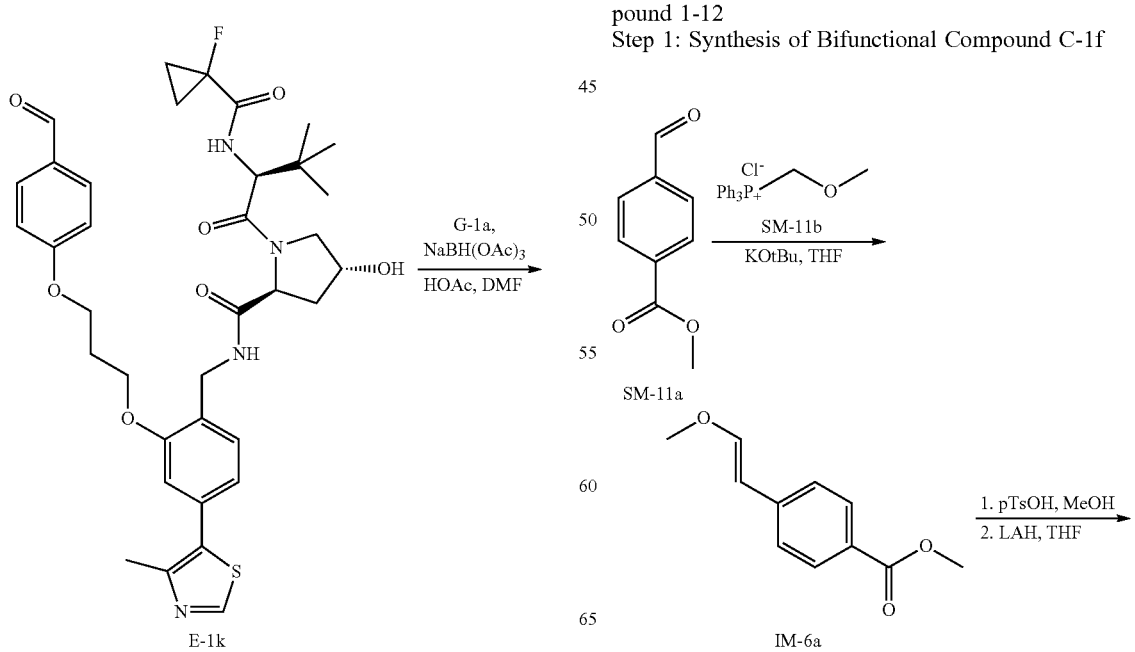

-continued

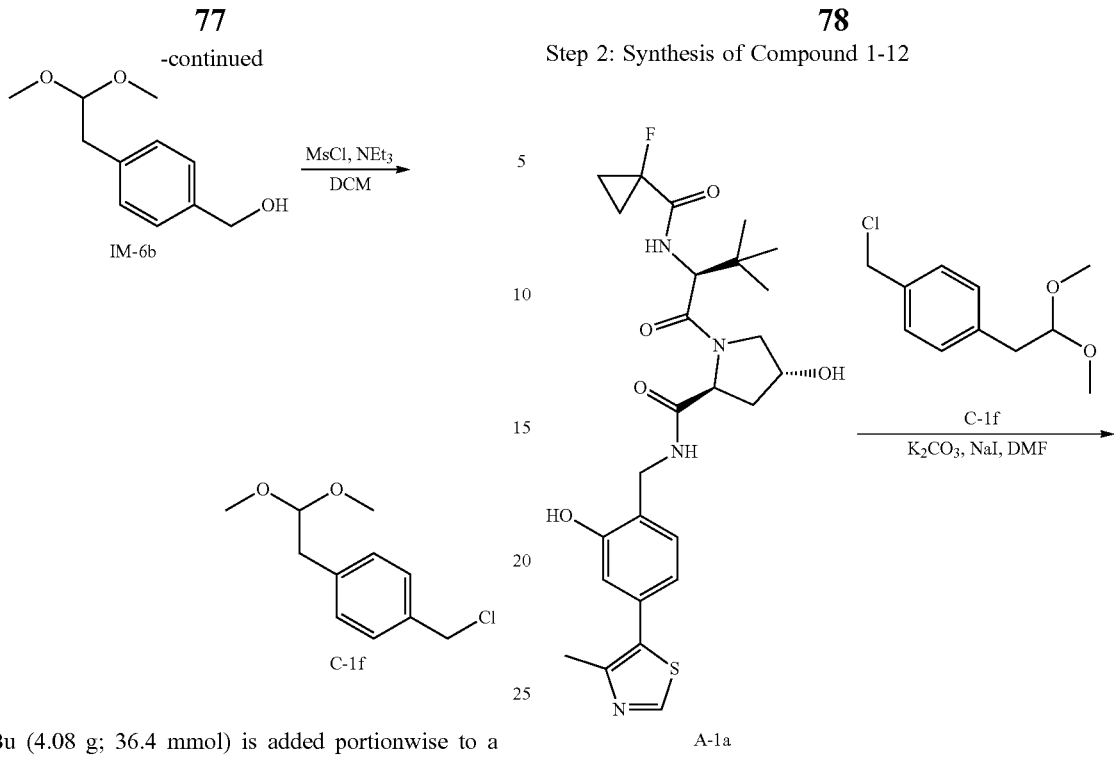

Step 2: Synthesis of Compound 1-12

KOtBu (4.08 g; 36.4 mmol) is added portionwise to a suspension of SM-11b (10.0 g; 29.2 mmol) in THF (64 mL) (water bath cooling) and the resulting mixture is stirred at rt for 20 min. At the same temperature SM-11a (4.00 g; 24.4 mmol) is added dropwise and stirring is continued for 18 h. The reaction mixture is quenched with water and concentrated under reduced pressure to remove all organics. The residue is extracted with EtOAc (3×100 mL) and the combined organic layer is washed with water (50 mL) and brine (50 mL), dried over $MgSO_4$, filtered and evaporated. The residue is purified by flash chromatography on silica gel using 0-50% EtOAc in heptane. The product containing fractions are evaporated to give IM-6a as a 1:1 E:Z mixture.

pTsOH (310 mg; 1.63 mmol) is added to a solution of IM-6a (1.45 g; 7.54 mmol) in MeOH (30 mL). The resulting reaction mixture is refluxed for 18 h. After cooling to rt, the reaction mixture is concentrated under reduced pressure, partitioned between DCM (100 mL) and 10% aq. $K_2CO_3$ (100 mL) and passed through a phase separator. The organic layer is concentrated in vacuo and the remaining solid is dissolved in THF (30 mL) and cooled to 0° C. LAH (7.0 mL; 1 M solution; 7.00 mmol) is then added and the reaction mixture is stirred at 0° C. for 4 h. The reaction mixture is quenched with $Na_2SO_4·10\ H_2O$, stirred at rt for 30 min, filtered through Celite and washed with THF and DCM. The filtrate is concentrated in vacuo and the remaining residue is purified by column chromatography on silica gel using 0-70% EtOAc in heptane as eluent. The product containing fractions are evaporated to give IM-6b ($R_f$=0.52; heptane/EtOAc=1:1; stain: $KMnO_4$).

To IM-6b (112 mg; 571 μmol) in DCM (5.0 mL) at 0° C. is added $NEt_3$ (150 μL; 1.04 mmol) followed by methanesulfonyl chloride (60.0 μL; 786 μmol) and the resulting mixture is stirred at 5° C. for 2 h. Sat. $NaHCO_3$ solution (3.0 mL) is added and the solution is passed through a phase separator. The filtrate is evaporated and the residue purified by flash chromatography on silica gel using 0-40% EtOAc in heptane as eluent. The product containing fractions are evaporated to give C-1f.

B 2.13 Experimental Procedures for the Synthesis of Compound 1-13
Step 1: Synthesis of Bifunctional Compound C-1g

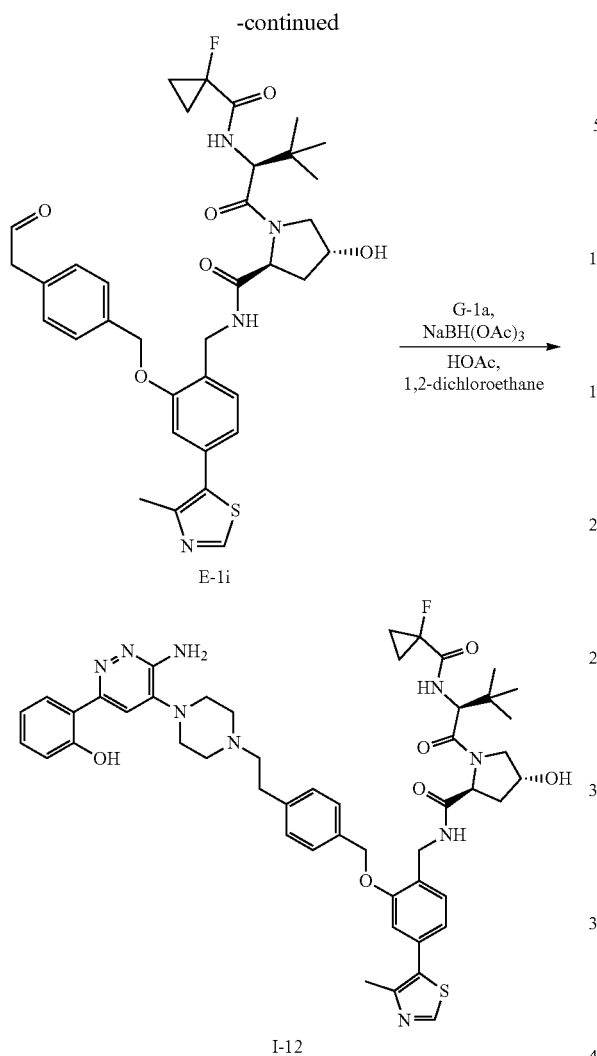

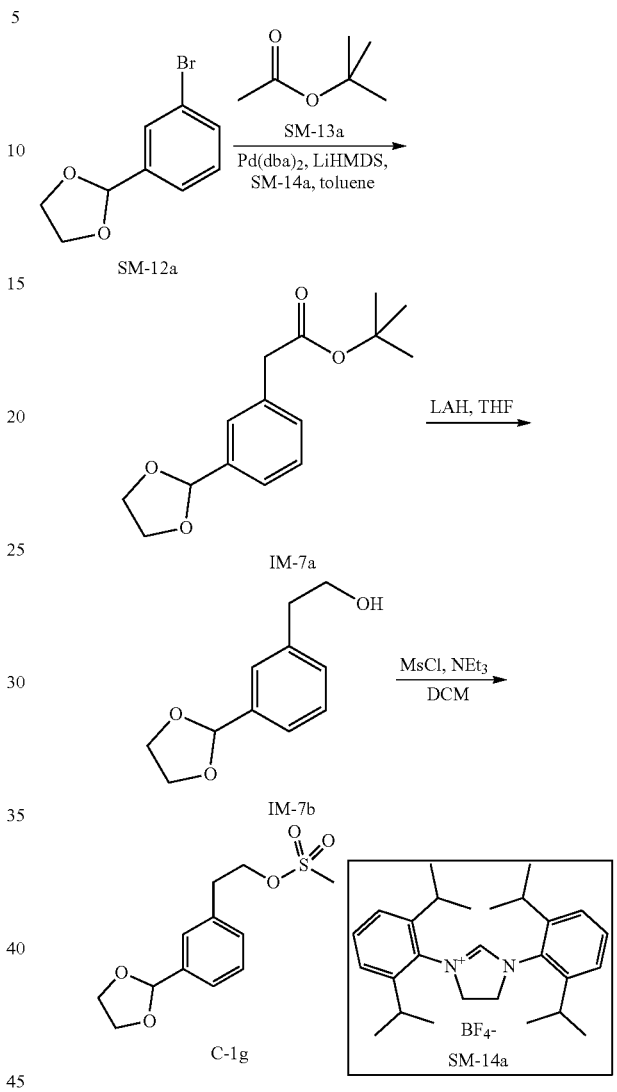

To A-1a (120 mg; 225 µmol) in DMF (3.0 mL) is added K₂CO₃ (165 mg; 1.19 mmol), NaI (10.0 mg; 66.7 µmol) and C-1f (70.0 mg; 326 µmol) and the resulting mixture is stirred at 70° C. for 18 h. After cooling to rt DCM (100 mL) and water (3.0 mL) is added and the solution is passed through a phase separator. The filtrate is evaporated and the residue purified by flash chromatography on silica gel using 0-10% MeOH in DCM as eluent. The product containing fractions are evaporated to give D-1f (HPLC-MS: $t_{Ret.}$=1.66 min; MS $(M+H)^+$=710; method C).

To D-1f (66.2 mg; 93.1 µmol) in THF (1.0 mL) is added 0.5 M HCl (1.0 mL) and the mixture is stirred at 75° C. for 45 min. After cooling to rt the mixture is concentrated under reduced pressure, the residue (→E-11) is taken up in 1,2-dichloroethane (3.0 mL) and G-1a (32.1 mg; 93.2 µmol) is added followed by NEt₃ (404 µL; 2.80 mmol), MgSO₄ and NaBH(OAc)₃ (98.7 mg; 466 µmol). The resulting mixture is stirred at rt for 17 h, filtered and evaporated. The residue is taken up and is purified by RP HPLC under acidic conditions using 0-60% MeCN in 0.1% aq. formic acid as eluent followed by RP HPLC under basic conditions using 5-95% MeCN in 0.1% aq. NH₃ as eluent. The product containing fractions are freeze dried to give 1-12 (HPLC-MS: $t_{Ret.}$=4.50 min; MS $(M+H)^+$=920; method D).

To SM-12a (1.80 g; 7.86 mmol) in toluene (4.0 mL) under N₂ atmosphere is added Pd(dba)₂ (192 mg; 334 µmol), SM-14a (176 mg; 368 µmol), LiHMDS (18.4 mL of 1.0 M solution; 18.4 mmol) followed by SM-13a (1.08 g; 9.30 mmol) in four separate vials. The vials are sealed and stirred at rt for 18 h. The combined reaction mixture is diluted with Et₂O (200 mL) and washed with sat. NH₄Cl solution (200 mL) and brine (100 mL). The organic layer is dried over MgSO₄, filtered and concentrated in vacuo. The residue is purified by flash chromatography on silica gel using 0-10% EtOAc in heptane as eluent. The product containing fractions are evaporated to give IM-7a.

To IM-7a (1.00 g; 3.78 mmol) in THF (15 mL) is added LAH (8.0 mL of a 1.0 M solution; 8.00 mmol) dropwise at 0° C. The resulting mixture is stirred at 0° C. for 2 h, then quenched with Na₂SO₄·10 H₂O and stirred for 30 min. The mixture is filtered through celite, washed with THF and DCM and evaporated. The residue is purified by flash chromatography on silica gel using 0-70% EtOAc in heptane as eluent. The product containing fractions are evaporated to give IM-7b.

To IM-7b (546 mg; 2.81 mmol) in DCM (15.0 mL) at 0° C. is added NEt₃ (2.0 mL; 13.8 mmol) followed by methanesulfonyl chloride (300 µL; 3.93 mmol) and the resulting mixture is stirred 0° C. for 2 h. Sat. NaHCO₃ solution (3.0 mL) is added and the solution is passed through a phase separator. The filtrate is evaporated and the residue purified by flash chromatography on silica gel using 0-70% EtOAc in heptane as eluent. The product containing fractions are evaporated to give C-1g.

Step 2: Synthesis of Compound 1-13

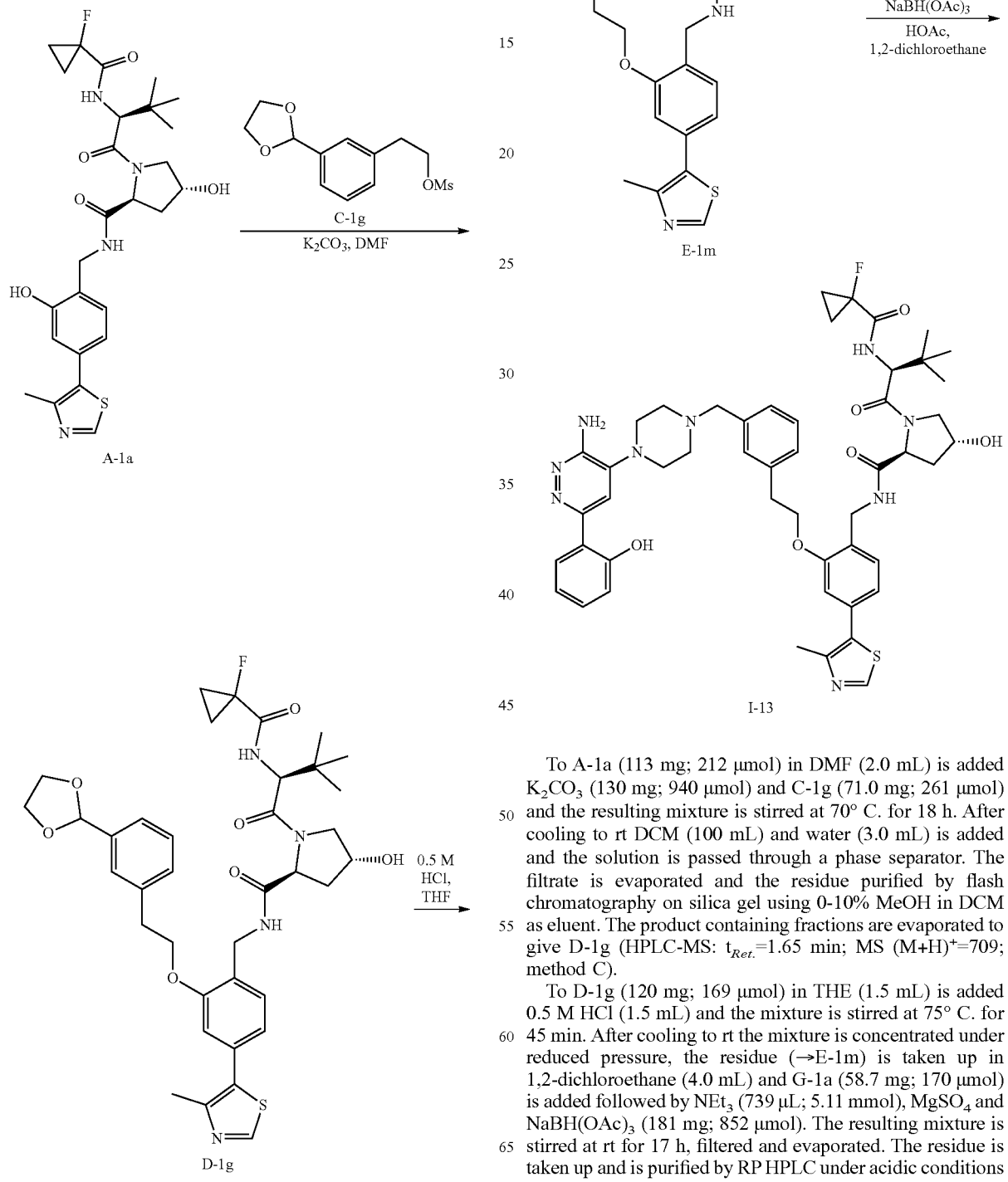

To A-1a (113 mg; 212 µmol) in DMF (2.0 mL) is added K₂CO₃ (130 mg; 940 µmol) and C-1g (71.0 mg; 261 µmol) and the resulting mixture is stirred at 70° C. for 18 h. After cooling to rt DCM (100 mL) and water (3.0 mL) is added and the solution is passed through a phase separator. The filtrate is evaporated and the residue purified by flash chromatography on silica gel using 0-10% MeOH in DCM as eluent. The product containing fractions are evaporated to give D-1g (HPLC-MS: $t_{Ret.}$=1.65 min; MS (M+H)⁺=709; method C).

To D-1g (120 mg; 169 µmol) in THF (1.5 mL) is added 0.5 M HCl (1.5 mL) and the mixture is stirred at 75° C. for 45 min. After cooling to rt the mixture is concentrated under reduced pressure, the residue (→E-1m) is taken up in 1,2-dichloroethane (4.0 mL) and G-1a (58.7 mg; 170 µmol) is added followed by NEt₃ (739 µL; 5.11 mmol), MgSO₄ and NaBH(OAc)₃ (181 mg; 852 µmol). The resulting mixture is stirred at rt for 17 h, filtered and evaporated. The residue is taken up and is purified by RP HPLC under acidic conditions using 0-60% MeCN in 0.1% aq. formic acid as eluent followed by RP HPLC under basic conditions using 5-95% MeCN in 0.1% aq. NH₃ as eluent. The product containing fractions are freeze dried to give 1-13 (HPLC-MS: $t_{Ref.}$=4.70 min; MS (M+H)⁺=920; method D).

B 2.14 Experimental Procedures for the Synthesis of Compound 1-14

Step 1: Synthesis of Bifunctional Compound C-1h

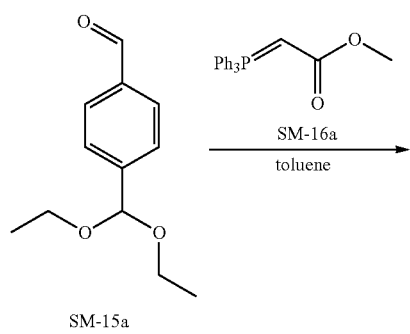

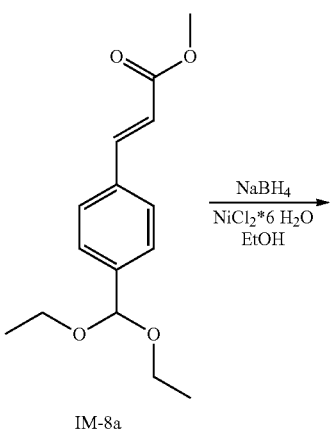

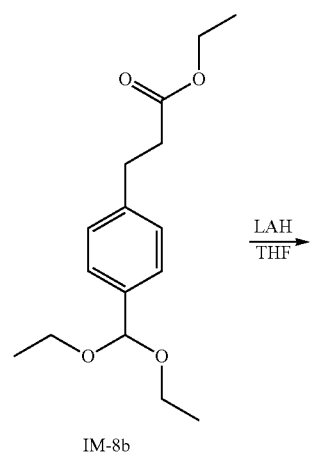

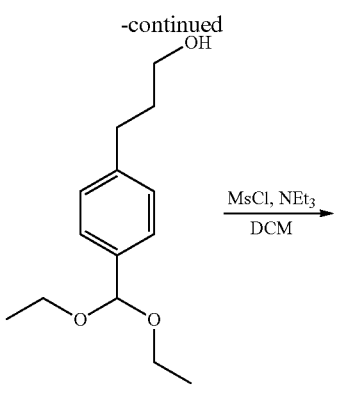

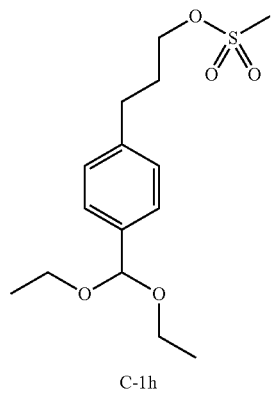

A mixture of SM-15a (2.08 g; 9.98 mmol) and SM-16a (3.68 g; 11.0 mmol) in toluene (30 mL) is heated at reflux for 18 h. After cooling to rt the mixture is concentrated in vacuo and the residue is purified by flash chromatography on silica gel using 0-15% EtOAc in heptane as eluent. The product containing fractions are evaporated to give IM-8a.

To IM-8a (1.32 g; 4.99 mmol) in EtOH (15 mL) is added NiCl₂·6 H₂O (100 mg; 421 µmol) and NaBH₄ (215 mg; 5.68 mmol) and the mixture is stirred at rt for 18 h. The reaction mixture is quenched with water and extracted with EtOAc. The combined organic layer is dried over MgSO₄, filtered and evaporated. The residue is purified by flash chromatography on silica gel using 0-30% EtOAc in heptane as eluent. The product containing fractions are evaporated to give IM-8b.

To IM-8b (1.10 g; 3.92 mmol) in THF (15 mL) at 0° C. is added LAH (8.0 mL of a 1.0 M solution; 8.00 mmol) dropwise. The resulting mixture is stirred at 0° C. for 2 h, then quenched with Na₂SO₄·10 H₂O and stirred for 30 min. The mixtures is filtered through celite, washed with THF and DCM and the filtrate is evaporated. The residue is purified by flash chromatography on silica gel using 0-70% EtOAc in heptane as eluent. The product containing fractions are evaporated to give IM-8c.

To IM-8c (458 mg; 1.92 mmol) in DCM (15.0 mL) at 0° C. is added NEt₃ (2.0 mL; 13.8 mmol) followed by methanesulfonyl chloride (250 µL; 3.27 mmol) and the resulting mixture is stirred 0° C. for 30 min. Sat. NaHCO₃ solution (3.0 mL) is added and the solution is passed through a phase separator. The filtrate is evaporated and the residue purified by flash chromatography on silica gel using 0-70% EtOAc in heptane as eluent. The product containing fractions are evaporated to give C-1h.

Step 2: Synthesis of Compound 1-14

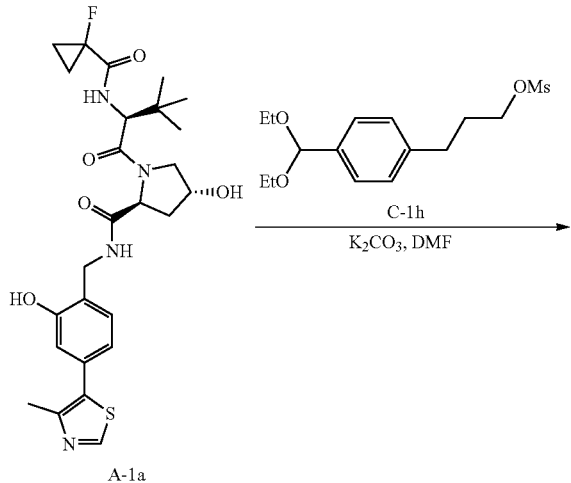

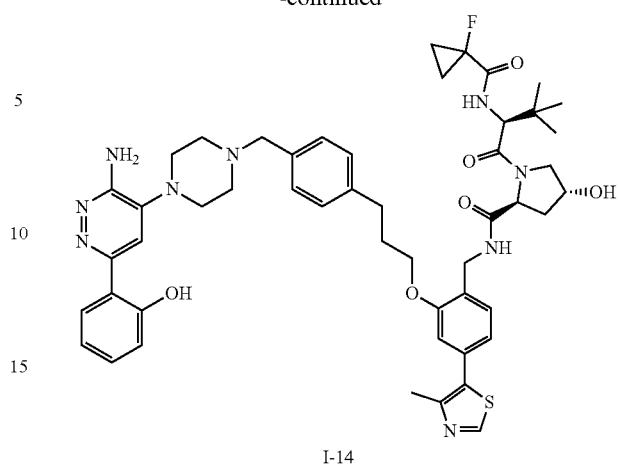

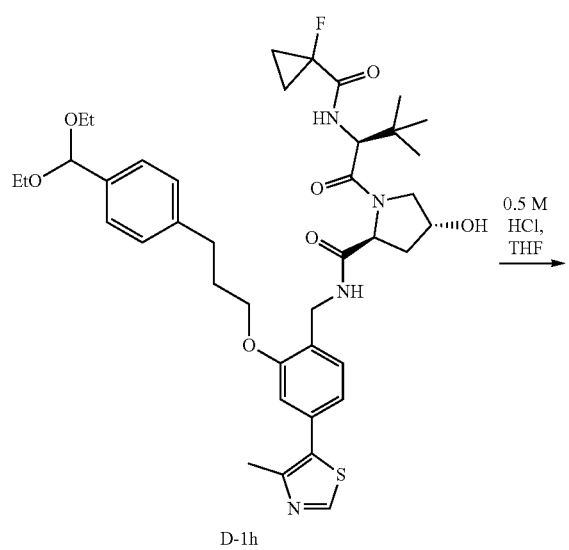

To A-1a (93.0 mg; 175 μmol) in DMF (2.0 mL) is added K$_2$CO$_3$ (80.0 mg; 579 μmol) and C-1h (70.0 mg; 223 μmol) and the resulting mixture is stirred at 70° C. for 18 h. After cooling to rt DCM (100 mL) and water (3.0 mL) is added and the solution is passed through a phase separator. The filtrate is evaporated and the residue purified by flash chromatography on silica gel using 0-10% MeOH in DCM as eluent. The product containing fractions are evaporated to give D-1h (HPLC-MS: t$_{Ret.}$=1.64 min; MS (M+H)$^+$=679—mass of corresponding aldehyde; method C).

To D-1h (110 mg; 146 μmol) in THF (1.5 mL) is added 0.5 M HCl (1.5 mL) and the mixture is stirred at 75° C. for 45 min. After cooling to rt the mixture is concentrated under reduced pressure, the residue (→E-1n) is taken up in 1,2-dichloroethane (4.0 mL) and G-1a (58.7 mg; 170 μmol) is added followed by NEt$_3$ (700 μL; 4.84 mmol), MgSO$_4$ and NaBH(OAc)$_3$ (150 mg; 708 μmol). The resulting mixture is stirred at rt for 17 h, filtered and evaporated. The residue is taken up and is purified by RP HPLC under acidic conditions using 0-60% MeCN in 0.1% aq. formic acid as eluent followed by RP HPLC under basic conditions using 5-95% MeCN in 0.1% aq. NH$_3$ as eluent. The product containing fractions are freeze dried to give 1-14 (HPLC-MS: t$_{Ret.}$=4.70 min; MS (M+H)$^+$=934; method D).

B 2.15 Experimental Procedures for the Synthesis of Compound 1-15

Step 1: Synthesis of Bifunctional Compound C-1i

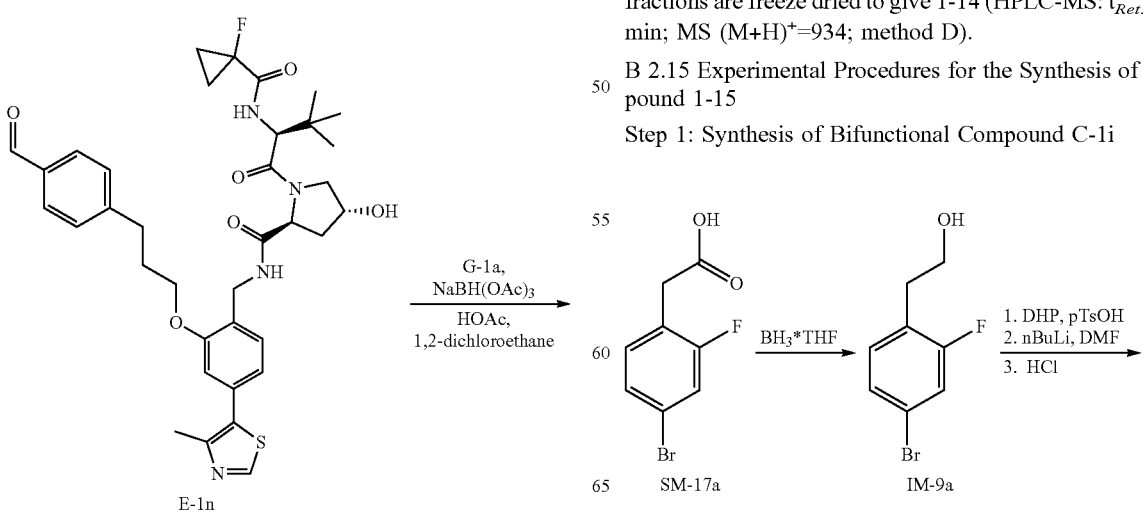

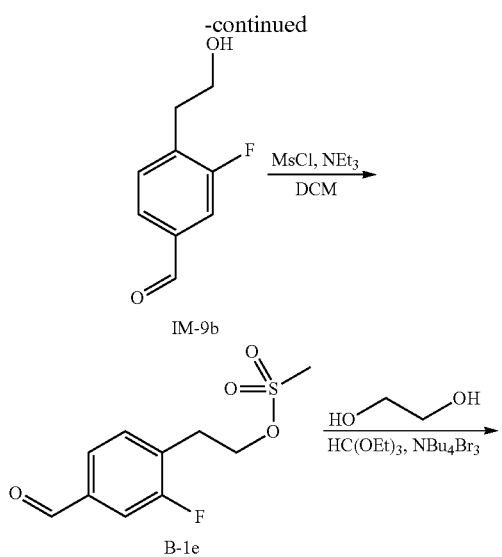

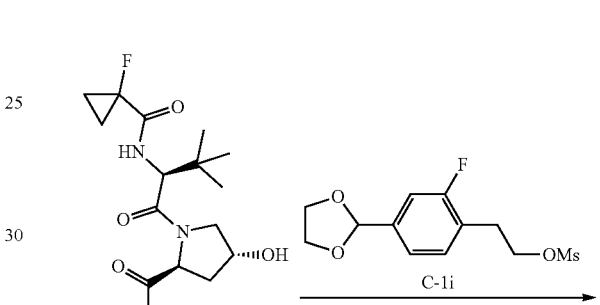

To SM-17a (2.33 g; 10.0 mmol) in THF (6.0 mL) is added BH₃-THF complex (14.0 mL of 1 M solution; 14.0 mmol) dropwise at 0° C. and the resulting mixture is allowed to warm to rt and stirred for 1 h. The mixture is quenched with sat. K₂CO₃ solution (20 mL), diluted with water (30 mL) and extracted with EtOAc (2×50 mL). The combined organic layer is washed with brine, dried over MgSO₄, filtered and evaporated. The residue is purified by flash chromatography on silica gel using 0-5% MeOH in DCM as eluent. The product containing fractions are evaporated to give IM-9a.

3,4-Dihydro-2H-pyrane (0.92 g; 10.9 mmol) is added dropwise to a solution of IM-9a (2.04 g; 9.31 mmol) and pTsOH (32.0 mg; 168 µmol) in DCM (5.0 mL) and the resulting mixture is stirred at rt for 2 h. Sat. NaHCO₃ solution is added and the mixture is passed through a phase separator. The organic phase is evaporated to give THP-protected IM-9a which is directly dissolved in THF (50 mL) and cooled to −78° C. 2.5 M nBuLi solution (3.8 mL in hexane; 9.50 mmol) is added dropwise and the mixture is stirred at −78° C. for 1 h. DMF (1.42 g; 19.4 mmol) is added dropwise and stirring is continued for 2 h at the same temperature. The reaction mixture is quenched with sat. NH₄Cl solution (50 mL) and extracted with EtOAc (3×50 mL). The combined organic layer is dried over MgSO₄, filtered and evaporated to give THP-protected IM-9b, which is directly dissolved in acetone (40 mL). 1 M HCl (30 mL; 30.0 mmol) is added and the reaction mixture is stirred at rt for 18 h. Sat. NaHCO₃ solution (80 mL) is added and the mixture is extracted with EtOAc (3×50 mL). The combined organic layer is washed with brine, dried over MgSO₄, filtered and evaporated. The residue is purified by flash chromatography on silica gel using 0-50% EtOAc in heptane as eluent. The product containing fractions are evaporated to give IM-9b.

To IM-9b (504 mg; 3.00 mmol) in DCM (15.0 mL) at 0° C. is added NEt₃ (2.0 mL; 13.8 mmol) followed by methanesulfonyl chloride (300 µL; 3.93 mmol) and the resulting mixture is stirred 0° C. for 30 min. Sat. NaHCO₃ solution (3.0 mL) is added and the solution is passed through a phase separator. The filtrate is evaporated and the residue purified by flash chromatography on silica gel using 0-70% EtOAc in heptane as eluent. The product containing fractions are evaporated to give B-1e.

To B-1e (430 mg; 1.75 mmol) in etane-1,2-diol (400 µL; 7.09 mmol) and triethylorthoformate (400 µL) is added tetrabutylammonium tribromide (81.0 mg; 168 µmol) and the resulting mixture is stirred at rt for 18 h in the dark. The reaction mixture is diluted with EtOAc (50 mL), washed with water (50 mL) and brine (50 mL). The organic layer is dried over MgSO₄, filtered and evaporated. The residue is purified by flash chromatography on silica gel using 0-20% EtOAc in heptane as eluent. The product containing fractions are evaporated to give C-1i.

Step 2: Synthesis of Compound 1-15

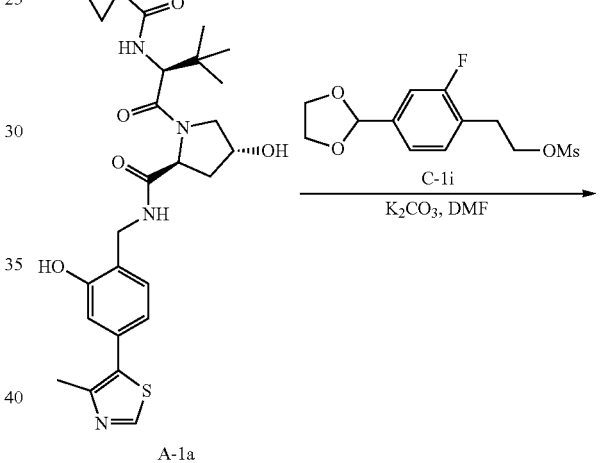

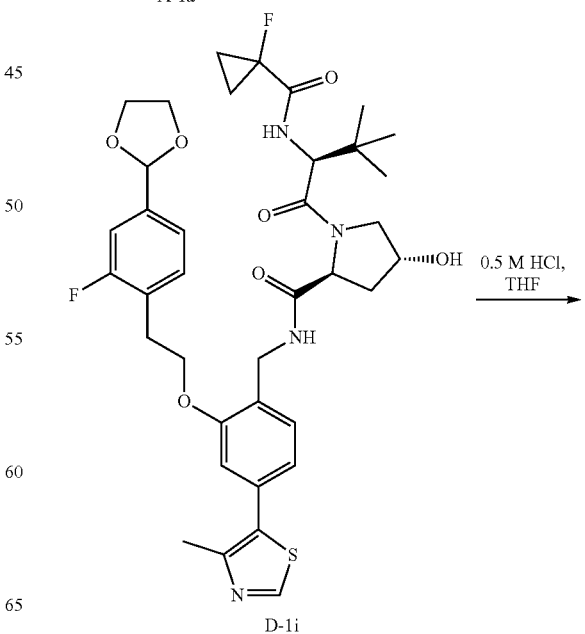

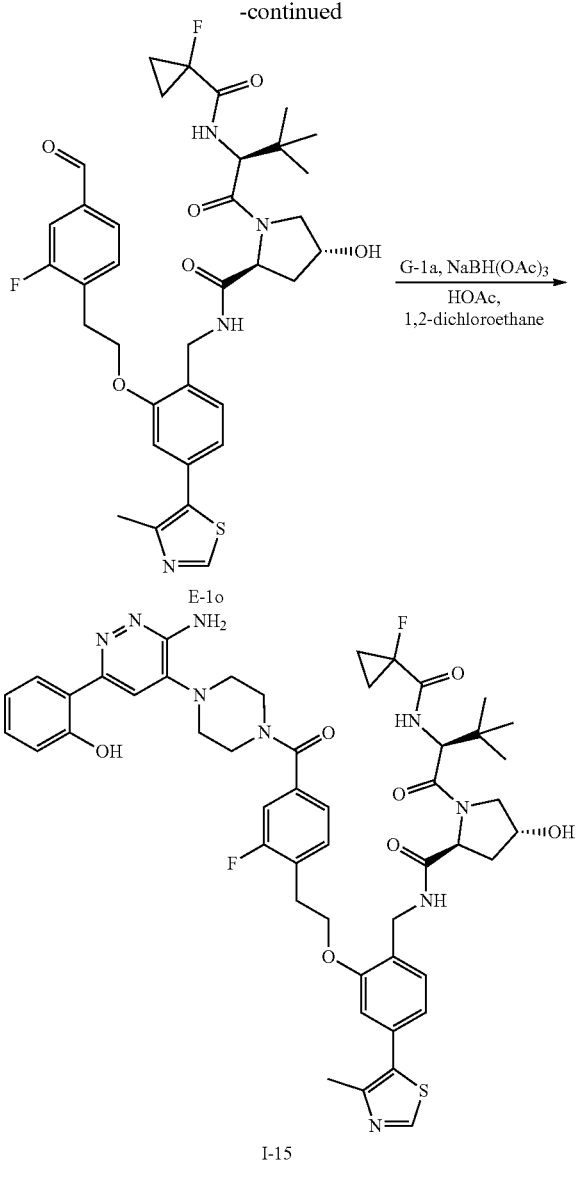

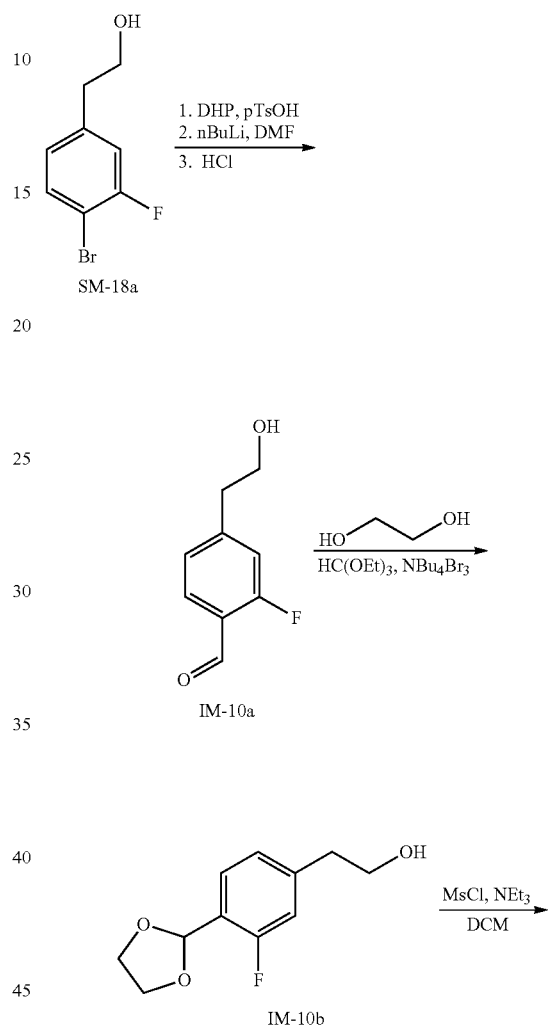

MeCN in 0.1% aq. NH₃ as eluent. The product containing fractions are freeze dried to give 1-15 (HPLC-MS: $t_{Ret.}$=4.70 min; MS (M+H)⁺=938; method D).

B 2.16 Experimental Procedures for the Synthesis of Compound 1-16

Step 1: Synthesis of Bifunctional Compound C-1j

To A-1a (104 mg; 195 µmol) in DMF (3.0 mL) is added K₂CO₃ (75.0 mg; 543 µmol) and C-1i (96.0 mg; 331 µmol) and the resulting mixture is stirred at 70° C. for 18 h. After cooling to rt, DCM (100 mL) and water (3.0 mL) is added and the solution is passed through a phase separator. The filtrate is evaporated and the residue purified by flash chromatography on silica gel using 0-10% MeOH in DCM as eluent. The product containing fractions are evaporated to give D-1 i (HPLC-MS: $t_{Ret.}$=1.65 min; MS (M+H)⁺=727; method C).

To D-1i (78.1 mg; 107 µmol) in THF (1.5 mL) is added 0.5 M HCl (1.5 mL) and the mixture is stirred at 75° C. for 45 min. After cooling to rt the mixture is concentrated under reduced pressure, the residue (→E-1o) is taken up in 1,2-dichloroethane (3.0 mL) and G-1a (45.0 mg; 131 µmol) is added followed by NEt₃ (500 µL; 3.46 mmol), MgSO₄ and NaBH(OAc)₃ (100 mg; 472 µmol). The resulting mixture is stirred at rt for 16 h, filtered and evaporated. The residue is taken up and is purified by RP HPLC under acidic conditions using 0-60% MeCN in 0.1% aq. formic acid as eluent followed by RP HPLC under basic conditions using 5-95%

3,4-Dihydro-2H-pyrane (0.92 g; 10.9 mmol) is added dropwise to a solution of SM-18a (1.99 g; 9.08 mmol) and pTsOH (10.0 mg; 52.6 µmol) in DCM (5.0 mL) and the resulting mixture is stirred at rt for 2 h. Sat. NaHCO₃ solution is added and the mixture is passed through a phase separator. The organic phase is evaporated to give THP-protected SM-18a which is directly dissolved in THF (50 mL) and cooled to −78° C. 2.5 M nBuLi solution (3.8 mL in hexane; 9.50 mmol) is added dropwise and the mixture is stirred at −78° C. for 1 h. DMF (1.42 g; 19.4 mmol) is added dropwise and stirring is continued for 2 h at the same temperature. The reaction mixture is quenched with sat. NH$_4$Cl solution (50 mL) and extracted with EtOAc (3×50 mL). The combined organic layer is dried over MgSO$_4$, filtered and evaporated to give THP-protected IM-10a, which is directly dissolved in acetone (40 mL). 1 M HCl (30 mL; 30.0 mmol) is added and the reaction mixture is stirred at rt for 18 h. Sat. NaHCO$_3$ solution (80 mL) is added and the mixture is extracted with EtOAc (3×50 mL). The combined organic layer is washed with brine, dried over MgSO$_4$, filtered and evaporated. The residue is purified by flash chromatography on silica gel using 0-50% EtOAc in heptane as eluent. The product containing fractions are evaporated to give IM-10a.

To IM-10a (508 mg; 3.02 mmol) in ethane-1,2-diol (1.6 mL; 28.4 mmol) and triethylorthoformate (1.6 mL) is added tetrabutylammonium tribromide (324 mg; 672 μmol) and the resulting mixture is stirred at rt for 18 h in the dark. The reaction mixture is diluted with EtOAc (50 mL), washed with water (50 mL) and brine (50 mL). The organic layer is dried over MgSO$_4$, filtered and evaporated. The residue is purified by flash chromatography on silica gel using 0-20% EtOAc in heptane as eluent. The product containing fractions are evaporated to give IM-10b.

To IM-10b (287 mg; 1.35 mmol) in DCM (10.0 mL) at 0° C. is added NEt$_3$ (1.0 mL; 6.92 mmol) followed by methanesulfonyl chloride (200 μL; 2.62 mmol) and the resulting mixture is stirred 0° C. for 30 min. Sat. NaHCO$_3$ solution (3.0 mL) is added and the solution is passed through a phase separator. The filtrate is evaporated and the residue purified by flash chromatography on silica gel using 0-70% EtOAc in heptane as eluent. The product containing fractions are evaporated to give C-1j.

Step 2: Synthesis of Compound 1-16

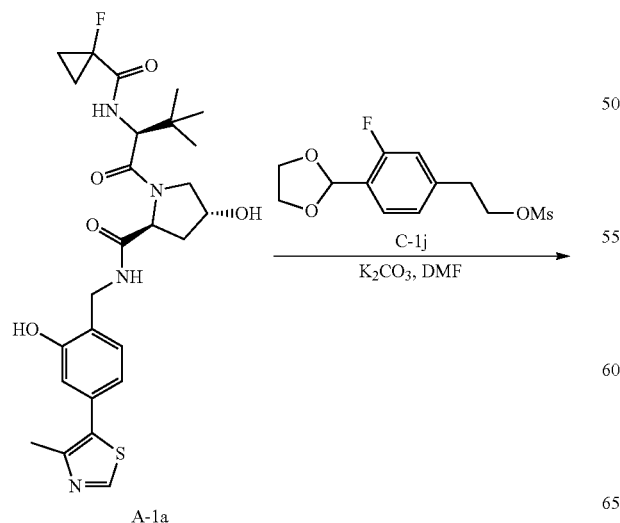

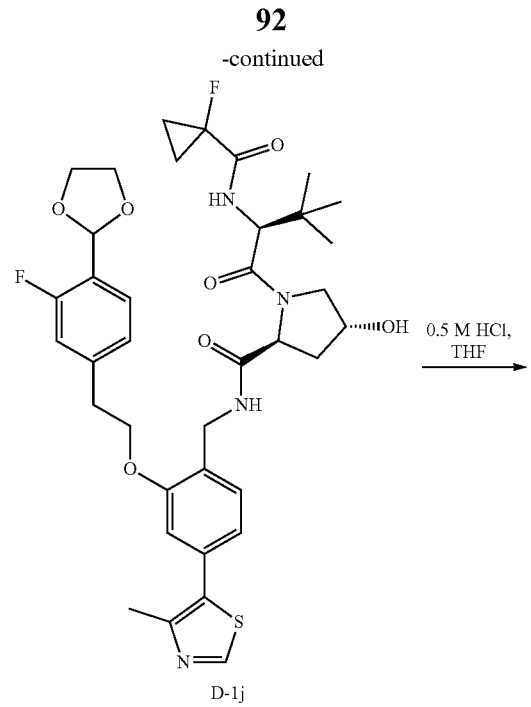

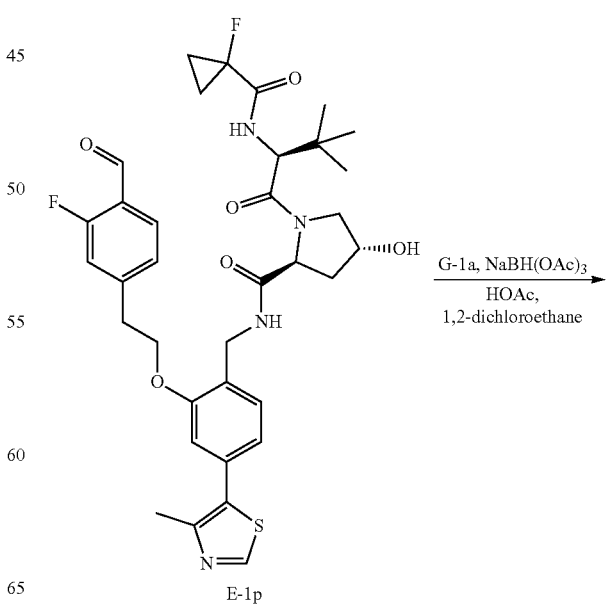

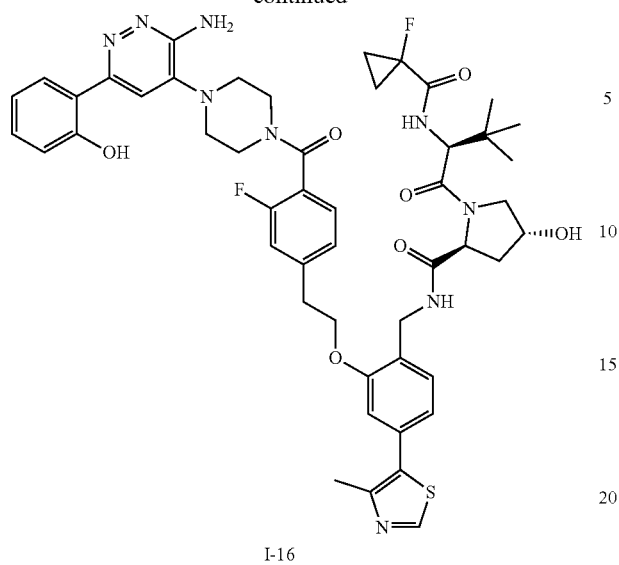

I-16

To A-1a (218 mg; 409 µmol) in DMF (3.0 mL) is added K$_2$CO$_3$ (160 mg; 1.16 mmol) and C-1j (106 mg; 365 µmol) and the resulting mixture is stirred at 100° C. for 18 h. After cooling to rt, DCM (100 mL) and water (3.0 mL) is added and the solution is passed through a phase separator. The filtrate is evaporated and the residue purified by flash chromatography on silica gel using 0-10% MeOH in DCM as eluent. The product containing fractions are evaporated to give D-1j (HPLC-MS: t$_{Ret.}$=1.64 min; MS (M+H)$^+$=727; method C).

To D-1j (52.9 mg; 72.8 µmol) in THF (1.0 mL) is added 0.5 M HCl (1.0 mL) and the mixture is stirred at 75° C. for 45 min. After cooling to rt the mixture is concentrated under reduced pressure, the residue (→E-1p) is taken up in 1,2-dichloroethane (3.0 mL) and G-1a (40.0 mg; 116 µmol) is added followed by NEt$_3$ (400 µL; 2.77 mmol), MgSO$_4$ and NaBH(OAc)$_3$ (80.0 mg; 377 µmol). The resulting mixture is stirred at rt for 16 h, filtered and evaporated.

The residue is taken up and is purified by RP HPLC under acidic conditions using 0-60% MeCN in 0.1% aq. formic acid as eluent followed by RP HPLC under basic conditions using 5-95% MeCN in 0.1% aq. NH$_3$ as eluent. The product containing fractions are freeze dried to give 1-16 (HPLC-MS: t$_{Ret.}$=4.60 min; MS (M+H)$^+$=938; method D).

B 2.17 Experimental Procedures for the Synthesis of Compound 1-17

Step 1: Synthesis of Bifunctional Compound C-1k

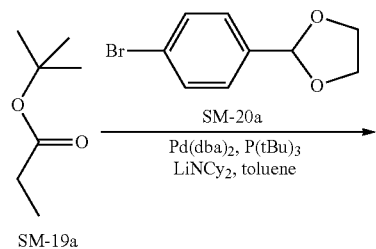

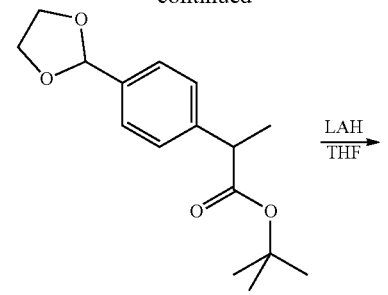

IM-11a

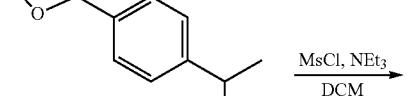

IM-11b

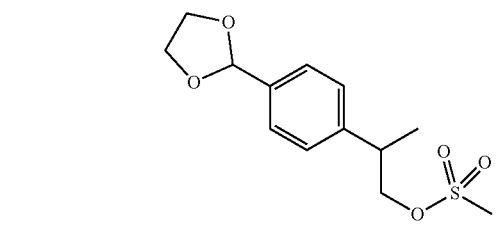

C-1k

To dicyclohexylamine (1.87 g; 10.3 mmol) in toluene (8.0 mL) is added 2.5 M nBuLi solution (4.2 mL in hexane; 10.4 mmol) under argon and the resulting mixture is stirred at rt for 20 min. SM-19a (1.19 g; 9.14 mmol) is added and stirring is continued at rt for 10 min. This mixture is added to Pd(dba)$_2$ (206 mg; 358 µmol) and SM-20a (1.84 g; 8.03 mmol) in a microwave vial under argon. P(tBu)$_3$ (400 µL of a 1 M solution in toluene; 400 µmol) is added, the vial is sealed and stirred at rt for 18 h. The reaction mixture is evaporated and the residue is purified by flash chromatography on silica gel using 0-20% EtOAc in heptane as eluent. The product containing fractions are evaporated to give IM-11a as a racemate.

To IM-11a (1.62 g; 5.82 mmol) in THF (10 mL) at 0° C. is added LAH (10.0 mL of a 1.0 M solution; 10.0 mmol) dropwise. The resulting mixture is stirred at 0° C. for 2 h, then quenched with Na$_2$SO$_4$·10 H$_2$O and stirred for 30 min. The mixture is filtered through celite, washed with THF and DCM and the filtrate is evaporated. The residue is purified by flash chromatography on silica gel using 0-70% EtOAc in heptane as eluent. The product containing fractions are evaporated to give IM-1b.

To IM-11b (531 mg; 2.55 mmol) in DCM (15.0 mL) at 0° C. is added NEt$_3$ (2.0 mL; 13.8 mmol) followed by methanesulfonyl chloride (350 µL; 4.58 mmol) and the resulting mixture is stirred 0° C. for 30 min. Sat. NaHCO$_3$ solution (3.0 mL) is added and the solution is passed through a phase separator. The filtrate is evaporated and the residue purified by flash chromatography on silica gel using 0-70% EtOAc in heptane as eluent. The product containing fractions are evaporated to give C-1 k.

Step 2: Synthesis of Compound 1-17

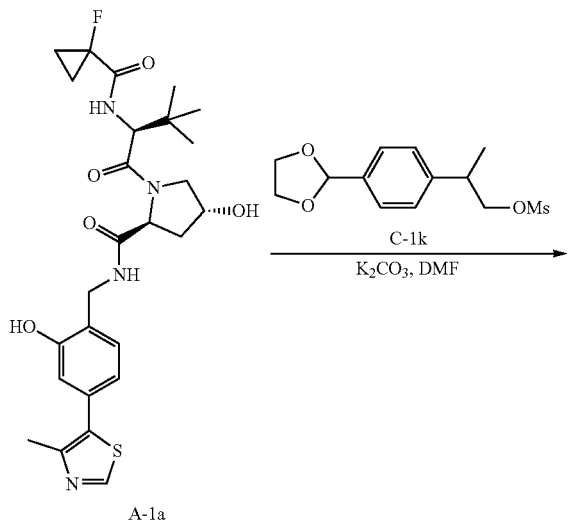

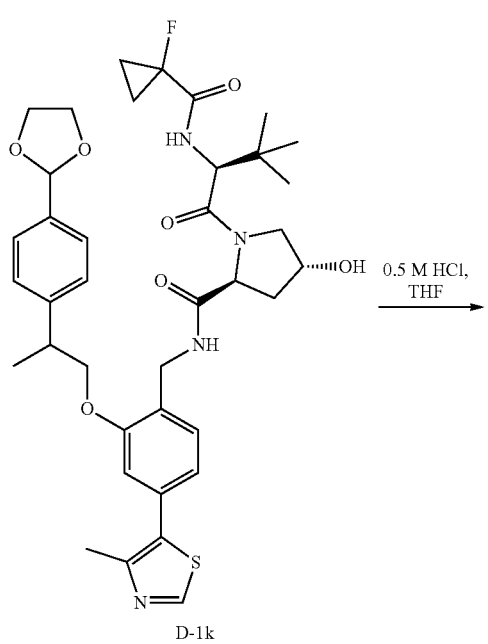

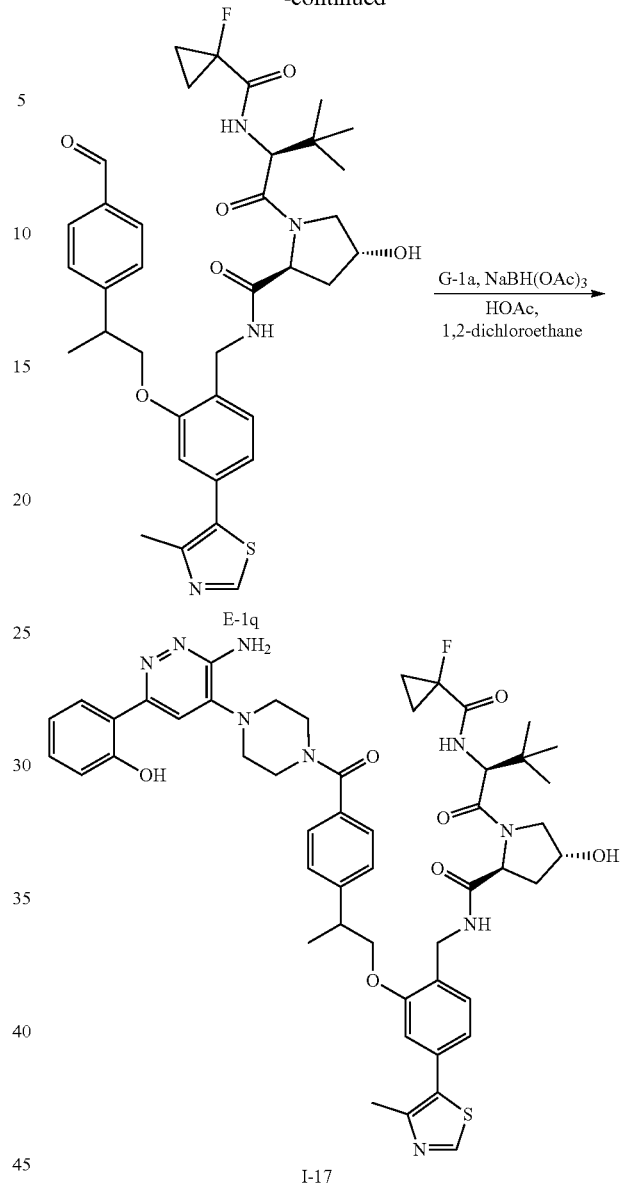

To A-1a (108 mg; 409 µmol) in DMF (3.0 mL) is added $K_2CO_3$ (67.0 mg; 485 µmol) and C-1 k (76.0 mg; 265 µmol) and the resulting mixture is stirred at 80° C. for 18 h. After cooling to rt, DCM (100 mL) and water (3.0 mL) is added and the solution is passed through a phase separator. The filtrate is evaporated and the residue purified by flash chromatography on silica gel using 0-10% MeOH in DCM as eluent. The product containing fractions are evaporated to give D-1 k as a diastereomeric mixture (HPLC-MS: $t_{Ret.}$=1.67 min; MS (M+H)$^+$=723; method C).

To D-1 k (69.9 mg; 96.7 µmol) in THF (1.0 mL) is added 0.5 M HCl (1.0 mL) and the mixture is stirred at 75° C. for 45 min. After cooling to rt the mixture is concentrated under reduced pressure, the residue (→E-1q) is taken up in 1,2-dichloroethane (4.0 mL) and G-1a (45.0 mg; 131 µmol) is added followed by $NEt_3$ (500 µL; 3.46 mmol), $MgSO_4$ and NaBH(OAc)$_3$ (100.0 mg; 472 µmol). The resulting mixture is stirred at rt for 16 h, filtered and evaporated. The residue is taken up and is purified by RP HPLC under acidic conditions using 0-60% MeCN in 0.1% aq. formic acid as eluent followed by RP HPLC under basic conditions using 5-95% MeCN in 0.1% aq. NH$_3$ as eluent. The product containing fractions are freeze dried to give 1-17 as a diastereomeric mixture (HPLC-MS: t$_{Ret.}$=4.70 min; MS (M+H)$^+$=934; method D).

B 2.18 Experimental Procedures for the Synthesis of Compound 1-18

Step 1: Synthesis of Bifunctional Compound C-2b

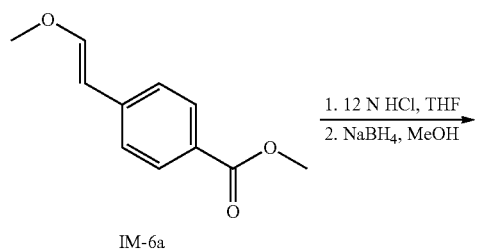

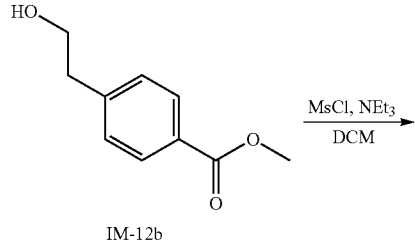

chromatography on silica gel using 0-30% EtOAc in heptane as eluent. The product containing fractions are evaporated, taken up in Et$_2$O (50 mL) and washed with 1 M HCl. The organic layer is dried over MgSO$_4$, filtered and evaporated to give pure IM-12b (R$_f$=0.38; heptane:EtOAc=1:1).

To IM-12b (565 mg; 3.14 mmol) in DCM (15.0 mL) at 0° C. is added NEt$_3$ (2.0 mL; 13.8 mmol) followed by methanesulfonyl chloride (250 µL; 3.27 mmol) and the resulting mixture is stirred 0° C. for 2 h. Sat. NaHCO$_3$ solution (3.0 mL) is added and the solution is passed through a phase separator. The filtrate is evaporated and the residue purified by flash chromatography on silica gel using 0-70% EtOAc in heptane as eluent. The product containing fractions are evaporated to give C-2b.

Step 2: Synthesis of Compound 1-18

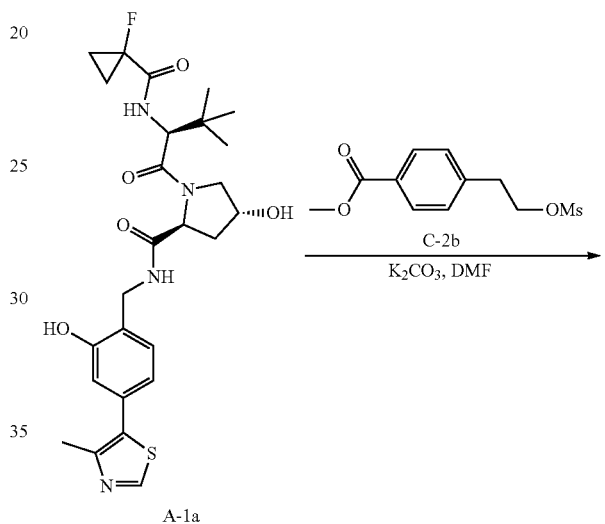

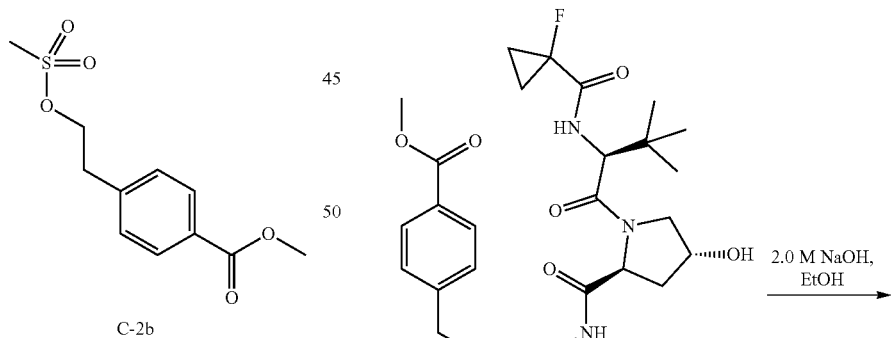

To the E:Z mixture of IM-6a (1.45 g; 7.54 mmol) in THF (27 mL) is added 12 M HCl (4.0 mL; 48.0 mmol) in THF (8.0 mL) at rt and the resulting mixture is stirred at this temperature for 4 h. Sat. NaHCO$_3$ solution is added and the mixture is extracted with EtOAc. The combined organic layer is washed with brine, dried over MgSO$_4$, filtered and evaporated. The residual aldehyde is directly dissolved in MeOH (30 mL) and cooled to 0° C. NaBH$_4$ (660 mg; 17.4 mmol) is added and the mixture is stirred for 30 min. The reaction mixture is diluted with MeOH and concentrated under reduced pressure. The residue is purified by flash

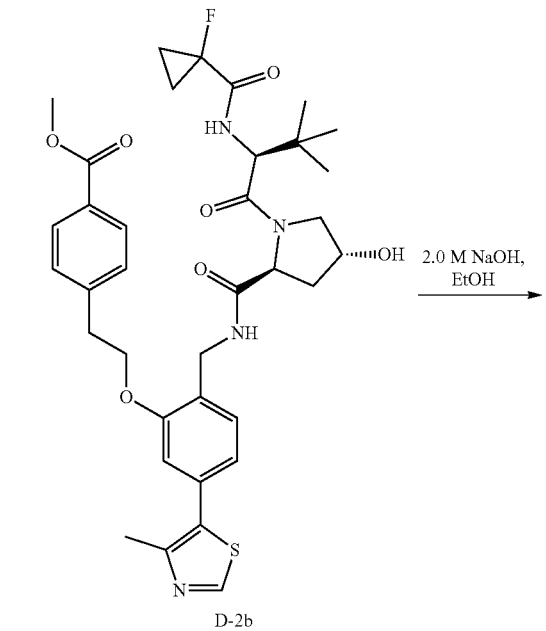

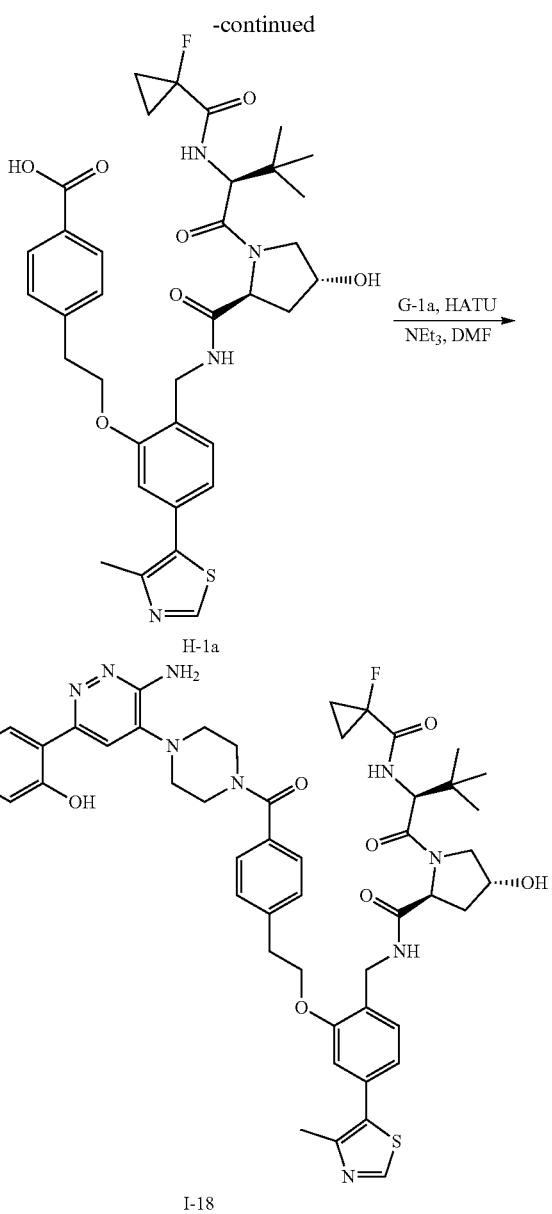

conditions using 5-95% MeCN in 0.1% aq. $NH_3$ as eluent. The product containing fractions are freeze dried to give 1-18 (HPLC-MS: $t_{Ret.}$=1.47 min; MS $(M+H)^+$=934; method C).

Example of Pharmaceutical Formulation

Ampoule Solution

| active substance according to formula (I) | 50 mg |
|---|---|
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The following Examples describe the biological activity of the compounds according to the invention, without restricting the invention to these Examples.

SPR Binding Studies

SPR experiments are performed on Biacore 8K or T200 instruments (GE Healthcare). Immobilization of target proteins: Immobilization of target proteins is carried out at 25° C. on a CM5 chip using amine coupling (EDC/NHS, GE Healthcare or XANTEC) in HBS-P+ running buffer, containing 2 mM tris(2-carboxyethyl) phosphine hydrochloride (TCEP), pH 7.4. Following activation of the surface with EDC/NHS (contact time 600 s, flow rate 10 µL/min), the target bromodomains ($SMARCA2^{BD}$, $SMARCA4^{BD}$ prepared at 0.5-0.7 mg/mL or PBRM1BD5 at 0.005 mg/mL in coupling buffer consisting of 10 mM Na-Acetate pH 6.5, 0.005% Tween-20 and 50 µM PFI-322, are coupled to a density of 1000-20000 Response Units (RU) ($SMARCA2^{BD}$ and $SMARCA4^{BD}$) or 100-2000 RU ($PBRM1^{BD}5$). Surfaces are deactivated using 1 M ethanolamine. For VHL target protein, streptavidin (Sigma Aldrich) (prepared at 1 mg/mL in 10 mM sodium acetate coupling buffer, pH 5.0) is first immobilized by amine coupling to a density of 1000-10000 RU), after which biotinylated VCB complex (2.8 µM in running buffer) is streptavidin coupled to a density of 1000-20000 RU. The reference surface consists of an EDC/NHS-treated surface deactivated with 1 M ethanolamine. Biotinylated VCB is prepared as follows:

Cloning of VCB-AviTag Complex and Expression and Purification of VCB-AviTag™ Complexes.

A synthetic DNA sequence (gBlock) is purchased from IDT, which encodes for ElonginB (1-104) followed by a short spacer and AviTag™ sequence at the C-terminus (final translated protein sequence: MDVFLMIRRHKT-TIFTDAKESSTVFELKRIVEGILKRPPDE QRLYKDDQLL-DDGKTLGECGFTSQTARPQAPATVGLAFRADDTFE-ALCIEPFSSPPELPD VMKgspaggglndifeaqkiewhe) (SEQ ID NO.:1). This DNA is sub-cloned into the NcoI/HindIII sites of a plasmid (pIVMO2, pCDFDUET-1b, Strep$^r$) (Peränen, J.; Rikkonen, M.; Hyvönen, M.; Kääriäinen, L. Anal Biochem 1996, 236, 371) which already contains a sequence that encodes for ElonginC (17-112). The final plasmid is co-transformed into BL21(DE3) E. coli cells along with the plasmid for expression of VHL (54-213) with an N-terminal His6 purification tag and TEV cleavage site To A-1a (200 mg; 375 µmol) in DMF (6.0 mL) is added $K_2CO_3$ (107 mg; 774 µmol) and C-2b (133 mg; 515 µmol) and the resulting mixture is stirred at 70° C. for 18 h. After cooling to rt, DCM and water is added and the solution is passed through a phase separator. The filtrate is evaporated and the residue purified by flash chromatography on silica gel using 0-10% MeOH in DCM as eluent. The product containing fractions are evaporated to give D-2b (HPLC-MS: $t_{Ret.}$=1.66 min; MS $(M+H)^+$=695; method C).

To D-2b (49.1 mg; 70.7 µmol) in EtOH (1.0 mL) is added 2.0 M NaOH in water (1.0 mL; 2.00 mmol) and the mixture is stirred at 50° C. for 1 h. After cooling to rt the mixture is acidified with 1 M HCl to pH 5 and concentrated under reduced pressure. The residue (→H-1a) is taken up in DMF (3.0 mL) and G-1a (24.0 mg; 69.7 µmol) is added followed by HATU (50.0 mg; 131 µmol) and $NEt_3$ (150 µL; 1.04 mmol). The resulting mixture is stirred at rt for 18 h, filtered and evaporated. The residue is taken up and is purified by RP HPLC under acidic conditions using 5-95% MeCN in 0.1% aq. formic acid as eluent followed by RP HPLC under basic (pHAT4 (Peränen, J.; Rikkonen, M.; Hyvönen, M.; Kääriäinen, L. *Anal Biochem* 1996, 236, 371) Amp$^r$). The VCB-AviTag™ complex (VHL$^{54-213}$:ElonginC$^{17-112}$:ElonginB$^{1-104}$-AviTag) is co-expressed and purified, including removal of the His6 tag using TEV protease, as previously described for the VCB complex (Gadd, M. S.; Testa, A.; Lucas, X.; Chan, K. H.; Chen, W.; Lamont, D. J.; Zengerle, M.; Ciulli, A. *Nat Chem Biol* 2017, 13, 514). The purified complex is stored in 20 mM HEPES, 100 mM sodium chloride and 1 mM TCEP, pH 7.5.

Expression and Purification of GST-BirA.

A plasmid (pGEX6P-1, Amp$^r$) containing the BirA enzyme as an N-terminal GST-fusion protein with a TEV protease cleavage site (gift of the MRC PPU Reagents and Services, University of Dundee, Scotland; Genbank: M10123) is transformed into BL21 (DE3) cells and expressed and purified based on a modified literature procedure (Fairhead, M.; Howarth, M. *Methods Mol Biol* 2015, 1266, 171). Briefly, a 10 mL starter culture of LB medium containing ampicillin (100 µg/mL) and D-glucose (0.4% v/v) is inoculated from a single colony and grown overnight at 37° C. in a shaking incubator (200 rpm). The starter culture (8 mL) is added a 1 L culture of TB containing ampicillin (100 µg/mL) and D-glucose (0.8% v/v) and grown at 37° C. for 3 h. At an optical density (A$_{600}$) of approximately 1.1, the temperature is lowered to 23° C. and expression is induced using isopropyl β-D-1-thiogalactopyranoside (IPTG) (0.4 mM) for approximately 16 h at 23° C. (180 rpm). Cells are harvested by centrifugation (20 min, 4200 rpm) in a JC-M6 centrifuge (Beckman Coulter). Cells are resuspended on ice in 50 mL of GST buffer consisting of 50 mM HEPES, 500 mM sodium chloride, 5% v/v glycerol and 5 mM DTT, supplemented with cOmplete™ protease inhibitor (Roche) and lysed using a Stansted Cell Disruptor (Stansted Fluid Power). Lysate is centrifuged (20,000 rpm, 4'C) in an Avanti J-25 centrifuge (Beckman Coulter), filtered (0.45 µM syringe filter) and passed twice over a Glutathione Sepharose 4B resin (5 mL bed volume) (GE Healthcare) pre-equilibrated in GST Buffer. The column is washed with GST Buffer (40 mL) and the protein eluted in GST Buffer containing 20 mM L-glutatione (Sigma Aldrich) (20 mL). The eluted GST-BirA protein is purified directly by SEC on a Superdex® 75 16/60 Hiload® gel filtration column on an AKTApure™ system (GE Healthcare) in the following buffer: 20 mM HEPES, 150 mM sodium chloride, pH 7.5 and the protein concentrated (0.4 mg/mL), snap-frozen in N$_2$ (liq.) and stored at -80° C.

Site-Specific Biotinylation of VCB-AviTag™ Using GST-BirA.

Site-specific biotinylation of the VCB-AviTag™ is carried out using GST-BirA as described (Fairhead, M.; Howarth, M. *Methods Mol Biol* 2015, 1266, 171). The final biotinylated complex ('VHL-biotin') is concentrated to 100 µM, snap frozen in N$_2$ (liq.) and stored at -80° C.

Interaction experiments: All interaction experiments are performed at 6° C. in running buffer consisting of 20 mM tris(hydroxymethyl)aminomethane (TRIS), 150 mM potassium chloride, 2 mM magnesium chloride, 2 mM tris(2-carboxyethyl)phosphine hydrochloride (TCEP), 0.005% TWEEN 20, 1% dimethyl sulfoxide; pH 8.3.

Data analysis: Sensorgrams from reference surfaces and blank injections are subtracted from the raw data prior to data analysis, using Biacore™ T200 or Biacore™ 8K evaluation software. Sensorgrams recorded at different compound concentrations in multi-cycle experiments are fitted using a 1:1 interaction model, with a term for mass-transport included.

Protein Degradation Assays

For the protein degradation assay, A549 (NSCLC) cells are used in which the inactivating SMARCA4 mutation has been corrected to wild type, such that the cells express both SMARCA2 and SMARCA4. 35000 cells in F12K Medium +10% FBS (100 µL/well) are seeded in a Greiner 96 well F-bottom plate and incubated at 37° C. overnight. Compounds are added from DMSO stock solution using ECHO Access™ workstation or HP D300 Digital Dispenser and cells are incubated at 37° C. for 18 h. Medium is removed, cells are washed with PBS, PBS is removed and 30 µL cold Lysis Buffer (1% Triton, 350 mM KCl, 10 mM Tris, Halt Phosphatase-Protease Inhibitors, 10 mM DTT, Benzonase 0.5 µL/mL) is added to each well. Cells are lysed for 20 min at 4° C. on a bioshake at 800 rpm before insoluble debris is pelleted by centrifugation for 20 min at 4000 rpm at 4° C. The supernatant is transferred to a fresh PCR plate. SMARCA2 levels are determined on a WES capillary electrophoresis instrument (Proteinsimple) using rabbit anti-SMARCA2 antibody (1:25, Sigma #HPA029981), SMARCA4 antibody (CellSignaling #49360, 1:25), PBRM1 antibody (Bethyl #A301-591A-M, 1:40) and anti-GAPDH antibody (1:100, Abcam #ab9485) for normalization.

The compounds 1-1 to 1-18 according to the invention have been tested in the above described assay. The results are listed in table 1. The majority of the compounds show degradation of SMARCA2 and SMARCA4 protein in A549 cells with DC$_{50}$ in the range of 10-1000 nM (i.e. compound concentration at which half maximal degradation is achieved). The D$_{max}$ represents the efficiency of degradation and gives the maximal amount of degraded protein relative to initial levels. The majority of the compounds reach degradation levels >80%.

TABLE 1

Degradation of SMARCA2 and SMARCA4 in A549 cells

| # | DC$_{50}$ SMARCA2 [nM] | D$_{max}$ SMARCA2 [%] | DC$_{50}$ SMARCA4 [nM] | D$_{max}$ SMARCA4 [%] |
|---|---|---|---|---|
| I-1 | 450 | 45 | 1245 | 70 |
| I-2 | 67 | 91 | 117 | 93 |
| I-3 | 5000 | | 2044 | 100 |
| I-4 | 1000 | 70 | 735 | 87 |
| I-5 | 2543 | 89 | 1927 | 84 |
| I-6 | 172 | 83 | 219 | 89 |
| I-7 | 12 | 98 | 16 | 97 |
| I-8 | 56 | 88 | 168 | 59 |
| I-9 | 236 | 85 | 170 | 83 |
| I-10 | 41 | 99 | 26 | 99 |
| I-11 | 26 | 99 | 16 | 100 |
| I-12 | ~1000 | 40 | | |
| I-13 | 189 | 88 | 634 | 97 |
| I-14 | 58 | 90 | 25 | 92 |
| I-15 | 84 | 92 | 168 | 90 |
| I-16 | 55 | 95 | 33 | 95 |
| I-17 | 118 | 87 | 78 | 100 |
| I-18 | 525 | 98 | 188 | 81 |

Proliferation Assays

1000 NCI-H1568 (NSCLC) (ATCC CRL-5876) cells/well are seeded in 384 well plates. After overnight incubation, compounds are added to the cells at logarithmic dose series using the HP Digital Dispenser D300 (Tecan), normalising for added DMSO. 1 day and 8 days after seeding, cellular ATP content is measured using CellTiterGlo® Assay (Promega). Concentrations of half-maximal inhibition are derived using four parameter non-linear regression using GraphPad Prism software.

The invention claimed is:

1. A compound of formula (I)

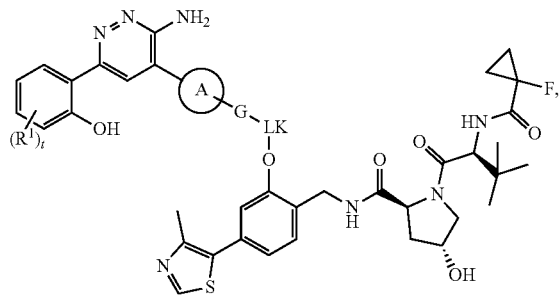

(I)

wherein
each $R^1$ is independently selected from the group consisting of halogen, —CN, —CF$_3$, —OCF$_3$, C$_{1-3}$alkyl and C$_{1-3}$ alkoxy;
t is 0, 1 or 2;
ring A is selected from the group consisting of C$_{4-7}$cycloalkylene, C$_{4-7}$ cycloalkenylene and 4-7 membered nitrogen-containing heterocyclylene, wherein said C$_{4-7}$cycloalkylene, C$_{4-7}$cycloalkenylene and 4-7 membered nitrogen-containing heterocyclylene is optionally substituted with one or more, identical or different substituent(s) selected from the group consisting of halogen, C$_{1-4}$alkyl and oxo;
G is selected from the group consisting of a bond, —NH—, —N(C$_{1-4}$alkyl)- and —O—;
LK is —U—V—W—, wherein U binds to G;
U is selected from the group consisting of a bond, carbonyl, C$_{1-12}$alkylene, C$_{6-10}$arylene, 5-10 membered heteroarylene, —(CH$_2$)$_n$-O- and —O(CH$_2$)$_n$—;

V is selected from the group consisting of a bond, carbonyl, $C_{1-12}$alkylene, $C_{6-10}$arylene, 5-10 membered heteroarylene, —$(CH_2)_nO$— and —$O(CH_2)_n$—;

W is selected from the group consisting of a bond, carbonyl, $C_{1-12}$alkylene, $C_{6-10}$arylene, 5-10 membered heteroarylene, —$(CH_2)$~O- and —$O(CH_2)_n$—;

wherein each of said $C_{6-10}$arylene and of said 5-10 membered heteroarylene in U, V and W is optionally independently substituted with one to three, identical or different substituent(s) selected from the group consisting of halogen, $C_{1-4}$alkyl, $C_{1-4}$alkoxy and —CN;

wherein at least one of U, V and W is different from the other two;

wherein U and W are not —O— if V is —O—;

each n is independently selected from 0 to 8;

or a salt thereof.

2. A compound or salt according to claim 1, wherein $R^1$ is halogen;

t has the value 1 or 2.

3. A compound or salt according to claim 2, wherein $R^1$ is fluorine;

t has the value 1 or 2.

4. A compound or salt according to claim 1, wherein t is 0.

5. A compound or salt according to claim 1, wherein ring A is selected from the group consisting of

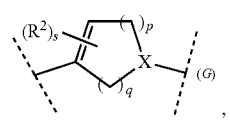
(i)

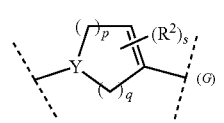
and
(ii)

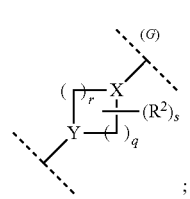
;
(iii)

each p is independently selected from 0, 1 and 2;

each q is independently selected from 1 and 2;

r is 1, 2 or 3;

each s is independently selected from 0, 1 or 2;

each $R^2$ is independently selected from the group consisting of halogen, $C_{1-4}$alkyl and oxo;

each X is independently >CH— or >N—; and each Y is independently >CH— or >N—.

6. A compound or salt according to claim 5, wherein ring A is

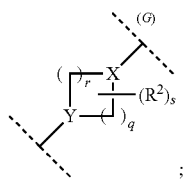
;
(iii)

q is independently selected from 1 and 2;

r is 1, 2 or 3;

s is independently selected from 0, 1 or 2;

each $R^2$ is independently selected from the group consisting of halogen, $C_{1-4}$alkyl and oxo;

X is >CH— or >N—; and

Y is >CH— or >N—.

7. A compound or salt according to claim 5, wherein s is 0.

8. A compound or salt according to claim 5, wherein ring A is selected from the group consisting of

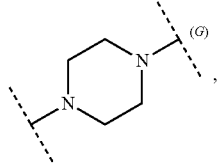
,
a)

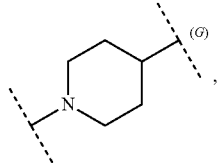
,
b)

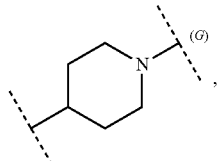
,
c)

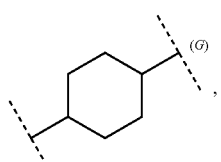
,
d)

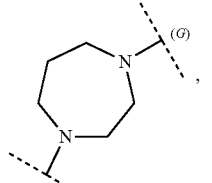
,
e)

-continued
f)
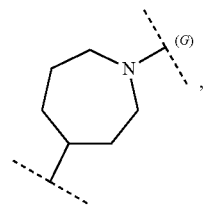
g)
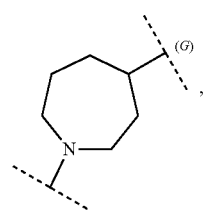
h)
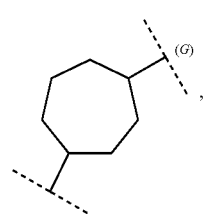
i)
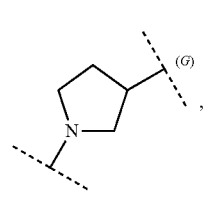
j)
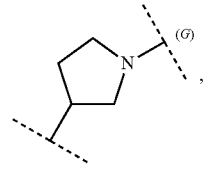
k)
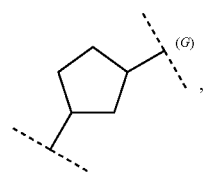
l)
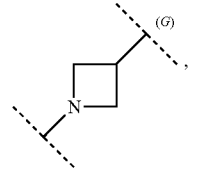
m)
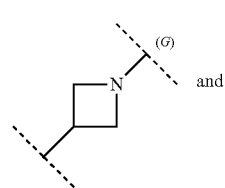 and
-continued
n)
wherein each ring a) to n) is optionally substituted by one or two substituent(s) independently selected from the group consisting of halogen, $C_{1-4}$alkyl and oxo.
9. A compound or salt according to claim 8, wherein ring A is selected from the group consisting of
a)
b)
c)
d)
e)
f)

-continued g)
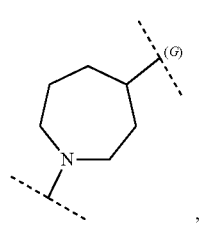, h)
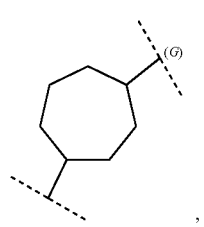, i)
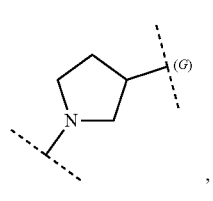, j)
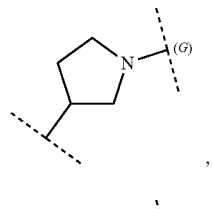, k)
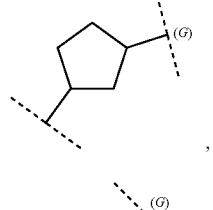, l)
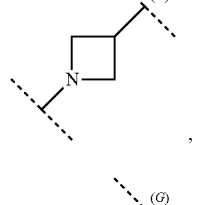, m)
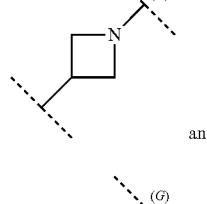

and n)
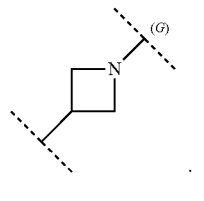

10. A compound or salt according to claim 9, wherein ring A is selected from the group consisting of a)

and c)

11. A compound or salt according to claim 10, wherein ring A is a)

12. A compound or salt according to claim 1, wherein G is a bond.

13. A compound or salt according to claim 1, wherein LK is —U—V—W—, wherein U binds to G;
U is selected from the group consisting of carbonyl, $C_{1-12}$alkylene and (G) —$(CH_2)_n$O—;
V is selected from the group consisting of a bond, $C_{1-12}$alkylene, $C_{6-10}$arylene, 5-10 membered heteroarylene and (U) —$(CH_2)_n$O—;
W is selected from the group consisting of a bond, $C_{1-12}$alkylene and (V) —O$(CH_2)_n$—;
wherein each of said $C_{6-10}$arylene in V is optionally substituted with one halogen;
wherein at least one of U, V and W is different from the other two;
wherein U and W are not —O— if V is —O—;
each n is independently selected from 0 to 8.

14. A compound or salt according to claim 13, wherein LK is selected from the group consisting of

,

,

,

111
-continued

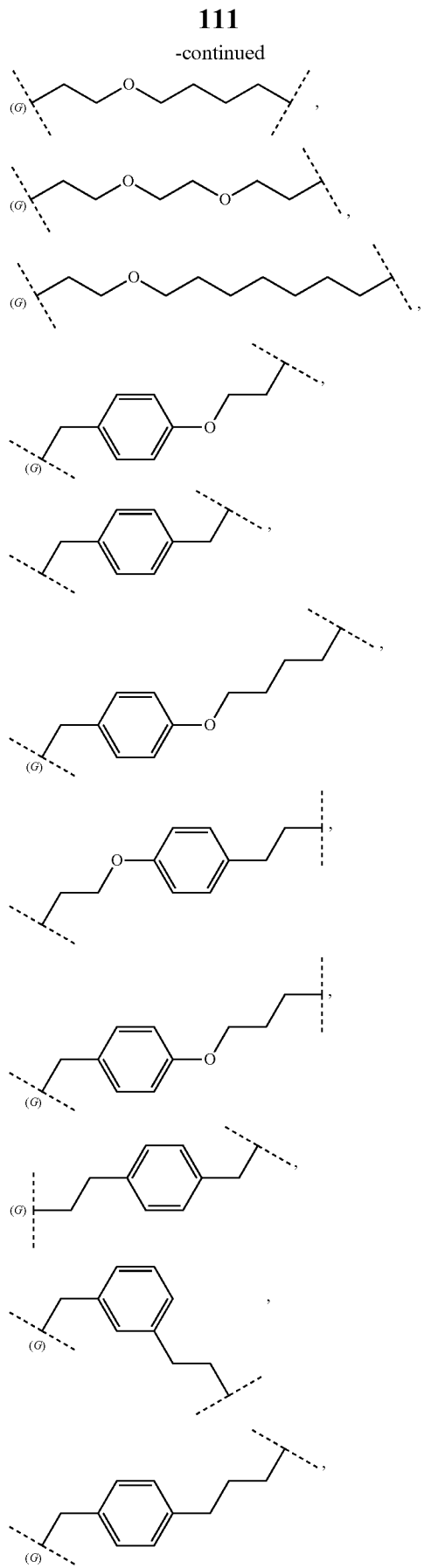

112
-continued

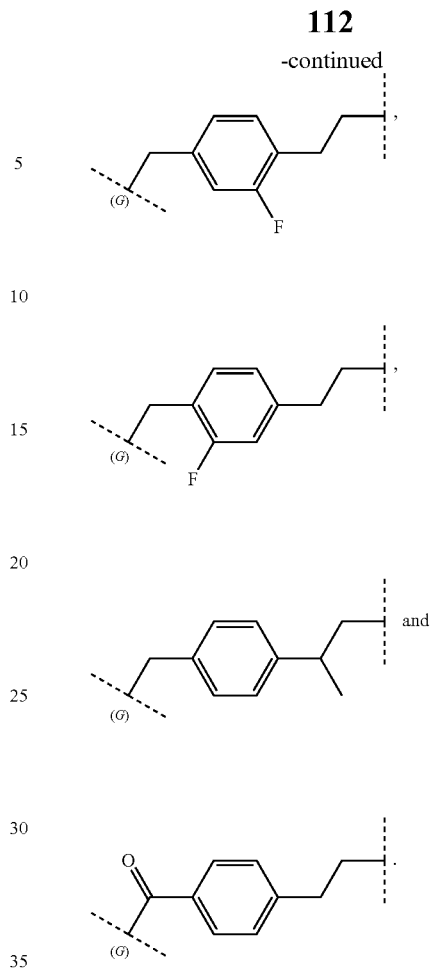

15. A method for the treatment of a disease and/or condition wherein the degradation of SMARCA2 and/or SMARCA4 is of therapeutic benefit comprising administering a therapeutically effective amount of a compound of claim 1 or a pharmaceutically acceptable salt thereof to a human being, wherein the disease and/or condition wherein the degradation of SMARCA2 and/or SMARCA4 is of therapeutic benefit is non-small cell lung cancer (NSCLC).

16. A method for the treatment of cancer comprising administering a therapeutically effective amount of a compound of claim 1 or a pharmaceutically acceptable salt thereof to a human being, wherein the cancer is non-small cell lung cancer (NSCLC).

17. A method according to claim 15, wherein the compound—or a pharmaceutically acceptable salt thereof—is administered before, after or together with at least one other pharmacologically active substance.

18. A method according to claim 15, wherein the compound—or a pharmaceutically acceptable salt thereof—is administered in combination with a therapeutically effective amount of at least one other pharmacologically active substance.

19. A pharmaceutical composition comprising a compound according to claim 1 or a pharmaceutically acceptable salt thereof, and one or more pharmaceutically acceptable excipient(s).

20. A pharmaceutical preparation comprising a compound according to claim 1 or a pharmaceutically acceptable salt thereof, and at least one other pharmacologically active substance.

21. A compound selected from the group consisting of:
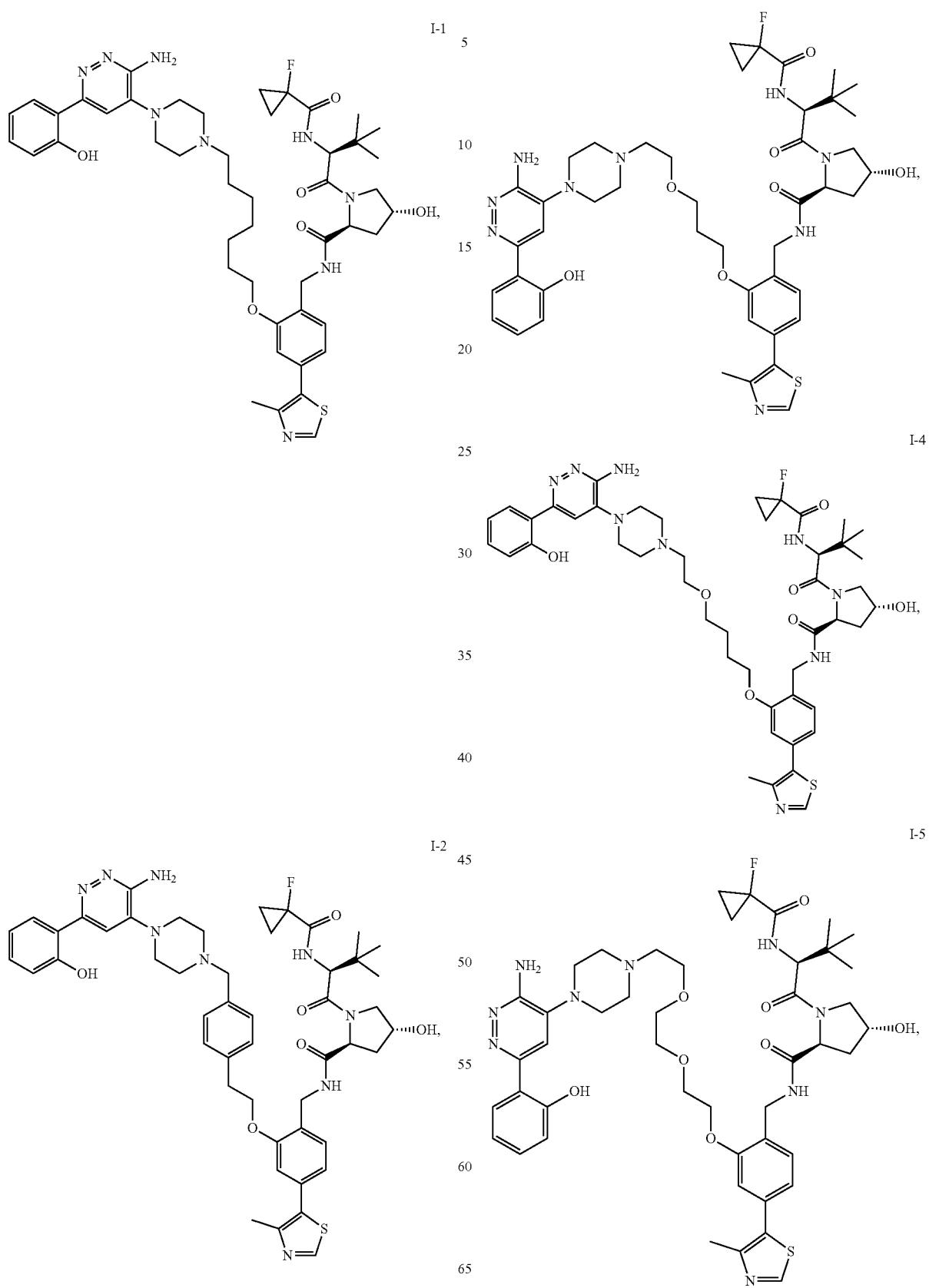

I-6
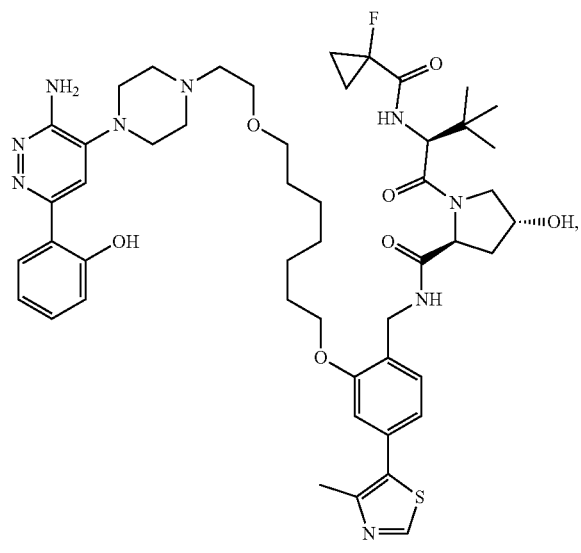
I-7
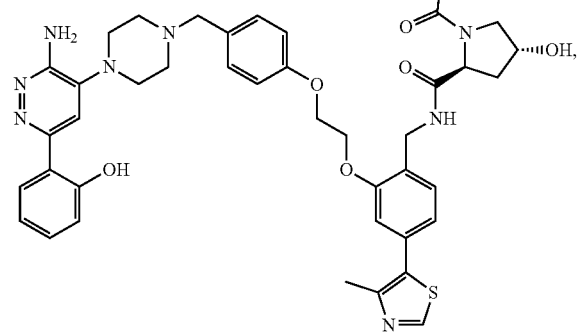
I-8
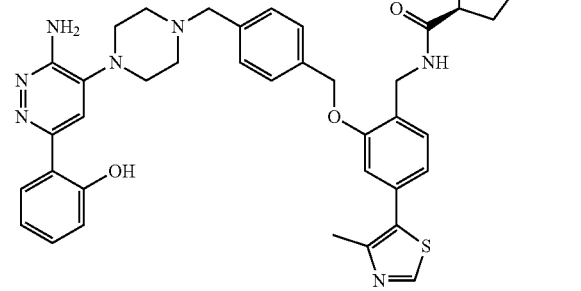
I-9
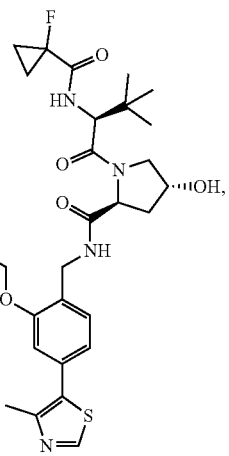
I-10
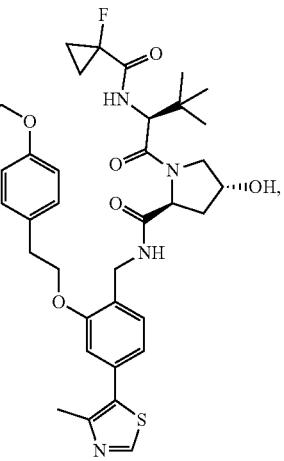
I-11
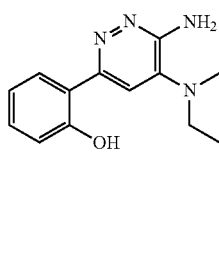
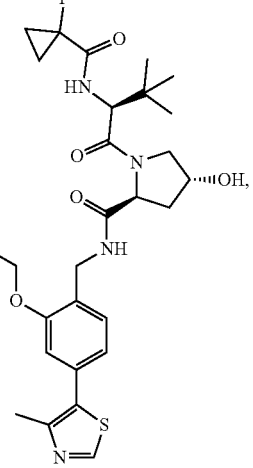

I-12
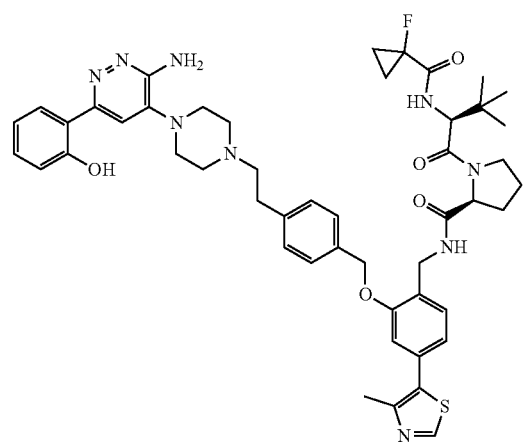
I-13
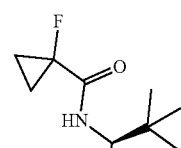
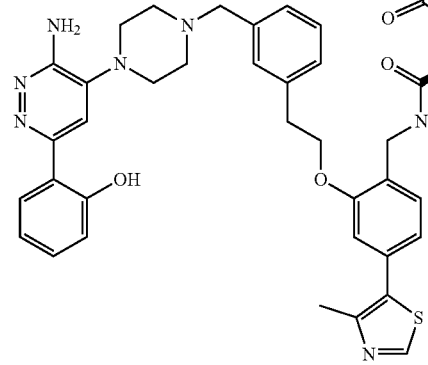
I-14
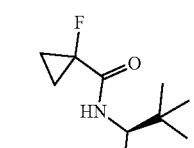
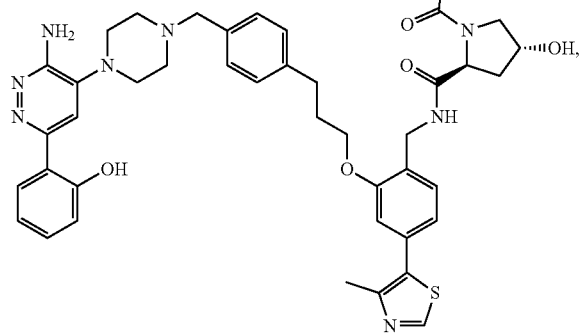
I-15
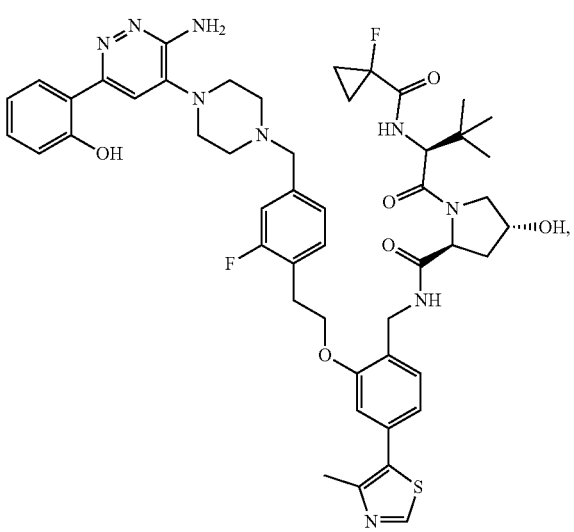
I-16
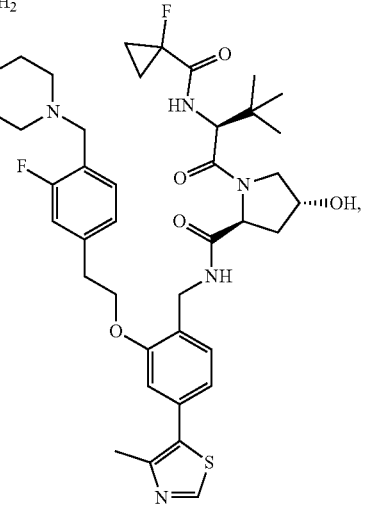
I-17
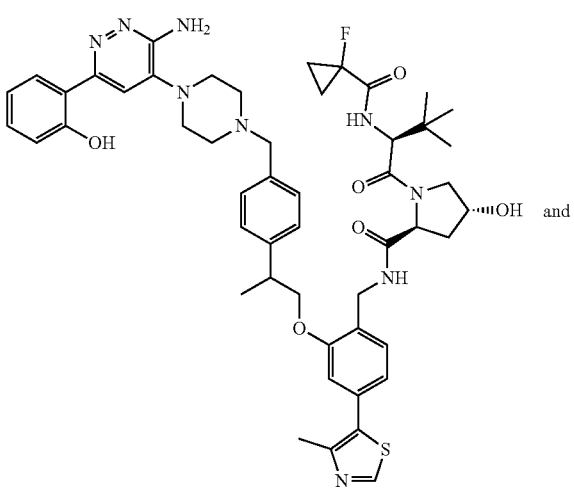
and I-18
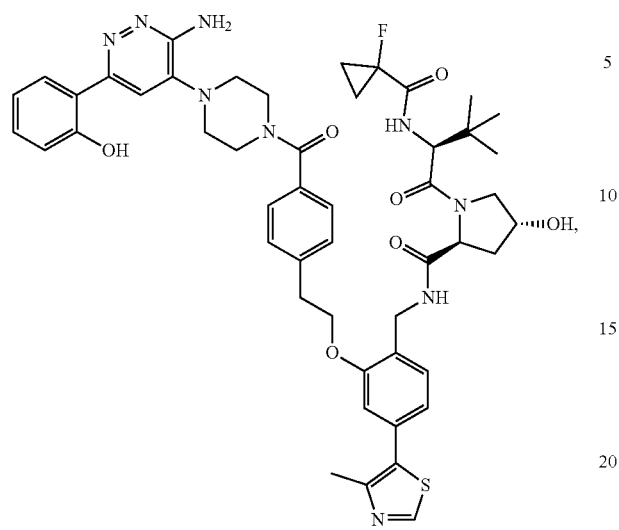
or a pharmaceutically acceptable salt thereof.
* * * * *